United States Patent
Crossman et al.

(10) Patent No.: US 6,720,141 B1
(45) Date of Patent: Apr. 13, 2004

(54) DIAGNOSTICS AND THERAPEUTICS FOR RESTENOSIS

(75) Inventors: David C. Crossman, Sheffield (GB); Gordon W. Duff, South Yorkshire (GB); Sheila E. Francis, Sheffield (GB); Kenneth S. Kornman, San Antonio, TX (US); Katherine Stephenson, San Antonio, TX (US)

(73) Assignee: Interleukin Genetics, Inc., Waltham, MA (US)

( * ) Notice: Subject to any disclaimer, the term of this patent is extended or adjusted under 35 U.S.C. 154(b) by 0 days.

(21) Appl. No.: 09/578,534

(22) Filed: May 24, 2000

Related U.S. Application Data

(63) Continuation-in-part of application No. 09/431,352, filed on Nov. 1, 1999.

(51) Int. Cl.$^7$ .......................... C12Q 1/68; C12P 19/34; C07H 21/02; C07H 21/04
(52) U.S. Cl. ......................... 435/6; 435/91.2; 536/23.5; 536/24.31; 536/24.33
(58) Field of Search .......................... 435/6, 91.2, 810; 536/24.31, 24.33, 23.5

(56) References Cited

U.S. PATENT DOCUMENTS

| | | | |
|---|---|---|---|
| 4,582,788 A | 4/1986 | Erlich | 435/6 |
| 4,623,619 A | 11/1986 | Owerbach et al. | 435/6 |
| 4,666,828 A | 5/1987 | Gusella | 435/6 |
| 4,801,531 A | 1/1989 | Frossard | 435/6 |
| 4,965,188 A | 10/1990 | Mullis et al. | 435/6 |
| 5,110,920 A | 5/1992 | Erlich | 536/27 |
| 5,268,267 A | 12/1993 | Smith | 435/6 |
| 5,554,509 A | 9/1996 | Collucci et al. | 435/6 |
| 5,955,266 A | * 9/1999 | Bray et al. | 435/6 |

FOREIGN PATENT DOCUMENTS

WO    WO 98/40517    9/1998

OTHER PUBLICATIONS

Alexander R. W., "Inflammation and Coronary Artery Disease", The New England Journal of Medicine, 331(7): 468–469 (1994).
Anderson & King, "Modern Approaches to the Diagnosis of Coronary Artery Disease", Am. Heart J. 123(5): 1312–1323 (1992).
Badimon, et al., "Coronary Atherosclerosis: A Multifactorial Disease", Supplement II Circulation, 87 (3): 11–3–11–16 (1993).
Clark, et al., "Genomic Sequence for Human Prointerleukin 1 beta: Possible Evolution from a Reverse Transcribed Prointerleukin 1 alpha gene", Nuc. Acids Res. 14 (20) : 7897–7914 (1986). Erratum in Nuc. Acids Res. 15 (2):868 (1987).
Clay, et al., "Interleukin 1 Receptor Antagonist Gene Polymorphism Association with Lichen Sclerosus", Hum. Genet. 94 : 407–410 (1994).
Clay, et al., "Novel Interleukin–1 Receptor Antagonist *Exon Polymorphisms* and their use in Allele–specific mRNA Assessement", Hum. Genet. 97 (6): 723–726 (Jun. 1996).
di Giovine et al., "Single Based Polymorphism at –511 in the Human Interleukin –1β Gene (IL 1β)", Human Molecular Genetics 1 (6) : 450 (1992).
Dinarello, et al., "Anticytokine Strategies in the Treatement of the Systemic Inflammatory Response Syndrome", JAMA, 269(14 1829–1835 (1993).
Dinarello, et al., "The Role of Interleukin–1 in Disease", The New England Journal of Medicine 328(2): 106–113 (Jan. 1993).
Francis, S.E. et al. (1999), *Interleukin–1 Receptor Antagonist Gene Polymorphism and Coronary Artery Disease*, Circulation 99(7):861.
Kastrati, A. et al. (2000), *Protection Against Restenosis From an Interleukin–1 Receptor Antagonist Gene Polymorphism in Patients Treated With Coronary Stenting*, J. Am. College Cardiology 35(2):36A.
Kornman, K.S. et al. (1999), *Interleukin–1 Genotypes and the Association Between Periodontitis and cardiovascular Disease*, J. Periodont. Res. 34:353.
Zee, R. et al. (1999), *Genetic Risk Factors for Post–PTCA Restenosis: A Comprehensive Analysis of Multiple Candidate Genes*, Circulation 110(18):755.
Duff, "Molecular Genet tokine", The Cytokine Handbook(19940 2 2 :21–30.
Galea, et al., "Interleukin–1β in Coronary Arteries of Patients With Ischemic Heart Disease", Ath. Thromb. And Vasc. Biol., 16(8): 1000–1006 (Aug. 1996).
Hasdai, et al., "Increased Serum Concentrations of Interleukin– 1β in Patients with Coronary Artery Disease", Heart, 76: 24–28 (1996).
Knox, "Discovery may help battle heart attacks", Houston Chronicle(Jan. 10, 1996).
Liuzzo, et al., "The Prognostic Value of C–reative Protein and Serum Amyloid A Protein in Severe Unstable Angina", N.E.J.M. 331(7): 417–424 (1994).
Mansfield et al., "Novel Genetic Association Between Ulcerative Colitis and the Anti–inflammatory Cytokine Interleukin– 1 Receptor Antagonist", Gastroenterology 106 (3):637–642 (1994).
Munro & Cotran, "Biology of Disease ; The Pathogenesis of Atherosclerosis: Atherogenesis and Inflammation", Lab. Invest. 58(3):249–261.
Nicklin, et al., "A Physical Map of the Region Encompassing the Human Interleukin–1α, Interleukin–1β, and Interleukin–1 Receptor Antagonist Genes", Genomics 19: 382–384 (1994).
Tarlow, et al., "Polymorphism in Human IL–1 Receptor Antagonist Gene Inton 2 is caused by Variable Numbers of an 86– bp Tandem Repeat", Hum. Genet. 91: 403–404 (1993).
Tarlow, et al., "Severity of Alopecia Areata Is Associated with a Polymorphism in the Interleukin –1 Receptor Antagonist Gene", J. Invest. Dermatol. 103: 387–390 (1994).
Cox et al.; "An Analysis of Linkage Disequilibrium in the Interleukin–1 Gene Cluster, Using a Novel Grouping Method for Multialletio Markers", Am. J. Hum. Genet. 62: 1180–1188, ( 1998).
Libby Peter, MD; "From Bench to Bedside: Molecular Bases of the Acute Coronary Syndromes", Circulation, 91(11): 2844–2850, (Jun. 1, 1995).
Ross Russell; "The Pathogenesis of Artherosclerosis: A Perspective for the 1990s", Nature, 362: 801–809, (Apr. 29, 1993).

\* cited by examiner

*Primary Examiner*—Carla J. Myers
(74) *Attorney, Agent, or Firm*—Ivor R. Elrifi, Esq.; Mintz, Levin, Cohn, Ferris, Glovsky and Popeo, P.C.

(57) ABSTRACT

Methods and kits for determining whether a subject has or is predisposed to developing restenosis are provide.

14 Claims, 19 Drawing Sheets

```
  -1437 AAGCTTCTAC CCTAGTCTGG TGCTACACTT ACATTGCTTA CATCCAAGTG TGGTTATTTC
  -1377 TGTGGCTCCT GTTATAACTA TTATAGCACC AGGTCTATGA CCAGGAGAAT TAGACTGGCA
  -1317 TTAAATCAGA ATAAGAGATT TTGCACCTGC AATAGACCTT ATGACACCTA ACCAACCCCA
  -1257 TTATTTACAA TTAAACAGGA ACAGAGGGAA TACTTTATCC AACTCACACA AGCTGTTTTC
  -1197 CTCCCAGATC CATGCTTTTT TGCGTTTATT ATTTTTTAGA GATGGGGGCT TCACTATGTT
  -1137 GCCCACACTG GACTAAAACT CTGGGCCTCA AGTGATTGTC CTGCCTCAGC CTCCTGAATA
  -1077 GCTGGGACTA CAGGGGCATG CCATCACACC TAGTTCATTT CCTCTATTTA AAATATACAT
  -1017 GGCTTAAACT CCAACTGGGA ACCCAAAACA TTCATTTGCT AAGAGTCTGG TGTTCTACCA
   -957 CCTGAACTAG GCTGGCCACA GGAATTATAA AGCTGAGAA ATTCTTTAAT AATAGTAACC
   -897 AGGCAACATC ATTGAAGGCT CATATGTAAA AATCCATGCC TTCCTTTCTC CCAATCTCCA
   -837 TTCCCAAACT TAGCCACTGG TTCTGGCTGA GGCCTTACGC ATACCTCCCG GGGCTTGCAC
   -777 ACACCTTCTT CTACAGAAGA CACACCTTGG GCATATCCTA CAGAAGACCA GGCTTCTCTC
   -717 TGGTCCTTGG TAGAGGGCTA CTTTACTGTA ACAGGGCCAG GGTGGAGAGT TCTCTCCTGA
   -657 AGCTCCATCC CCTCTATAGG AAATGTGTTG ACAATATTCA GAAGAGTAAG AGGATCAAGA
   -597 CTTCTTTGTG CTCAAATACC ACTGTTCTCT TCTCTACCCT GCCCTAACCA GGAGCTTGTC
   -537 ACCCCAAACT CTGAGGTGAT TTATGCCTTA ATCAAGCAAA CTTCCCTCTT CAGAAAAGAT
   -477 GGCTCATTTT CCCTCAAAAG TTGCCAGGAG CTGCCAAGTA TTCTGCCAAT TCACCCTGGA
   -417 GCACAATCAA CAAATTCAGC CAGAACACAA CTACAGCTAC TATTAGAACT ATTATTATTA
   -357 ATAAATTCCT CTCCAAATCT AGCCCCTTGA CTTCGGATTT CACGATTTCT CCCTTCCTCC
   -297 TAGAAACTTG ATAAGTTTCC CGCGCTTCCC TTTTTCTAAG ACTACATGTT TGTCATCTTA
   -237 TAAAGCAAAG GGGTGAATAA ATGAACCAAA TCAATAACTT CTGGAATATC TGCAAACAAC
   -177 AATAATATCA GCTATGCCAT CTTTCACTAT TTTAGCCAGT ATCGAGTTGA ATGAACATAG
   -117 AAAAATACAA AACTGAATTC TTCCCTGTAA ATTCCCCGTT TGACGACGC ACTTGTAGCC
    -57 ACGTAGCCAC GCCTACTTAA GACAATTACA AAAGGCGAAG AAGACTGACT CAGGCTTAAG
      4 CTGCCAGCCA GAGAGGGAGT CATTTCATTG GCGTTTGAGT CAGCAAAGGT ATTGTCCTCA
     64 CATCTCTGGC TATTAAAGTA TTTTCTGTTG TTGTTTTTCT CTTTGGCTGT TTTCTCTCAC
    124 ATTGCCTTCT CTAAAGCTAC AGTCTCTCCT TTCTTTTCTT GTCCCTCCCT GGTTTGGTAT
    184 GTGACCTAGA ATTACAGTCA GATTTCAGAA AATGATTCTC TCATTTGCT GATAAGGACT
    244 GATTCGTTTT ACTGAGGGAC GGCAGAACTA GTTTCCTATG AGGGCATGGG TGAATACAAC
    304 TGAGGCTTCT CATGGGAGGG AATCTCTACT ATCCAAAATT ATTAGGAGAA AATTGAAAAT
    364 TTCCAACTCT GTCTCTCTCT TACCTCTGTG TAAGGCAAAT ACCTTATTCT TGTGGTGTTT
    424 TTGTAACCTC TTCAAACTTT CATTGATTGA ATGCCTGTTC TGGCAATACA TTAGGTTGGG
    484 CACATAAGGA ATACCAACAT AAATAAAACA TTCTAAAAGA AGTTTACGAT CTAATAAAGG
    544 AGACAGGTAC ATAGCAAACT AATTCAAAGG AGCTAGAAGA TGGAGAAAAT GCTGAATGTG
    604 GACTAAGTCA TTCAACAAAG TTTTCAGGAA GCACAAAGAG GAGGGCTCC CCTCACAGAT
    664 ATCTGGATTA GAGGCTGGCT GAGCTGATGG TGGCTGGTGT TCTCTGTTGC AGAAGTCAAG
    724 ATGGCCAAAG TTCCAGACAT GTTTGAAGAC CTGAAGAACT GTTACAGGTA AGGAATAAGA
    784 TTTATCTCTT GTGATTTAAT GAGGGTTTCA AGGCTCACCA GAATCCAGCT AGGCATAACA
    844 GTGGCCAGCA TGGGGGCAGG CCGGCAGAGG TTGTAGAGAT GTGTACTAGT CCTGAAGTCA
    904 GAGCAGGTTC AGAGAAGACC CAGAAAAACT AAGCATTCAG CATGTTAAAC TGAGATTACA
    964 TTGGCAGGGA GACCGCCATT TTAGAAAAAT TATTTTTGAG GTCTGCTGAG CCCTACATGA
   1024 ATATCAGCAT CAACTTAGAC ACAGCCTCTG TTGAGATCAC ATGCCCTGAT ATAAGAATGG
   1084 GTTTTACTGG TCCATTCTCA GGAAAACTTG ATCTCATTCA GGAACAGGAA ATGGCTCCAC
   1144 AGCAAGCTGG GCATGTGAAC TCACATATGC AGGCAAATCT CACTCAGATG TAGAAGAAAG
   1204 GTAAATGAAC ACAAAGATAA AATTACGGAA CATATTAAAC TAACATGATG TTTCCATTAT
   1264 CTGTAGTAAA TACTAACACA AACTAGGCTG TCAAAATTTT GCCTGGATAT TTTACTAAGT
   1324 ATAAATTATG AAATCTGTTT TAGTGAATAC ATGAAAGTAA TGTGTAACAT ATAATCTATT
   1384 TGGTTAAAAT AAAAGGAAG TGCTTCAAAA CCTTTCTTTT CTCTAAAGGA GCTTAACATT
   1444 CTTCCCTGAA CTTCAATTAA AGCTCTTCAA TTTGTTAGCC AAGTCCAATT TTTACAGATA
   1504 AAGCACAGGT AAAGCTCAAA GCCTGTCTTG ATGACTACTA ATTCCAGATT AGTAAGATAT
```

Fig. 1

```
1564 GAATTACTCT ACCTATGTGT ATGTGTAGAA GTCCTTAAAT TTCAAAGATG ACAGTAATGG
1624 CCATGTGTAT GTGTGTGACC CACAACTATC ATGGTCATTA AAGTACATTG GCCAGAGACC
1684 ACATGAAATA ACAACAATTA CATTCTCATC ATCTTATTTT GACAGTGAAA ATGAAGAAGA
1744 CAGTTCCTCC ATTGATCATC TGTCTCTGAA TCAGGTAAGC AAATGACTGT AATTCTCATG
1804 GGACTGCTAT TCTTACACAG TGGTTTCTTC ATCCAAAGAG AACAGCAATG ACTTGAATCT
1864 TAAATACTTT TGTTTTACCC TCACTAGAGA TCCAGAGACC TGTCTTTCAT TATAAGTGAG
1924 ACCAGCTGCC TCTCTAAACT AATAGTTGAT GTGCATTGGC TTCTCCCAGA ACAGAGCAGA
1984 ACTATCCCAA ATCCCTGAGA ACTGGAGTCT CCTGGGGCAG GCTTCATCAG GATGTTAGTT
2044 ATGCCATCCT GAGAAAGCCC CGCAGGCCGC TTCACCAGGT GTCTGTCTCC TAACGTGATG
2104 TGTTGTGGTT GTCTTCTCTG ACACCAGCAT CAGAGGTTAG AGAAAGTCTC CAAACATGAA
2164 GCTGAGAGAG AGGAAGCAAG CCAGCTGAAA GTGAGAAGTC TACAGCCACT CATCAATCTG
2224 TGTTATTGTG TTTGGAGACC ACAAATAGAC ACTATAAGTA CTGCCTAGTA TGTCTTCAGT
2284 ACTGGCTTTA AAAGCTGTCC CCAAAGGAGT ATTTCTAAAA TATTTTGAGC ATTGTTAAGC
2344 AGATTTTTAA CCTCCTGAGA GGGAACTAAT TGGAAAGCTA CCACTCACTA CAATCATTGT
2404 TAACCTATTT AGTTACAACA TCTCATTTTT GAGCATGCAA ATAAATGAAA AAGTCTTCCT
2464 AAAAAAATCA TCTTTTTATC CTGGAAGGAG GAAGGAAGGT GAGACAAAAG GGAGAGAGGG
2524 AGGGAAGCCT AATGAAACAC CAGTTACCTA AGACCAGAAT GGAGATCCTC CTCACTACCT
2584 CTGTTGAATA CAGCACCTAC TGAAAGAACT TTCATTCCCT GACCATGAAC AGCCTCTCAG
2644 CTTCTGTTTT CCTTCCTCAC AGAAATCCTT CTATCATGTA AGCTATGGCC CACTCCATGA
2704 AGGCTGCATG GATCAATCTG TGTCTCTGAG TATCTCTGAA ACCTCTAAAA CATCCAAGCT
2764 TACCTTCAAG GAGAGCATGG TGGTAGTAGC AACCAACGGG AAGGTTCTGA AGAAGAGACG
2824 GTTGAGTTTA AGCCAATCCA TCACTGATGA TGACCTGGAG GCCATCGCCA ATGACTCAGA
2884 GGAAGGTAAG GGGTCAAGCA CAATAATATC TTTCTTTTAC AGTTTTAAGC AAGTAGGGAC
2944 AGTAGAATTT AGGGGAAAAT TAAACGTGGA GTCAGAATAA CAAGAAGACA ACCAAGCATT
3004 AGTCTGGTAA CTATACAGAG GAAAATTAAT TTTTATCCTT CTCCAGGAGG GAGAAATGAG
3064 CAGTGGCCTG AATCGAGAAT ACTTGCTCAC AGCCATTATT CTTAGCCAT ATTGTAAAGG
3124 TCGTGTGACT TTTAGCCTTT CAGGAGAAAG CAGTAATAAG ACCACTTACG AGCTATGTTC
3184 CTCTCATACT AACTATGCCT CCTTGGTCAT GTTACATAAT CTTTTCGTGA TTCAGTTTCC
3244 TCTACTGTAA AATGGAGATA ATCAGAATCC CCCACTCATT GGATTGTTGT AAAGATTAAG
3304 AGTCTCAGGC TTTACAGACT GAGCTAGCTG GGCCCTCCTG ACTGTTATAA AGATTAAATG
3364 AGTCAACATC CCCTAACTTC TGGACTAGAA TAATGTCTGG TACAAAGTAA GCACCCAATA
3424 AATGTTAGCT ATTACTATCA TTATTATTAT TATTTTATTT TTTTTTTTTG AGATGGAGTC
3484 TGGCTCTGTC ACCCAGGCTG GAGTGCAGTG GCACAATCTC GGCTCACTGC AAGCTCTGCC
3544 TCCTGGGTTC ATGCCATTCT CCTGCCTCAG CCTCCCGAGT AAGCTGGGAA TACAGGCACC
3604 CGCCACTGTT CCCGGCTAAT TTTTTGTATT TTTAGTAGAG.ACGGAGTTTC ACCGTGGTCT
3664 CCATCTCCTC GTGATCCACC CACCTTGGCC TCCCAAAGTG CCGGGATTAC AGGCGTGAGC
3724 CACCGCGCCC GGCCTATTAT TATTATTATT ACTACTACTA CTACCTATAT GAATACTACC
3784 AGCAATACTA ATTTATTAAT GACTGGATTA TGTCTAAACC TCACAAGAAT CCTACCTTCT
3844 CATTTTACAT AAAAGGAAAC TAAGCTCATT GAGATAGGTA AACTGCCCAA TGGCATACAT
3904 CTGTAAGTGG GAGAGCCTCA AATCTAATTC AGTTCTACCT GAGTAAAAAA ATCATGGTTT
3964 CTCCTCCATC CCTTTACTGT ACAAGCCTCC ACATGAACTA TAAACCCAAT ATTCCTGTTT
4024 TTAAGATAAT ACCTAAGCAA TAACGCATGT TCACCTAGAA GGTTTTAAAA TGTAACAAAA
4084 TATAAGAAAA TAAAAATCAC TCATATCGTC AGTGAGAGTT TACTACTGCC AGCACTATGG
4144 TATGTTTCCT TAAAATCTTT GCTATACACA TACCTACATG TGAACAAATA TGTCTAACAT
4204 CAAGACCACA CTATTTACAA CTTTATATCC AGCTTTTCTT ACTTAGCAAT GTATTGAGGA
4264 CATTTTAGAG TGCCCGTTTT TCACCATTAT AAGCAATGCA ACAATGAACA TCTGTATAAA
4324 TAAATATTCA TTTCTCTCAC CCTTTATTTC CTTAGAATAT ATTCCTAGAA GTAGAATTTC
4384 CCAGAGCCAT GAGGATTTGT GACGCTATTG ATATGTGCCA CTTTGCACTC TCTGTGACAT
4444 ATATAATTAT TTTTAATGCA TTCATTTTTT TCTCAGAGTG CATTCGTTTG AAAACATAGA
4504 CGGGAAATAC TGGTAGTCTT CCTTGTCAGT TAGAAACACC CAAACAATGA AAAATGAAAA
4564 AGTTGCACAA ATAGTCTCTA AAAACAATGA AACTATTGCC TGAGGAATTG AAGTTTAAAA
4624 AGAAGCACAT AAGCAACAAC AAGGATAATC CTAGAAAACC AGTTCTGCTG ACTGGGTGAT
4684 TTCACTTCTC TTTGCTTCCT CATCTGGATT GGAATATTCC TAATACCCCC TCCAGAACTA
```

Fig. 1 (cont.)

```
4744 TTTTCCCTGT TTGTACTAGA CTGTGTATAT CATCTGTGTT TGTACATAGA CATTAATCTG
4804 CACTTGTGAT CATGGTTTTA GAAATCATCA AGCCTAGGTC ATCACCTTTT AGCTTCCTGA
4864 GCAATGTGAA ATACAACTTT ATGAGGATCA TCAAATACGA ATTCATCCTG AATGACGCCC
4924 TCAATCAAAG TATAATTCGA GCCAATGATC AGTACCTCAC GGCTGCTGCA TTACATAATC
4984 TGGATGAAGC AGGTACATTA AAATGGCACC AGACATTTCT GTCATCCTCC CCTCCTTTCA
5044 TTTACTTATT TATTTATTTC AATCTTTCTG CTTGCAAAAA ACATACCTCT TCAGAGTTCT
5104 GGGTTGCACA ATTCTTCCAG AATAGCTTGA AGCACAGCAC CCCCATAAAA ATCCCAAGCC
5164 AGGGCAGAAG GTTCAACTAA ATCTGGAAGT TCCACAAGAG AGAAGTTTCC TATCTTTGAG
5224 AGTAAAGGGT TGTGCACAAA GCTAGCTGAT GTACTACCTC TTTGGTTCTT TCAGACATTC
5284 TTACCCTCAA TTTTAAAACT GAGGAAACTG TCAGACATAT TAAATGATTT ACTCAGATTT
5344 ACCCAGAAGC CAATGAAGAA CAATCACTCT CCTTTAAAAA GTCTGTTGAT CAAACTCACA
5404 AGTAACACCA AACCAGGAAG ATCTTTATTA TCTCTGATAA CATATTTGTG AGGCAAAACC
5464 TCCAATAAGC TACAAATATG GCTTAAGGA TGAAGTTTAG TGTCCAAAAA CTTTTATCAC
5524 ACACATCCAA TTTTCATGGC GGACATGTTT TAGTTTCAAC AGTATACATA TTTTCAAAGG
5584 TCCAGAGAGG CAATTTTGCA ATAAACAAGC AAGACTTTTT CTGATTGGAT GCACTTCAGC
5644 TAACATGCTT TCAACTCTAC ATTTACAAAT TATTTTGTGT TCTATTTTTC TACTTAATAT
5704 TATTTCTGCA ATTTTCCCAA TATTGACATC GTGTATGTAT TTGCCATTTT TAATATCACT
5764 AGACAATTCA ATCAGGTTGC TACGTTGGTC CCTTGGGTTT ACTCTAAATA GCTTGATTGC
5824 AAATATCTTT GTATATATTA TTGTTTTTTC TCCTATCTTG TAATTTCTTT GAGCACATCC
5884 CAAAGAGGAA TGCCTAGATC AATGGGCACA AATAATTTGA CAGCTCTTAT TAAACATTAT
5944 TCTGTAAGTA AAAACTGAAC TACTTTTCAG TATCACTAGC AACATATGAG TGTATCAGCT
6004 TCCTAAACCC CTCCATGTTA GGTCATTATG AACTTATGAT CTAACAAATT ACAGGGTCTT
6064 ATCCCACTAA TGAAATTATA AGAGATTCAA CACTTATTCA GCCCGAAGG ATTCATTCAA
6124 CGTAGAAAAT TCTAAGAACA TTAACCAAGT ATTTACCTGC CTAGTGAGTG TGGAAGACAT
6184 TGTGAAGGAC ACAAAGATGT ATAGAATTCC ATTCCTGACT TCCAGGTATT TACACCATAG
6244 GTGGGGACCT AACTACACAC ACACACACAC ACACACACAC ACACACACAC ACCATGCACA
6304 CACAATCTAC ATCAACACTT GATTTTATAC AAATACAATG AATTTACTTT CTTTTTGGTT
6364 CTTCTCTTCA CCAGTGAAAT TTGACATGGG TGCTTATAAG TCATCAAAGG ATGATGCTAA
6424 AATTACCGTG ATTCTAAGAA TCTCAAAAAC TCAATTGTAT GTGACTGCCC AAGATGAAGA
6484 CCAACCAGTG CTGCTGAAGG TCAGTTGTCC TTTGTCTCCA ACTTACCTTC ATTTACATCT
6544 CATATGTTTG TAAATAAGCC CAATAGGCAG ACACCTCTAA CAAGGTGACA CTGTCCTCTT
6604 TCCTTCCTAC CACAGCCCCC ACCTACCCAC CCCACTCCCA TTGATTCCAG AGGCGTGCCT
6664 AGGCAGGATC TATGAGAAAA TATAACAGAG AGTAAGAGGA AAATTACCTT CTTTCTTTTT
6724 CCTTTCCCTG CCTGACCTTA TTCACCTCCC ATCCCAGAGC ATCCATTTAT TCCATTGATC
6784 TTTACTGACA TCTATTATCT GACCTACACA ATACTAGACA TTAGGACAAT GTGGCCTGCC
6844 TCCAAGAAAC TCAAATAAGC CAACTGAGAT CAGAGAGGAT TAATCACCTG CCAATGGGCA
6904 CAAAGCAACA AGCTGGGAGC CAAGTCCCAA AATGGGGCCT GCTGCTTCCA GTTCCCCTCT
6964 CTCTGCATTG ATGTCAGCAT TATCCTTCGT CCCAGTCCTG TCTCCACTAC CACTTTCCCC
7024 CTCAAACACA CACACACACA ACAGCCTTAG ATGTTTTCTC CACTGATAAG TAGGTGACTC
7084 AATTTGTAAG TATATAATCC AAGACCTTCT ATTCCCAAGT AGAATTTATG TGCCTGCCTG
7144 TGCTTTTCTA CCTGGATCAA GTGATGTCTA CAGAGTAGGG CAGTAGCTTC ATTCATGAAC
7204 TCATTCAACA AGCATTATTC ACTGAGAGCC TTGTATTTTT CAGGCATAGT GCCAACAGCA
7264 GTGTGGACAG TGGTGCATCA AAGCCTCTAG TCTCATAGAA CTTAGTCTTC TGGAGGATAT
7324 GGAAAACAGA CAACCCAAAC AACCAACAAA AGAGCAAGAT GCTGCAAAAA AAAAAAAAT
7384 GAATAGGGTG CTAAGATAGA GAAAAGTGGG AGAGTGCTAT TTAGACAAAG TGGTAAAAAC
7444 AAAGCCCCTT GTGAGATGAG AGCTGCCGAC AGAGGGGCG GGTCATGGTT GTGGGTTTTT
7504 GGGTAGGACA TTCAGAGGAG GGGGCGGGTC GTGGTTGTGG GTTTTTGGGT AGGACATTCA
7564 GAGGAGGGGG CGGGTCGTGG TTGTGGGTTT TTGGGTAGGA CATTCAGAGG AGGGGGCGGG
7624 TCGTGGTTGT GGGTTTTTGG GTAGGACATT CAGAGGAGGG GGCGGGTCGT GGTTGTGGGT
7684 TTTGGGACA TTCAGAGGAG TCTGAATGCA CCCAGGCCTA CAACTTCAAG ATGGTAAAGG
7744 ACAGCTCCAA GGATCAGAAG AAGCATTCTT GGAACTGGGG CATTTTGAGA AGGAGGAAAA
7804 ATATGCAGAG ACTAGTGCTT GCAGAGCTTG CATTTGGATT TCATTTGAGG TACAATGAAA
7864 ACCCATTAAT GGGTTTCACA CAGTGCAATG GCCTGACCTC ACTTATATTT CCTAAAATAG
```

Fig. 1 (cont.)

```
7924  AAAACAGATC AGAAGGAAGG CAATAGAGAA GCAGAAAGTC CAATGAGGAG GTTTCACAGC
7984  AGTCATGGGG GTGGGGTAAG GAAAAGAAGT GGAAAGAAAC AGACAGAATT GGGTTATATT
8044  TTGGAGATAG AACCAACAGA AGGAAGAGGA GAAACAACAT TTACTGAGAA GGGAAAAAGT
8104  AGGAGAGGAA TAGGTTTGGG AAATAAATCC TGCTGACATT GGAAACCCCA AGGAAGCCTC
8164  AAAAGTATAT TTACTTGCTT TAGATTTAAA AGAATAGGAA AGAAGCATCT CAACTTGGAA
8224  TTTGAAATCT ATTTTTCCAT AAAAGTATTG TTAAATTCTA CTCATACTCA CAAGAAAAGT
8284  ACATTCTAAA GAGTATATTG AAAGAGTTTA CTGATATACT TAGGAATTTT GTGTGTATGT
8344  GTGTGTGTGT ATGTGTGTGT GTGTGTTTAA CCTTCAATTG TTGACTTAAA TACTGAGATA
8404  AATGTCATCT AAATGCTAAA TTGATTTCCC AAAGGTATGA TTTGTTCACT TGGAGATCAA
8464  AATGTTTAGG GGGCTTAGAA TCACTGTAGT GCTCAGATTT GATGCAAAAT GTCTTAGGCC
8524  TATGTTGAAG GCAGGACAGA AACAATGTTT CCCTCCTACC TGCCTGGATA CAGTAAGATA
8584  CTAGTGTCAC TGACAATCTT CATAACTAAT TTAGATCTCT CTCCAATCAA CTAAGGAAAT
8644  CAACTCTTAT TAATAGACTG GGCCACACAT CTACTAGGCA TGTAATAAAT GCTTGCTGAA
8704  TGAACAAATG AATGAAGAGC CTATAGCATC ATGTTACAGC CATAGTCCTA AAGTGGTGTT
8764  TCTCATGAAG GCCAAATGCT AAGGGATTGA GCTTCAGTCC TTTTTCTAAC ATCTTGTTCT
8824  CTAACAGAAT TCTCTTCTTT TCTTCATAGG AGATGCCTGA GATACCCAAA ACCATCACAG
8884  GTAGTGAGAC CAACCTCCTC TTCTTCTGGG AAACTCACGG CACTAAGAAC TATTTCACAT
8944  CAGTTGCCCA TCCAAACTTG TTTATTGCCA CAAAGCAAGA CTACTGGGTG TGCTTGGCAG
9004  GGGGGCCACC CTCTATCACT GACTTTCAGA TACTGGAAAA CCAGGCGTAG GTCTGGAGTC
9064  TCACTTGTCT CACTTGTGCA GTGTTGACAG TTCATATGTA CCATGTACAT GAAGAAGCTA
9124  AATCCTTTAC TGTTAGTCAT TTGCTGAGCA TGTACTGAGC CTTGTAATTC TAAATGAATG
9184  TTTACACTCT TTGTAAGAGT GGAACCAACA CTAACATATA ATGTTGTTAT TTAAAGAACA
9244  CCCTATATTT TGCATAGTAC CAATCATTTT AATTATTATT CTTCATAACA ATTTTAGGAG
9304  GACCAGAGCT ACTGACTATG GCTACCAAAA AGACTCTACC CATATTACAG ATGGGCAAAT
9364  TAAGGCATAA GAAAACTAAG AAATATGCAC AATAGCAGTT GAAACAAGAA GCCACAGACC
9424  TAGGATTTCA TGATTTCATT TCAACTGTTT GCCTTCTGCT TTTAAGTTGC TGATGAACTC
9484  TTAATCAAAT AGCATAAGTT TCTGGGACCT CAGTTTTATC ATTTTCAAAA TGGAGGGAAT
9544  AATACCTAAG CCTTCCTGCC GCAACAGTTT TTTATGCTAA TCAGGGAGGT CATTTTGGTA
9604  AAATACTTCT CGAAGCCGAG CCTCAAGATG AAGGCAAAGC ACGAAATGTT ATTTTTTAAT
9664  TATTATTTAT ATATGTATTT ATAAATATAT TTAAGATAAT TATAATATAC TATATTTATG
9724  GGAACCCCTT CATCCTCTGA GTGTGACCAG GCATCCTCCA CAATAGCAGA CAGTGTTTTC
9784  TGGGATAAGT AAGTTTGATT TCATTAATAC AGGGCATTTT GGTCCAAGTT GTGCTTATCC
9844  CATAGCCAGG AAACTCTGCA TTCTAGTACT TGGGAGACCT GTAATCATAT AATAAATGTA
9904  CATTAATTAC CTTGAGCCAG TAATTGGTCC GATCTTGAC TCTTTTGCCA TTAAACTTAC
9964  CTGGGCATTC TTGTTTCATT CAATTCCACC TGCAATCAAG TCCTACAAGC TAAAATTAGA
10024 TGAACTCAAC TTTGACAACC ATGAGACCAC TGTTATCAAA ACTTTCTTTT CTGGAATGTA
10084 ATCAATGTTT CTTCTAGGTT CTAAAAATTG TGATCAGACC ATAATGTTAC ATTATTATCA
10144 ACAATAGTGA TTGATAGAGT GTTATCAGTC ATAACTAAAT AAAGCTTGCA ACAAAATTCT
10204 CTGACACATA GTTATTCATT GCCTTAATCA TTATTTTACT GCATGGTAAT TAGGGACAAA
10264 TGGTAAATGT TTACATAAAT AATTGTATTT AGTGTTACTT TATAAAATCA AACCAAGATT
10324 TTATATTTTT TTCTCCTCTT TGTTAGCTGC CAGTATGCAT AAATGGCATT AAGAATGATA
10384 ATATTTCCGG GTTCACTTAA AGCTCATATT ACACATACAC AAAACATGTG TTCCCATCTT
10444 TATACAAACT CACACATACA GAGCTACATT AAAAACAACT AATAGGCCAG GCACGGTGGC
10504 TCAGACCTGT AATCCCAGCA CTTTGGGAGG
```

Fig. 1 (cont.)

```
-1933 AGAAAGAAAG AGAGAGAGAA AGAAAAGAAA GAGGAAGGAA GGAAGGAAGG AAGAAAGACA
-1873 GGCTCTGAGG AAGGTGGCAG TTCCTACAAC GGGAGAACCA GTGGTTAATT TGCAAAGTGG
-1813 ATCCTGTGGA GGCANNCAGA GGAGTCCCCT AGGCCACCCA GACAGGGCTT TTAGCTATCT
-1753 GCAGGCCAGA CACCAAATTT CAGGAGGGCT CAGTGTTAGG AATGGATTAT GGCTTATCAA
-1693 ATTCACAGGA AACTAACATG TTGAACAGCT TTTAGATTTC CTGTGGAAAA TATAACTTAC
-1633 TAAAGATGGA GTTCTTGTGA CTGACTCCTG ATATCAAGAT ACTGGGAGCC AAATTAAAAA
-1573 TCAGAAGGCT GCTTGGAGAG CAAGTCCATG AAATGCTCTT TTTCCCACAG TAGAACCTAT
-1513 TTCCCTCGTG TCTCAAATAC TTGCACAGAG GCTCACTCCC TTGGATAATG CAGAGCGAGC
-1453 ACGATACCTG GCACATACTA ATTTGAATAA AATGCTGTCA AATTCCCATT CACCCATTCA
-1393 AGCAGCAAAC TCTATCTCAC CTGAATGTAC ATGCCAGGCA CTGTGCTAGA CTTGGCTCAA
-1333 AAAGATTTCA GTTTCCTGGA GGAACCAGGA GGGCAAGGTT TCAACTCAGT GCTATAAGAA
-1273 GTGTTACAGG CTGGACACGG TGGCTCACGC CTGTAATCCC AACATTTGGG AGGCCGAGGC
-1213 GGGCAGATCA CAAGGTCAGG AGATCGAGAC CATCCTGGCT AACATGGTGA AACCCTGTCT
-1153 CTACTAAAAA TACAAAAAAT TAGCCGGGCG TTGGCGGCAG GTGCCTGTAG TCCCAGCTGC
-1093 TGGGGAGGCT GAGGCAGGAG AATGGTGTGA ACCCGGGAGG CGGAACTTGC AGGGGGCCGA
-1033 GATCGTGCCA CTGCACTCCA GCCTGGGCGA CAGAGTGAGA CTCTGTCTCA AAAAAAAAAA
 -973 AAAAGTGTTA TGATGCAGAC CTGTCAAAGA GGCAAAGGAG GGTGTTCCTA CACTCCAGGC
 -913 ACTGTTCATA ACCTGGACTC TCATTCATTC TACAAATGGA GGGCTCCCCT GGGCAGATCC
 -853 CTGGAGCAGG CACTTTGCTG GTGTCTCGGT TAAAGAGAAA CTGATAACTC TTGGTATTAC
 -793 CAAGAGATAG AGTCTCAGAT GGATATTCTT ACAGAAACAA TATTCCCACT TTTCAGAGTT
 -733 CACCAAAAAA TCATTTTAGG CAGAGCTCAT CTGGCATTGA TCTGGTTCAT CCATGAGATT
 -673 GGCTAGGGTA ACAGCACCTG GTCTTGCAGG GTTGTGTGAG CTTATCTCCA GGGTTGCCCC
 -613 AACTCCGTCA GGAGCCTGAA CCCTGCATAC CGTATGTTCT CTGCCCCAGC CAAGAAAGGT
 -553 CAATTTTCTC CTCAGAGGCT CCTGCAATTG ACAGAGAGCT CCCGAGGCAG AGAACAGCAC
 -493 CCAAGGTAGA GACCCACACC CTCAATACAG ACAGGGAGGG CTATTGGCCC TTCATTGTAC
 -433 CCATTTATCC ATCTGTAAGT GGGAAGATTC CTAAACTTAA GTACAAAGAA GTGAATGAAG
 -373 AAAAGTATGT GCATGTATAA ATCTGTGTGT CTTCCACTTT GTCCCACATA TACTAAATTT
 -313 AAACATTCTT CTAACGTGGG AAAATCCAGT ATTTTAATGT GGACATCAAC TGCACAACGA
 -253 TTGTCAGGAA AACAATGCAT ATTTGCATGG TGATACATTT GCAAAATGTG TCATAGTTTG
 -193 CTACTCCTTG CCCTTCCATG AACCAGAGAA TTATCTCAGT TTATTAGTCC CCTCCCCTAA
 -133 GAAGCTTCCA CCAATACTCT TTTCCCCTTT CCTTTAACTT GATTGTGAAA TCAGGTATTC
  -73 AACAGAGAAA TTTCTCAGCC TCCTACTTCT GCTTTTGAAA GCTATAAAAA CAGCGAGGGA
  -13 GAAACTGGCA GATACCAAAC CTCTTCGAGG CACAAGGCAC AACAGGCTGC TCTGGGATTC
   48 TCTTCAGCCA ATCTTCATTG CTCAAGTATG ACTTTAATCT TCCTTACAAC TAGGTGCTAA
  108 GGGAGTCTCT CTGTCTCTCT GCCTCTTTGT GTGTATGCAT ATTCTCTCTC TCTCTCTCTT
  168 TCTTTCTCTG TCTCTCCTCT CCTTCCTCTC TGCCTCCTCT CTCAGCTTTT TGCAAAAATG
  228 CCAGGTGTAA TATAATGCTT ATGACTCGGG AAATATTCTG GAATGGATA CTGCTTATCT
  288 AACAGCTGAC ACCCTAAAGG TTAGTGTCAA AGCCTCTGCT CCAGCTCTCC TAGCCAATAC
  238 ATTGCTAGTT GGGGTTTGGT TTAGCAAATG CTTTTCTCTA GACCCAAAGG ACTTCTCTTT
  308 CACACATTCA TTCATTTACT CAGAGATCAT TTCTTTGCAT GACTGCCATG CACTGGATGC
  468 TGAGAGAAAT CACACATGAA CGTAGCCGTC ATGGGGAAGT CACTCATTTT CTCCTTTTTA
  528 CACAGGTGTC TGAAGCAGCC ATGGCAGAAG TACCTGAGCT CGCCAGTGAA ATGATGGCTT
  588 ATTACAGGTC AGTGGAGACG CTGAGACCAG TAACATGAGC AGGTCTCCTC TTTCAAGAGT
  648 AGAGTGTTAT CTGTGCTTGG AGACCAGATT TTTCCCCTAA ATTGCCTCTT TCAGTGGCAA
  708 ACAGGGTGCC AAGTAAATCT GATTTAAAGA CTACTTTCCC ATTACAAGTC CCTCCAGCCT
  768 TGGGACCTGG AGGCTATCCA GATGTGTTGT TGCAAGGGCT TCCTGCAGAG GCAAATGGGG
  828 AGAAAAGATT CCAAGCCCAC AATACAAGGA ATCCCTTTGC AAAGTGTGGC TTGGAGGGAG
  888 AGGGAGAGCT CAGATTTTAG CTGACTCTGC TGGGCTAGAG GTTAGGCCTC AAGATCCAAC
  948 AGGGAGCACC AGGGTGCCCA CCTGCCAGGC CTAGAATCTG CCTTCTGGAC TGTTCTGCGC
 1008 ATATCACTGT GAAACTTGCC AGGTGTTTCA GGCAGCTTTG AGAGGCAGGC TGTTTGCAGT
```

Fig. 2

```
1068 TTCTTATGAA CAGTCAAGTC TTGTACACAG GGAAGGAAAA ATAAACCTGT TTAGAAGACA
1128 TAATTGAGAC ATGTCCCTGT TTTTATTACA GTGGCAATGA GGATGACTTG TTCTTTGAAG
1188 CTGATGGCCC TAAACAGATG AAGGTAAGAC TATGGGTTTA ACTCCCAACC CAAGGAAGGG
1248 CTCTAACACA GGGAAAGCTC AAAGAAGGGA GTTCTGGGCC ACTTTGATGC CATGGTATTT
1308 TGTTTTAGAA AGACTTTAAC CTCTTCCAGT GAGACACAGG CTGCACCACT TGCTGACCTG
1368 GCCACTTGGT CATCATATCA CCACAGTCAC TCACTAACGT TGGTGGTGGT GGCCACACTT
1428 GGTGGTGACA GGGGAGGAGT AGTGATAATG TTCCCATTTC ATAGTAGGAA GACAACCAAG
1488 TCTTCAACAT AAATTTGATT ATCCTTTTAA GAGATGGATT CAGCCTATGC CAATCACTTG
1548 AGTTAAACTC TGAAACCAAG AGATGATCTT GAGAACTAAC ATATGTCTAC CCCTTTTGAG
1608 TAGAATAGTT TTTTGCTACC TGGGGTGAAG CTTATAACAA CAAGACATAG ATGATATAAA
1668 CAAAAAGATG AATTGAGACT TGAAAGAAAA CCATTCACTT GCTGTTTGAC CTTGACAAGT
1728 CATTTTACCC GCTTTGGACC TCATCTGAAA AATAAAGGGC TGAGCTGGAT GATCTCTGAG
1788 ATTCCAGCAT CCTGCAACCT CCAGTTCTGA AATATTTTCA GTTGTAGCTA AGGGCATTTG
1848 GGCAGCAAAT GGTCATTTTT CAGACTCATC CTTACAAAGA GCCATGTTAT ATTCCTGCTG
1908 TCCCTTCTGT TTTATATGAT GCTCAGTAGC CTTCCTAGGT GCCCAGCCAT CAGCCTAGCT
1968 AGGTCAGTTG TGCAGGTTGG AGGCAGCCAC TTTTCTCTGG CTTTATTTTA TTCCAGTTTG
2028 TGATAGCCTC CCCTAGCCTC ATAATCCAGT CCTCAATCTT GTTAAAAACA TATTTCTTTA
2088 GAAGTTTTAA GACTGGCATA ACTTCTTGGC TGCAGCTGTG GGAGGAGCCC ATTGGCTTGT
2148 CTGCCTGGCC TTTGCCCCCC ATTGCCTCTT CCAGCAGCTT GGCTCTGCTC CAGGCAGGAA
2208 ATTCTCTCCT GCTCAACTTT CTTTTGTGCA CTTACAGGTC TCTTTAACTG TCTTTCAAGC
2268 CTTTGAACCA TTATCAGCCT TAAGGCAACC TCAGTGAAGC CTTAATACGG AGCTTCTCTG
2328 AATAAGAGGA AAGTGGTAAC ATTTCACAAA AAGTACTCTC ACAGGATTTG CAGAATGCCT
2388 ATGAGACAGT GTTATGAAAA AGGAAAAAAA AGAACAGTGT AGAAAAATTG AATACTTGCT
2448 GAGTGAGCAT AGGTGAATGG AAAATGTTAT GGTCATCTGC ATGAAAAAGC AAATCATAGT
2508 GTGACAGCAT TAGGGATACA AAAAGATATA GAGAAGGTAT ACATGTATGG TGTAGGTGGG
2568 GCATGTACAA AAAGATGACA AGTAGAATCG GGATTTATTC TAAAGAATAG CCTGTAAGGT
2628 GTCCAGAAGC CACATTCTAG TCTTGAGTCT GCCTCTACCT GCTGTGTGCC CTTGAGTACA
2688 CCCTTAACCT CCTTGAGCTT CAGAGAGGGA TAATCTTTTT ATTTTATTTT ATTTTATTTT
2748 GTTTTGTTTT GTTTTGTTTT GTTTTATGAG ACAGAGTCTC ACTCTGTTGC CCAGGCTGGA
2808 GTGCAGTGGT ACAATCTTGG CTTACTGCAT CCTCCACCTC CTGAGTTCAA GCGATTCTCC
2868 TTCCTCAGTC TCCTGAATAG CTAGGATTAC AGGTGCACCC CACCACACCC AGCTAATTTT
2928 TGTATTTTTA GTAGAGAAGG GGTTTCGCCA TGTTGGCCAG GCTGGTTTTG AAGTCCTGAC
2988 CTAAATGATT CATCCACCTC GGCTTCCCAA AGTGCTGGGA TTACAGGCAT GAGCCACCAC
3048 GCCTGGCCCA GAGAGGGATG ATCTTTAGAA GCTCGGGATT CTTTCAAGCC CTTTCCTCCT
3108 CTCTGAGCTT TCTACTCTCT GATGTCAAAG CATGGTTCCT GGCAGGACCA CCTCACCAGG
3168 CTCCCTCCCT CGCTCTCTCC GCAGTGCTCC TTCCAGGACC TGGACCTCTG CCCTCTGGAT
3228 GGCGGCATCC AGCTACGAAT CTCCGACCAC CACTACAGCA AGGGCTTCAG GCAGGCCGCG
3288 TCAGTTGTTG TGGCCATGGA CAAGCTGAGG AAGATGCTGG TTCCCTGCCC ACAGACCTTC
3348 CAGGAGAATG ACCTGAGCAC CTTCTTTCCC TTCATCTTTG AAGAAGGTAG TTAGCCAAGA
3408 GCAGGCAGTA GATCTCCACT TGTGTCCTCT TGGAAGTCAT CAAGCCCCAG CCAACTCAAT
3468 TCCCCCAGAG CCAAAGCCCT TTAAAGGTAG AAGGCCCAGC GGGGAGACAA AACAAAGAAG
3528 GCTGGAAACC AAAGCAATCA TCTCTTTAGT GGAAACTATT CTTAAAGAAG ATCTTGATGG
3588 CTACTGACAT TTGCAACTCC CTCACTCTTT CTCAGGGGCC TTTCACTTAC ATTGTCACCA
3648 GAGGTTCGTA ACCTCCCTGT GGGCTAGTGT TATGACCATC ACCATTTTAC CTAAGTAGCT
3708 CTGTTGCTCG GCCACAGTGA GCAGTAATAG ACCTGAAGCT GGAACCCATG TCTAATAGTG
3768 TCAGGTCCAG TGTTCTTAGC CACCCCACTC CCAGCTTCAT CCCTACTGGT GTTGTCATCA
3828 GACTTTGACC GTATATGCTC AGGTGTCCTC CAAGAAATCA AATTTTGCCA CCTCGCCTCA
3888 CGAGGCCTGC CCTTCTGATT TTATACCTAA ACAACATGTG CTCCACATTT CAGAACCTAT
3948 CTTCTTCGAC ACATGGGATA ACGAGGCTTA TGTGCACGAT GCACCTGTAC GATCACTGAA
4008 CTGCACGCTC CGGGACTCAC AGCAAAAAAG CTTGGTGATG TCTGGTCCAT ATGAACTGAA
4068 AGCTCTCCAC CTCCAGGGAC AGGATATGGA GCAACAAGGT AAATGGAAAC ATCCTGGTTT
4128 CCCTGCCTGG CCTCCTGGCA GCTTGCTAAT TCTCCATGTT TTAAACAAAG TAGAAAGTTA
4188 ATTTAAGGCA AATGATCAAC ACAAGTGAAA AAAATATTA AAAGGAATA TACAAACTTT
```

Fig. 2 (cont.)

```
4248 GGTCCTAGAA ATGGCACATT TGATTGCACT GGCCAGTGCA TTTGTTAACA GGAGTGTGAC
4308 CCTGAGAAAT TAGACGGCTC AAGCACTCCC AGGACCATGT CCACCCAAGT CTCTTGGGCA
4368 TAGTGCAGTG TCAATTCTTC CACAATATGG GGTCATTTGA TGGACATGGC CTAACTGCCT
4428 GTGGGTTCTC TCTTCCTGTT GTTGAGGCTG AAACAAGAGT GCTGGAGCGA TAATGTGTCC
4488 ATCCCCCTCC CCAGTCTTCC CCCCTTGCCC CAACATCCGT CCCACCCAAT GCCAGGTGGT
4548 TCCTTGTAGG GAAATTTTAC CGCCCAGCAG GAACTTATAT CTCTCCGCTG TAACGGGCAA
4608 AAGTTTCAAG TGCGGTGAAC CCATCATTAG CTGTGGTGAT CTGCCTGGCA TCGTGCCACA
4668 GTAGCCAAAG CCTCTGCACA GGAGTGTGGG CAACTAAGGC TGCTGACTTT GAAGGACAGC
4728 CTCACTCAGG GGGAAGCTAT TTGCTCTCAG CCAGGCCAAG AAAATCCTGT TTCTTTGGAA
4788 TCGGGTAGTA AGAGTGATCC CAGGGCCTCC AATTGACACT GCTGTGACTG AGGAAGATCA
4848 AAATGAGTGT CTCTCTTTGG AGCCACTTTC CCAGCTCAGC CTCTCCTCTC CCAGTTTCTT
4908 CCCATGGGCT ACTCTCTGTT CCTGAAACAG TTCTGGTGCC TGATTTCTGG CAGAAGTACA
4968 GCTTCACCTC TTTCCTTTCC TTCCACATTG ATCAAGTTGT TCCGCTCCTG TGGATGGGCA
5028 CATTGCCAGC CAGTGACACA ATGGCTTCCT TCCTTCCTTC CTTCAGCATT TAAAATGTAG
5088 ACCCTCTTTC ATTCTCCGTT CCTACTGCTA TGAGGCTCTG AGAAACCCTC AGGCCTTTGA
5148 GGGGAAACCC TAAATCAACA AAATGACCCT GCTATTGTCT GTGAGAAGTC AAGTTATCCT
5208 GTGTCTTAGG CCAAGGAACC TCACTGTGGG TTCCCACAGA GGCTACCAAT TACATGTATC
5268 CTACTCTCGG GGCTAGGGGT TGGGGTGACC CTGCATGCTG TGTCCCTAAC CACAAGACCC
5328 CCTTCTTTCT TCAGTGGTGT TCTCCATGTC CTTTGTACAA GGAGAAGAAA GTAATGACAA
5388 AATACCTGTG GCCTTGGGCC TCAAGGAAAA GAATCTGTAC CTGTCCTGCG TGTTGAAAGA
5448 TGATAAGCCC ACTCTACAGC TGGAGGTAAG TGAATGCTAT GGAATGAAGC CCTTCTCAGC
5508 CTCCTGCTAC CACTTATTCC CAGACAATTC ACCTTCTCCC CGCCCCCATC CCTAGGAAAA
5568 GCTGGGAACA GGTCTATTTG ACAAGTTTTG CATTAATGTA AATAAATTTA ACATAATTTT
5628 TAACTGCGTG CAACCTTCAA TCCTGCTGCA GAAAATTAAA TCATTTTGCC GATGTTATTA
5688 TGTCCTACCA TAGTTACAAC CCCAACAGAT TATATATTGT TAGGGCTGCT CTCATTTGAT
5748 AGACACCTTG GGAAATAGAT GACTTAAAGG GTCCCATTAT CACGTCCACT CCACTCCCAA
5808 AATCACCACC ACTATCACCT CCAGCTTTCT CAGCAAAAGC TTCATTTCCA AGTTGATGTC
5868 ATTCTAGGAC CATAAGGAAA AATACAATAA AAAGCCCCTG GAAACTAGGT ACTTCAAGAA
5928 GCTCTAGCTT AATTTTCACC CCCCCAAAAA AAAAAAATTC TCACCTACAT TATGCTCCTC
5988 AGCATTTGGC ACTAAGTTTT AGAAAAGAAG AAGGGCTCTT TTAATAATCA CACAGAAAGT
6048 TGGGGGCCCA GTTACAACTC AGGAGTCTGG CTCCTGATCA TGTGACCTGC TCGTCAGTTT
6108 CCTTTCTGGC CAACCCAAAG AACATCTTTC CCATAGGCAT CTTTGTCCCT TGCCCCACAA
6168 AAATTCTTCT TTCTCTTTCG CTGCAGAGTG TAGATCCCAA AAATTACCCA AGAAGAAGA
6228 TGGAAAAGCG ATTTGTCTTC AACAAGATAG AAATCAATAA CAAGCTGGAA TTTGAGTCTG
6288 CCCAGTTCCC CAACTGGTAC ATCAGCACCT CTCAAGCAGA AAACATGCCC GTCTTCCTGG
6348 GAGGGACCAA AGGCGGCCAG GATATAACTG ACTTCACCAT GCAATTTGTG TCTTCCTAAA
6408 GAGAGCTGTA CCCAGAGAGT CCTGTGCTGA ATGTGGACTC AATCCCTAGG GCTGGCAGAA
6468 AGGGAACAGA AAGGTTTTTG AGTACGGCTA TAGCCTGGAC TTTCCTGTTG TCTACACCAA
6528 TGCCCAACTG CCTGCCTTAG GGTAGTGCTA AGAGGATCTC CTGTCCATCA GCCAGGACAG
6588 TCAGCTCTCT CCTTTCAGGG CCAATCCCCA GCCCTTTTGT TGAGCCAGGC CTCTCTCACC
6648 TCTCCTACTC ACTTAAAGCC CGCCTGACAG AAACCACGGC CACATTTGGT TCTAAGAAAC
6708 CCTCTGTCAT-TCGCTCCCAC ATTCTGATGA GCAACCGCTT CCCTATTTAT TTATTTATTT
6768 GTTTGTTTGT TTTGATTCAT TGGTCTAATT TATTCAAAGG GGGCAAGAAG TAGCAGTGTC
6828 TGTAAAAGAG CCTAGTTTTT AATAGCTATG GAATCAATTC AATTTGGACT GGTGTGCTCT
6888 CTTTAAATCA AGTCCTTTAA TTAAGACTGA AAATATATAA GCTCAGATTA TTTAAATGGG
6948 AATATTTATA AATGAGCAAA TATCATACTG TTCAATGGTT CTGAAATAAA CTTCACTGAA
7008 GAAAAAAAAA AAAGGGTCTC TCCTGATCAT TGACTGTCTG GATTGACACT GACAGTAAGC
7068 AAACAGGCTG TGAGAGTTCT TGGGACTAAG CCCACTCCTC ATTGCTGAGT GCTGCAAGTA
7128 CCTAGAAATA TCCTTGGCCA CCGAAGACTA TCCTCCTCAC CCATCCCCTT TATTTCGTTG
7188 TTCAACAGAA GGATATTCAG TGCACATCTG GAACAGGATC AGCTGAAGCA CTGCAGGGAG
7248 TCAGGACTGG TAGTAACAGC TACCATGATT TATCTATCAA TGCACCAAAC ATCTGTTGAG
7308 CAAGCGCTAT GTACTAGGAG CTGGGAGTAC AGAGATGAGA ACAGTCACAA GTCCCTCCTC
7368 AGATAGGAGA GGCAGCTAGT TATAAGCAGA ACAAGGTAAC ATGACAAGTA GAGTAAGATA
```

Fig. 2 (cont.)

```
7428 GAAGAACGAA GAGGAGTAGC CAGGAAGGAG GGAGGAGAAC GACATAAGAA TCAAGCCTAA
7488 AGGGATAAAC AGAAGATTTC CACACATGGG CTGGGCCAAT TGGGTGTCGG TTACGCCTGT
7548 AATCCCAGCA CTTTGGGTGG CAGGGGCAGA AGATCGCTT GAGCCCAGGA GTTCAAGACC
7608 AGCCTGGGCA ACATAGTGAG ACTCCCATCT CTACAAAAAA TAAATAAATA AATAAAACAA
7668 TCAGCCAGGC ATGCTGGCAT GCACCTGTAG TCCTAGCTAC TTGGGAAGCT GACACTGGAG
7728 GATTGCTTGA GCCCAGAAGT TCAAGACTGC AGTGAGCTTA TCCGTTGACC TGCAGGTCGA
7788 C
```

Fig. 2 (cont.)

```
-5988 GTCGACCTGC AGGTCAACGG ATCTGAGAGG AGAGTAGCTT CTTGTAGATA ACAGTTGGAT
-5928 TATATACCAT GTCCTGATCC CCTTCATCAT CCAGGAGAGC AGAGGTGGTC ACCCTGATAG
-5868 CAGCAAGCCT GGGGGCTGCA GCTTGGTGGG TAGAGGTACT CAGGGGTACA GATGTCTCCA
-5808 AACCTGTCCT GCTGCCTTAG GGAGCTTCTA ATAAGTTGAT GGATTTGGTT AAAATTAACT
-5748 TGGCTACTTG GCAGGACTGG GTCAGTGAGG ACCAACAAAA AGAAGACATC AGATTATACC
-5688 CTGGGGGTTT GTATTTCTTG TGTTTCTTTC TCTTCTTTGT ACTAAAATAT TTACCCATGA
-5628 CTGGGAAAGA GCAACTGGAG TCTTTGTAGC ATTATCTTAG CAAAAATTTA CAAAGTTTGG
-5568 AAAACAATAT TGCCCATATT GTGTGGTGTG TCCTGTGACA CTCAGGATTC AAGTGTTGGC
-5508 CGAAGCCACT AAATGTGAGA TGAAGCCATT ACAAGGCAGT GTGCACATCT GTCCACCCAA
-5448 GCTGGATGCC AACATTTCAC AAATAGTGCT TGCGTGACAC AAATGCAGTT CCAGGAGGCC
-5388 CAAATGAAAA TGTTTGTACT GAAATTTGTT AAAGCTTCCC GACAAACTAG ATTTATCAGT
-5328 AAGGATTGTT TTCTGCAAGG GGGATGAAAC TTGTGGGGTG AGCCATTTGG GCTGAGGAGG
-5268 AGGGAGGTTG GAGCTGAGAA ATGTGGAGAC AATTTCCCTT TAGAAGGACT GAATCTCCCT
-5208 GCCTCTCTGG GGTGCGGCAG CCAGCAGGAT CCAATGGTGT ATATGTCTCC CCAGCTCCCC
-5148 ATTCAGTGAT ATCATGTCAG TAGCTTGAAA TTATCCGTGG TGGGAGTATT ATGTCATGGA
-5088 AATTGGCAAA TGGAAACTTT TATTGGAGAT TCAATTGTTA AACTTTTACC AGCACAACAC
-5028 TGCCCTGCCT TCAGAGTCAA TGACCCTATC CAAGTTTAAT CCATCTGTCC ACTGTCTCCA
-4968 ACACGATCTT TATAAAACAC ACCTGACAAC ATTACCCTTT TATTCAGTTT TTTAAAAGAT
-4908 AAGTTTCCAG CTCATCGGGG TGGCTTTAAA GGCCATTTCT CCTCTGGACC TCACCCAACT
-4848 TTTCAAATCA CTTTTCCTAC CCCTACCTCT AAATGCTACT CAAACTCCAG CCATCCTGAA
-4788 TAATAAGACT TTTGAAAAGT AGATTATGGG CTGGGCACAG TGGCTCACAC CTGTAATCCC
-4728 AGCACTTTGG GAGGCCAAGA TGGGTGGATC ACCTGAGGTC GGGAGTTCGA GACCAGCCTG
-4668 ACTAACATAG TGAAACCCTG TCTCTACTAA AAATACAAAA TTAGTTGGGG GTGGTGGCAC
-4608 AAGCCTGTAA TCCCAGCTAC TCAGGAGGTT GAGGCAGGGG AATTGCTTGA ACCTGGGAGG
-4548 CGGAGGTTGC GGTGAGCCTA GATTGCTCCA CTGCACTCCA GCCTGGGCAA CAAGAGCGAA
-4488 ACTCCATCTC AAAAAAATAA ATAAATAAAT AAAGTAGATT ACATCAGATA CCTCTGGCCT
-4428 AGGTTGTTTA TGACCAACTC TCCTGCTGAG AATAACTAGA AAAGCTAGAC AAAACATATT
-4368 TCCAAAAGAT CTCTTTGGAG GCATCAGAGA ATGGCCAAGG CTGTAAGGAA CTGCCTGAGC
-4308 CCAGAGAGGT GGAGCCCAGC ACTGGTGCCC TTTACTCCTG GGGACATGTG CTGGTTTCAA
-4248 AAACTTCAGC TGAGCTTTTG AGCATTCATG GAACTTGGTG GGGGAGATGA AATTTGTACC
-4188 TTAAATCCTG CCTACAGGGA GGGTCCCTGA TAATCCCCAC CCAATTTGGA AATCTGGGTC
-4128 AGCCTTCACA GGTACTGAAG CCCTCCTCTG AATGATCTCA AGTCCTGCTA GGGTAGAGGT
-4068 TACCTGCTTT TGAAAGGCTC CTGGCCTACC TGTGCAGCAG GAGCAAAAGT GAACCATCTC
-4008 AGGGTACAGA TAACAATCAT CCAGAGCCTT GAATGACCTC TACTGTGCTT AATATATAGT
-3948 ATTCAGCAGT CAGTAAAAAG GATTTAGGCA CATGCAAGAT GACCTGTGTA TCAGGGAGAA
-3888 ATAGGCAATA AATTGAGATC CAGCAGGGAT TTGAATCATG GATTTGAATC AGGGGCAGCC
-3828 TTCGAAAGAA CTATGGAGAA TATACTCAGA TTTAAAACAT AAGATTGGAA TTTTTGGCAG
-3768 AGAACTAACA ACTGTACAAA AAAGGAACCA AATGGAAATC CTAGAACTGA AAGATGCAAT
-3708 TAACCGATGT TGAGAAATAG CCAACATCTA TTGAACACTT CCCATGTGGA CAGCTGTGCT
-3648 AAACACTTTA CAGGCATCAA CATAAGATGT GTCCCCTTAC AGCAGTGCAG TGTCCCTCCT
-3588 AAGACATGGA CAGCCTGGTT TCCCTATCTC TCTGCTTCAT CAAAACCCCT TTACGTGGGG
-3528 CTTAGACACT CCTGTTGTCT CTAGTGTCTA GTAGCACAGG GCTCAGCACA TGGAAGCCAC
-3468 TAGATACAAT TTGATGACCA GGACCTCCGA TGAAAGCCAT GGGTGCTGAT GGGAAGGCA
-3408 TTGTCTTTTA TGTGCTATGG TCTTAAAGCT TCATCCAGGA AGCAGAACTC GGGGGGTGCT
-3348 GAGGACCCAG AACCGAGAAT AAGATTAGTC AGAGATTTCC TGTGGGCAGA AATCATAAGG
-3288 ACGCCAACTG TTTGGGTGAG ATAAGACGAA ACCAAGAGTG GACTTGTGGC CAGAAGCGTG
-3228 AGGAAGAGGG AGAGAGCTTC CCTTGTCCCC TTTCTTCCTC TCCCTAAGCC ACAGTGATTG
-3168 ACAGCCCCCC CGCTTTGGAG TCAGAGCAGG CTTGAGACTG GACTGGGAAA GGAGGGTGGG
-3108 TCAGGATACA GAGCAGGAAG GCTGGGAGTG CAGGGCAGGA GCAAGGGGCT GGGGCATTCA
-3048 TTGTGCCTGA TCTCTCCCAC TTTACCTGGG GTAAAGAAGC ATATGCAAAA GCCACGGTGT
```

Fig. 3

```
-2988 GAGTATTTCC CAAGTGCCAG GGTCAGGGCA TGATTCATCA CGTGCAGCAT TTCATTCAAT
-2928 CCTTATAGTA ACCGATGATG TGGCTTCTAT TATTAGCTCT ATCAGATAAT GAAACTGAGA
-2868 CCAAGACAGG CTCTGCACAT TGTGTGGGGT AATGACACAG GGGGATTCAG ACCTAGACTC
-2808 CATAACTCCT GCCCCAGGGA CCACCCCCAC CCTCACCCTG TGCATGTCGA CAAAGGACAG
-2748 ACTGGGCCAC TTCTCAGGAC ACAGCGGGGA AATGACACAG AGCAGGGAGG TTCCAGGAGC
-2688 CCCGAGCGTC TTTTCTCCAG GAGAATACTC TCTGAATTCA GACTGGGGTC AGAGAAACAT
-2628 TTACCCAGGA GCCGCAGTGT GGGTGGGGCT TTTTACTTGA AACGCTGTCT GAAGGCAGTG
-2568 GCAGGATGAA CTCTCCACCC TACCTTGGCA AGCCACTTCT CTTCTGCAAT CTGTAAGGAC
-2508 ATTGTTGAGA GAATTATGGT CTTCCAATTC GGGAGGGTTG AAGAAAGACA AATAGGAGAG
-2448 AACCTATCAT AGTCAGGTGC TAGCTGCCTT CTCTTTCAGA GAGTGTGAGA ATAAAGTGAT
-2388 ACACTTGATT ATTAGCAAAT ACTTTGGAAA TTTTAAACGC TAATATTCAA CACACTCTGG
-2328 AAGAGGCAAA TAAGTAGACA GGTTCATATA CATCATCTCC TTCAGCTAGT CCTCACAAAA
-2268 ACAAACAAAT GAATAAACAA AATTCTTCTT TGGCCCTCAT AGGAAGACAC TGTTTCTTGA
-2208 ACGTGTTTCA AAAAGGATGG GTGACTCACT CAAGGTCACA CTGTTTATGA GGACAGTACA
-2148 GGAATACAGA CATGCCATTT TGCCTGAAAA AATCCATCAC CCAGGGAGGT GACACAATTT
-2088 TGCAGAAATG TTCTATTTCC TCTGAAGGAT ACATTCTTTA AACCTTTGGG AAATTCATTC
-2028 ATAGTCTTCC TCCTTTGAAG GATTACTCTC TGGACACAAA GTGTTTGATT CTGATTTGTT
-1968 GGTTGGAAGA TGTGTTGGTT GAGAGAAAGA TTCTGATTTG TTGGTTGAAA ATAGACTCAT
-1908 CAAGATCAAC TGCTGTAGTA GTAAATATTT TGACATTTTG TCTGTATTCC TGTGCTGCCC
-1848 TCACAAGCTG CATCACCTTG AGTGAGTCAT TCATACTTTT TTGTTTGTTT TTGTTTTGGA
-1788 GATGGAGTCT TACTCTGTTG CCTAGGCTGG AGTGCGGTGG CGTGATCTTG GCTCACTGCG
-1728 ACCTCCATCT CCTGGGTTCA AGTGATCCTC CTGCCTCAGC CTCCCGAGTA GCTGGGATTA
-1668 CAGGCACATG CCACCATCCC TGCTAATTTT TGCATTTTCA GTAGAGACGG AGTTTCACCA
-1608 TGTTGGTCAG GTTGGTCTTG AACTCCTGAC CTCAGGTGAT CCGCCCACCT CAGCCTCCCC
-1548 AAGTGCTGGG ATTACAGGTG TGAGCCACCG TGCCCAGCCC AGCCATCATT TTTGAAACAC
-1488 GTTTGAGAAA TAGTGTCTTC CTTTGAGGGC CAAGGAGACA TTTTTTTTGT TTATTTGTTT
-1428 GTTTTTGTGA GGACTAGCTG AAGGGGGTGA TGTATATTAA CCTGCCTACT TATTTGCCTC
-1368 TTCCCAGAGT GTGATGAATA TTAGGGTTTA AAGTTTCTGA AGCATTTGTT AATAAAGCCC
-1308 GGGGCTGGAG GTCAGAAGAC CTGGATTTCT CTGCATACTT TTGCCATCAG CAAGCTGTGT
-1248 GACCTTGGAC AGATCCCTTT TTTGTCTAAA TCTTTCTGAG TCTTCTTGAA AACAATGCCA
-1188 GGTTGGGACA GGATGATTGC CAAGCTCCCG TCCAGCTCTA AAACACTGCA ACGTATGCTT
-1128 CTGCACCAGC ACTGTCCATC CTGTAGATCA TGCAGAAATT CTCTTCAACT TTTTCCTACC
-1068 CATAAAATAG GAGCATGCTT ACCTTTTTCC TAATGTTCCA GGCCCCGGGT CTAGATATTG
-1008 TAAGTAAGGA AGTTAATGTG TATCAGAGCC CATTATGGGC CAGAAGTTCT CCTCTTCCTT
 -948 CCTACACCTG CTTCCTCCCT CCCTCCCTCC CTCTTTCCCT TCCTTCCTTC CATCCATTTG
 -888 TGAAGAAGAC ATGATCACCC TCATTCTGAG AGTGAAGAGA CAGAGGCTCA ACTAATGAAA
 -828 TGATTTGTTC AAGGTCACAC GGGTGGCACA AGGCAAGTGG CAGAGGTTGA ATTTAGACCC
 -768 ATTCCTGTCC AAATGCTGAG TTTATGTCAT CGTCCCGAGA CCATAACTTT AAAGATGTAA
 -708 GATAGTGGGA AAAGAGTTGA TTTCAAAGCA CCTCTCAGAA GGACTCACTT TACATCAGGG
 -648 GTCAGCAGAC TCAGGCCAAA TCCGGTCCAT TCCCCGCTTT TGCAAAGAAA GTTGTAGTGG
 -588 AACACAGCTA GGCTTATTGA TTTATGGATT GCCAACGTCC TTTTGTGAAA CAGACAGCTG
 -528 AGCTGAGTAA TCGTGGCGCA CAAAACCTAA AATATTTACT ATCTCGTCCT TTACAGAATG
 -468 TTTGCCAATC TATGGTCCGG AGTCCAAGGC TGTCCATTTT TCAAAGAACA CAAAGTGACA
 -408 TGAGACTGTC CCATGTGCAG GGAGCCCTAT CATTTTATTA TGAAAAAACG GCCTTTCTGC
 -348 TCAAATCTGT TTTTTAAAAA GTCAACAAAC AGACTCTGGG TACCTGTCAG GAACAGTAGG
 -288 GAGTTTGGTT TCCATTGTGC TCTTCTTCCC AGGAACTCAA TGAAGGGGAA ATAGAAATCT
 -228 TAATTTTGGG GAAATTGCAC AGGGGAAAAA GGGGAGGGAA TCAGTTACAA CACTCCATTG
 -168 CGACACTTAG TGGGGTTGAA AGTGACAACA GCAAGGGTTT CTCTTTTTGG AAATGCGAGG
 -108 AGGGTATTTC CGCTTCTCGC AGTGGGGCAG GGTGGCAGAC GCCTAGCTTG GGTGAGTGAC
  -48 TATTTCTTTA TAAACCACAA CTCTGGGCCC GCAATGGCAG TCCACTGCTT GCTGCAGTCA
   13 CAGAATGGAA ATCTGCAGAG GCCTCCGCAG TCACCTAATC ACTCTCCTCC TCTTCCTGTT
   73 CCATTCAGAG ACGATCTGCC GACCCTCTGG GAGAAAATCC AGCAAGATGC AAGCCTTCAG
  133 GTAAGGCTAC CCCAAGGAGG AGAAGGTGAG GGTGGATCAG CTGGAGACTG GAAACATATC
```

Fig. 3 (cont.)

```
 193 ACAGCTGCCA GGGCTGCCAG GCCAGAGGGC CTGAGAACTG GGTTTGGGCT GGAGAGGATG
 253 TCCATTATTC AAGAAAGAGG CTGTTACATG CATGGGCTTC AGGACTTGTG TTTCAAAATA
 313 TCCCAGATGT GGATAGTGCG ACCGGAGGGC TGTCTTACTT TCCCAGAGAC TCAGGAACCC
 373 AGTGAGTAAT AGATGCATGC CAAGGAGTGG GACTGCGATT CAGGCCTAGT TGAATGTGCT
 433 GACAGAGAAG CAGAGAGGGG CACCAGGGGC ACAGCCCGAA GGCCCAGACT GATATGGGCA
 493 AGGCCTGTCT GTGCTGACAT GTCGGAGGGT CCCACTCTCC AGGGACCTTG GTTTCCCCGT
 553 CTGTGACATC TGTGACATGA GAGTCACGAT AACTCCTTGT GTGCCTTACA GGGTTGTTGT
 613 GAAAATTAAA TGCACAGATA ATAGCGTAAC AGTATTCCGT GCATTGTAAA GAGCCTGAAA
 673 ACCATTATGA TTTGAAAATG GAATCGGCTT TGTGAGACCA TCACTATTGT AAAGATGTGA
 733 TGCTGATAGA AATGACAGGA CTGCTTGTGC ATGCCCTCTG CAGTGTGACA TTCCAGCAGT
 793 GAAATCATGT TGGGGTGACT TCTCCCCCAC TCTGACCTTT ATGTTTGTCT GGGCCGAGGC
 853 TGCAAGTCGG GCTCTGTGGG TGTATGAGTG ACAAGTCTCT CCCTTCCAGA TATGGGGACT
 913 GTCTGCTTCC CTAGGTTGCC CTCTCCTGCT CTGATCAGCT AGAAGCTCCA GGAGATCCTC
 973 CTGGAGGCCC CAGCAGGTGA TGTTTATCCC TCCAGACTGA GGCTAAATCT AGAAACTAGG
1033 ATAATCACAA ACAGGCCAAT GCTGCCATAT GCAAAGCACT TTGGTTTGCC TGGCCACCCC
1093 TCGTCGAGCA TGTGGGCTCT TCAGAGCACC TGATGAGGTG GGTACAGTTA GCCACACTTC
1153 ACAGGTGAAG AGGTGAGGCA CAGGTCCCAG GTCAGGCTGG CCGGAGCTCT GTTTATTACG
1213 TCTCACAGCT TTGAGTCCTG CTCTCAACCA GAGAGGCCCT TTACCAAGAA GAAAGGATTG
1273 GGACCCAGAA TCAGGTCACT GGCTGAGGTA GAGAGGAAGC CGGGTTGTTC CCAAGGGTAG
1333 CTGCTCCTGC AGGACTCTGA GCAGGTCACC AGCTAATGGA GGAAAGGCTC TAGGGAAAGA
1393 CCCTTCTGGT CTCAGACTCA GAGCGAGTTA GCTGCAAGGT GTTCCGTCTC TTGAAACTTC
1453 TACCTAGGTG CTATGGTAGC CACTAGTCTC AGGTGGCTAT TTAAATTTAT ACTTAAATGA
1513 ATGAAAATAG AAGAAAATTT AAAATCCAGA CCCTTGGTCA CACTATCCAC ATTTAAAGAG
1573 GTCAATAGCC ACATGTGGTT AGTGGCCACC CTATTGGGCA GTGCAGCTAC AGAACATTTT
1633 TGCATCCCAG AAAGTTCTTT TGGATGTTGC TGCTCTACAG CATGCTTTGC TGAAACAGAA
1693 GTGCCTTCCC TGGGAATCTC AGATGGGAAG CAAGTAAGGA GGGGAGTCAA ATGTGGGCTC
1753 ACTGCTCACC AGCTGTGAGG GTTGGGCCTG CCTCTTAACC ATTGTCAGCC TCAGTCTTCT
1813 CATCCATGCA TGCCGTGGGT ATACTAAAAT ACTATACCCC TGGAAGAGCT GGATGCAAAT
1873 TTGACAAGTT CTGGGGGACA CAGGAAGGTG CCAAGCACAA GGCTGGGCAC ATGGTGGCTG
1933 TGCACTACAG CTGAGTCCTT TTCCTTTTCA GAATCTGGGA TGTTAACCAG AAGACCTTCT
1993 ATCTGAGGAA CAACCAACTA GTTGCTGGAT ACTTGCAAGG ACCAAATGTC AATTTAGAAG
2053 GTGAGTGGTT GCCAGGAAAG CCAATGTATC TGGGCATCAC GTCACTTTGC CCGTCTGTCT
2113 GCAGCAGCAT GGCCTGCCTG CACAAACCCT AGGTGCAATG TCCTAATCCT TGTTGGGTCT
2173 TTGTATTCAA GTTTGAAGCT GGGAGGGCCT GGCTACTGAA GGGCACATAT GAGGGTAGCC
2233 TGAAGAGGGT GTGGAGAGGT AGAGTCTAGG TCAGAGGTCA GTGCCTATAG CAAGTGGTC
2293 CCAGGGCCAC AGCTGGGAAG GGCAAATACC AGAAGGCAAG GTTGACCATT CCCTTCCTCA
2353 AGTGCCTATT AAGGCTCCAT GTTCCTATGT TGTTCAAACC CTAACTCAAT CCCAAATTAA
2413 TCCACCATGT ATAAGGTTGA GCTATGTCTC TTATTCCTGG ACACCATACT CAGCCATATC
2473 TGGTCCACAC ATTAACAGCT GGATGACCTT GAAGAAGCTT CACCCACTCT GTTCCTCAGC
2533 TTTCCCTTCA GTGGGATGAT ATCAACTGGA CAACAGGATG TGCGATTCTT TTAGTTCCAG
2593 CCTTCCAGGA TGTTTTCACT CCCCTGTTTG TTGTTGTAGG ATGGTATTAC CTCCACCTTC
2653 CCACCTTCCC TATGCCCTGG TTCTGTCTCC TGTGCCTCGC TCTGAAAGTG GATGAGACCT
2713 ACAATTCCTG TCCTGGTAGT TCTCCTAATG AACACACTGA AGCACGAGGA AGCTGAGATT
2773 TTTGTTGCTA CATGAGAGCA TGGAGGCCTC TTAGGGAGAG AGGAGGTTCA GAGACTCCTA
2833 GGCTCCTGGT GGAGCCCCAC TCATGGCCTT GTTCATTTTC CCTGCCCCTC AGCAACACTC
2893 CTATTGACCT GGAGCACAGG TATCCTGGGG AAAGTGAGGG AAATATGGAC ATCACATGGA
2953 ACAACATCCA GGAGACTCAG GCCTCTAGGA GTAACTGGGT AGTGTGCATC CTGGGGAAAG
3013 TGAGGGAAAT ATGGACATCA CATGAACAA CATCCAGGAG ACTCAGGCCT CTAGGAGTAA
3073 CTGGGTAGTG TGCATCCTGG GGAAAGTGAG GGAAATATGG ACATCACATG GAACAACATC
3133 CAGGAGACTC AGGCCTCTAG GAGTAACTGG GTAGTGTGCA TCCTGGGGAA AGTGAGGGAA
3193 ATATGGACAT CACATGGAAC AACATCCAGG AGACTCAGGC CTCTAGGAGT AACTGGGTAG
3253 TGTGCTTGGT TTAATCTTCT ATTTACCTGC AGACCAGGAA GATGAGACCT CTCTGCCCTT
3313 CTGACCTCGG GATTTTAGTT TTGTGGGGAC CAGGGGAGAT AGAAAAATAC CCGGGGTCTC
```

Fig. 3 (cont.)

```
3373 TTCATTATTG CTGCTTCCTC TTCTATTAAC CTGACCCTCC CCTCTGTTCT TCCCCAGAAA
3433 AGATAGATGT GGTACCCATT GAGCCTCATG CTCTGTTCTT GGGAATCCAT GGAGGGAAGA
3493 TGTGCCTGTC CTGTGTCAAG TCTGGTGATG AGACCAGACT CCAGCTGGAG GTAAAAACAT
3553 GCTTTGGATC TCAAATCACC CCAAAACCCA GTGGCTTGAA ACAACCAAAA TTTTTTCTTA
3613 TGATTCTGTG GGTTGACCAG GATTAGCTGG GTAGTTCTGT TCCATGTGGT GGAACATGCT
3673 GGGGTCACTT TGGAAGCTGC ATTCAGCAGA GTGCCAGGCT TGCGCTGGGC ATCCAAGGTG
3733 GTCCCTCATC CTCCAGGCTC TCTTTCCATG TGATCTCTCA GTGTTTAAGA GTTAGTTGGA
3793 GCTTCCTTAC AGCATGGCGG CTGACTTCCA AAAGGGATTA TTCCAAAAAG AGCCTCAACA
3853 TGCAGGCGCT TATTATGACT TCTGCTTGCA TCATCCTATT GGCCAAAGCC AGTCACGTGG
3913 CTAAGTCTAG CCCCCTGTGA GAGGAGACTG CATAAGAGTG TGAACACCAG AGACACGGT
3973 CACTGGGGGC CACCACTGTA ACCATCTACC ACAGGACCTG AATCTCTGTG TGCTACTCCC
4033 TTGCTCAAGG GCCCCCCTAC CCACGCAGAC CTGCTGTCTT CTAGCAAAGC CCATCCTCAG
4093 GACCTTTCTC TTCCAATCCT TATTGACTCA AATTGATTAG TTGGTGCTCC ACCCAGAGCC
4153 CTGTGCTCCT TTATCTCATG TAATGTTAAT GGGTTTCCCA GCCCTGGGAA AACATGGCTT
4213 TGTCTCAGGG GCTTGCTGGA TGCAACCTTA ACCTCAATGT GAGTGGCCAT ACTGTGGCAC
4273 TGTCCCATCC CTCACCAGGG ACACTGTTCT GGAGGGTGAC TGCCTGTTCT GTGAGGAGTG
4333 GGGATGGCTA GGACATTGCA TGGAACACAC CACCACCCCA TCTTCTCAGA GCTCAAACCC
4393 TGACAGAACA CCAGCTCCAC AGGCCTTGGC TTCTGCTGAT GGTGCCGTGT ATTTACCAGA
4453 CTTAGTGGTC CAAGGCCAGA GTGGCAGATT TCCCAAAGTC AAGGTGTGAC AGTGGGACAG
4513 CCTCTTTGTG TCTTTGCTGT CCTAAGAAAC CTGGGCCAGG CCAGGCGCAG TGGCTCACGC
4573 CTTGTAATCC CAGCACTTTG AGAGGCCAAG GTGGGCAGAT CACGAGGTCA GGAGTTTGAG
4633 ACCAGCCTGG CCAACATTGG TGAAACCCTG TCTCTATTAA AAATAGAAAA CATTAGACAG
4693 GTGTGGTGGT GCATGCCTGT AATCCCAGCT ACTCAGGAGG CTGAGGCAGG AGAATCGCTT
4753 GAACCCAGGA GGTGGAGGTT GCAGTGAGCC GAGATTGTGC CACTGCACTC CAGCCTAGGC
4813 GACAGAGCAA GACTCCGTCT CGGGAAAATT AATTAATAAA TAAATAAACC TAGGTCCCAG
4873 AGTCCCACAG AATGGCAGAC AGGAGCACCT GGGGGCTTTT AGGGTATGGC ATTTCCCCTG
4933 TACTAACTCT GGGCTGTCCA GAGGCGATTT CATGGCGTGG AGTGGAGAGG GAGGCAGCAC
4993 AGGACTTCCT AGGCCTCAGC TCTCACCTGC CCATCTTTTG ATTTCCAGGC AGTTAACATC
5053 ACTGACCTGA GCGAGAACAG AAAGCAGGAC AAGCGCTTCG CCTTCATCCG CTCAGACAGT
5113 GGCCCCACCA CCAGTTTTGA GTCTGCCGCC TGCCCCGGTT GGTTCCTCTG CACAGCGATG
5173 GAAGCTGACC AGCCCGTCAG CCTCACCAAT ATGCCTGACG AAGGCGTCAT GGTCACCAAA
5233 TTCTACTTCC AGGAGGACGA GTAGTACTGC CCAGGCCTGC CTGTTCCCAT TCTTGCATGG
5293 CAAGGACTGC AGGGACTGCC AGTCCCCCTG CCCCAGGGCT CCCGGCTATG GGGCACTGA
5353 GGACCAGCCA TTGAGGGGTG GACCCTCAGA AGGCGTCACA CAACCTGGT CACAGGACTC
5413 TGCCTCCTCT TCAACTGACC AGCCTCCATG CTGCCTCCAG AATGGTCTTT CTAATGTGTG
5473 AATCAGAGCA CAGCAGCCCC TGCACAAAGC CCTTCCATGT CGCCTCTGCA TTCAGGATCA
5533 AACCCCGACC ACCTGCCCAA CCTGCTCTCC TCTTGCCACT GCCTCTTCCT CCCTCATTCC
5593 ACCTTCCCAT GCCCTGGATC CATCAGGCCA CTTGATGACC CCAACCAAG TGGCTCCCAC
5653 ACCCTGTTTT ACAAAAAAGA AAGACCAGT CCATGAGGGA GGTTTTAAG GGTTTGTGGA
5713 AAATGAAAAT TAGGATTTCA TGATTTTTTT TTTTCAGTCC CCGTGAAGGA GAGCCCTTCA
5773 TTTGGAGATT ATGTTCTTTC GGGGAGAGGC TGAGGACTTA AAATATTCCT GCATTTGTGA
5833 AATGATGGTG AAAGTAAGTG GTAGCTTTTC CCTTCTTTTT CTTCTTTTTT TGTGATGTCC
5893 CAACTTGTAA AAATTAAAAG TTATGGTACT ATGTTAGCCC CATAATTTTT TTTTTCCTTT
5953 TAAAACACTT CCATAATCTG GACTCCTCTG TCCAGGCACT GCTGCCCAGC CTCCAAGCTC
6013 CATCTCCACT CCAGATTTTT TACAGCTGCC TGCAGTACTT TACCTCCTAT CAGAAGTTTC
6073 TCAGCTCCCA AGGCTCTGAG CAAATGTGGC TCCTGGGGGT TCTTTCTTCC TCTGCTGAAG
6133 GAATAAATTG CTCCTTGACA TTGTAGAGCT TCTGGCACTT GGAGACTTGT ATGAAAGATG
6193 GCTGTGCCTC TGCCTGTCTC CCCACCAGGC TGGGAGCTCT GCAGAGCAGG AAACATGACT
6253 CGTATATGTC TCAGGTCCCT GCAGGCCAA GCACCTAGCC TCGCTCTTGG CAGGTACTCA
6313 GCGAATGAAT GCTGTATATG TTGGGTGCAA AGTTCCCTAC TTCCTGTGAC TTCAGCTCTG
6373 TTTTACAATA AAATCTTGAA AATGCCTATA TTGTTGACTA TGTCCTTGGC CTTGACAGGC
6433 TTTGGGTATA GAGTGCTGAG GAAACTGAAA GACCAATGTG TYTTYCTTAC CCCAGAGGCT
6493 GGCGCCTGGC CTCTTCTCTG AGAGTTCTTT TCTTCCTTCA GCCTCACTCT CCCTGGATAA
6553 CATGAGAGCA AATCTCTCTG CGGGG
```

Fig. 3 (cont.)

SEQUENCE LISTING

<160> NUMBER OF SEQ ID NOS: 29

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 1
atggttttag aaatcatcaa gcctagggca                                           30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
aatgaaagga ggggaggatg acagaaatgt                                           30

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
tggcattgat ctggttcatc                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
gtttaggaat cttcccactt                                                      20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
ctcaggtgtc ctcgaagaaa tcaaa                                                25

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6 gctttttgc tgtgagtccc g         21

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 7
ctcagcaaca ctcctat         17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 8
tcctggtctg cagctaa         17

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 9
ctatctgagg aacaaccaac tagtagc         27

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
taggacattg cacctagggt ttgt         24

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
atttttttat aaatcatcaa gcctagggca         30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
aattaaagga gggaagaatg acagaaatgt                                        30

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 13
aagcttgttc taccacctga actaggc                                           27

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
ttacatatga gccttccatg                                                   20

<210> SEQ ID NO 15
<211> LENGTH: 11970
<212> TYPE: DNA
<213> ORGANISM: Homo sapiens

<400> SEQUENCE: 15
aagcttctac cctagtctgg tgctacactt acattgctta catccaagtg tggttatttc     60
tgtggctcct gttataacta ttatagcacc aggtctatga ccaggagaat tagactggca    120
ttaaatcaga ataagagatt ttgcacctgc aatagacctt atgacaccta accaacccca    180
ttatttacaa ttaaacagga acagagggaa tactttatcc aactcacaca agctgttttc    240
ctcccagatc catgcttttt tgcgtttatt atttttttaga gatgggggct tcactatgtt    300
gcccacactg gactaaaact ctgggcctca agtgattgtc ctgcctcagc ctcctgaata    360
gctgggacta caggggcatg ccatcacacc tagttcattt cctctattta aaatatacat    420
ggcttaaact ccaactggga acccaaaaca ttcatttgct aagagtctgg tgttctacca    480
cctgaactag gctggccaca ggaattataa agctgagaa attctttaat aatagtaacc     540
aggcaacatc attgaaggct catatgtaaa aatccatgcc ttcctttctc ccaatctcca    600
ttcccaaact tagccactgg ttctggctga ggccttacgc atacctcccg gggcttgcac    660
acaccttctt ctacagaaga cacaccttgg gcatatccta cagaagacca ggcttctctc    720
tggtccttgg tagagggcta ctttactgta acagggccag ggtggagagt tctctcctga    780
agctccatcc cctctatagg aaatgtgttg acaatattca gaagagtaag aggatcaaga    840
cttctttgtg ctcaaatacc actgttctct tctctaccct gccctaacca ggagcttgtc    900
accccaaaact ctgaggtgat ttatgcctta atcaagcaaa cttccctctt cagaaaagat    960
ggctcatttt ccctcaaaag ttgccaggag ctgccaagta ttctgccaat tcaccctgga   1020
gcacaatcaa caaattcagc cagaacacaa ctacagctac tattagaact attattatta   1080
ataaattcct ctccaaatct agccccttga cttcggattt cacgatttct cccttcctcc   1140
tagaaacttg ataagtttcc cgcgcttccc tttttctaag actacatgtt tgtcatctta   1200
taaagcaaag gggtgaataa atgaaccaaa tcaataactt ctggaatatc tgcaaacaac   1260

| | |
|---|---|
| aataatatca gctatgccat ctttcactat tttagccagt atcgagttga atgaacatag | 1320 |
| aaaaatacaa aactgaattc ttccctgtaa attccccgtt ttgacgacgc acttgtagcc | 1380 |
| acgtagccac gcctacttaa gacaattaca aaaggcgaag aagactgact caggcttaag | 1440 |
| ctgccagcca gagagggagt catttcattg gcgtttgagt cagcaaaggt attgtcctca | 1500 |
| catctctggc tattaaagta ttttctgttg ttgttttttct ctttggctgt tttctctcac | 1560 |
| attgccttct ctaaagctac agtctctcct ttcttttctt gtccctccct ggtttggtat | 1620 |
| gtgacctaga attacagtca gatttcagaa atgattctc tcattttgct gataaggact | 1680 |
| gattcgtttt actgagggac ggcagaacta gtttcctatg agggcatggg tgaatacaac | 1740 |
| tgaggcttct catgggaggg aatctctact atccaaaatt attaggagaa aattgaaaat | 1800 |
| ttccaactct gtctctctct tacctctgtg taaggcaaat accttattct tgtggtgttt | 1860 |
| ttgtaacctc ttcaaacttt cattgattga atgcctgttc tggcaataca ttaggttggg | 1920 |
| cacataagga ataccaacat aaataaaaca ttctaaaaga agtttacgat ctaataaagg | 1980 |
| agacaggtac atagcaaact aattcaaagg agctagaaga tggagaaaat gctgaatgtg | 2040 |
| gactaagtca ttcaacaaag ttttcaggaa gcacaaagag gaggggctcc cctcacagat | 2100 |
| atctggatta gaggctggct gagctgatgg tggctggtgt tctctgttgc agaagtcaag | 2160 |
| atggccaaag ttccagacat gtttgaagac ctgaagaact gttacaggta aggaataaga | 2220 |
| tttatctctt gtgatttaat gagggtttca aggctcacca gaatccagct aggcataaca | 2280 |
| gtggccagca tgggggcagg ccggcagagg ttgtagagat gtgtactagt cctgaagtca | 2340 |
| gagcaggttc agagaagacc cagaaaaact aagcattcag catgttaaac tgagattaca | 2400 |
| ttggcaggga gaccgccatt ttagaaaaat tatttttgag gtctgctgag ccctacatga | 2460 |
| atatcagcat caacttagac acagcctctg ttgagatcac atgccctgat ataagaatgg | 2520 |
| gttttactgg tccattctca ggaaaacttg atctcattca ggaacaggaa atggctccac | 2580 |
| agcaagctgg gcatgtgaac tcacatatgc aggcaaatct cactcagatg tagaagaaag | 2640 |
| gtaaatgaac acaaagataa aattacggaa catattaaac taacatgatg tttccattat | 2700 |
| ctgtagtaaa tactaacaca aactaggctg tcaaaatttt gcctggatat tttactaagt | 2760 |
| ataaattatg aaatctgttt tagtgaatac atgaaagtaa tgtgtaacat ataatctatt | 2820 |
| tggttaaaat aaaaaggaag tgcttcaaaa cctttctttt ctctaaagga gcttaacatt | 2880 |
| cttccctgaa cttcaattaa agctcttcaa tttgttagcc aagtccaatt tttacagata | 2940 |
| aagcacaggt aaagctcaaa gcctgtcttg atgactacta attccagatt agtaagatat | 3000 |
| gaattactct acctatgtgt atgtgtagaa gtccttaaat ttcaaagatg acagtaatgg | 3060 |
| ccatgtgtat gtgtgtgacc cacaactatc atggtcatta agtacattg gccagagacc | 3120 |
| acatgaaata acaacaatta cattctcatc atcttatttt gacagtgaaa atgaagaaga | 3180 |
| cagttcctcc attgatcatc tgtctctgaa tcaggtaagc aaatgactgt aattctcatg | 3240 |
| ggactgctat tcttacacag tggtttcttc atccaaagag aacagcaatg acttgaatct | 3300 |
| taaatacttt tgttttaccc tcactagaga tccagagacc tgtctttcat tataagtgag | 3360 |
| accagctgcc tctctaaact aatagttgat gtgcattggc ttctcccaga acagagcaga | 3420 |
| actatcccaa atccctgaga actggagtct cctggggcag gcttcatcag gatgttagtt | 3480 |
| atgccatcct gagaaagccc cgcaggccgc ttcaccaggt gtctgtctcc taacgtgatg | 3540 |
| tgttgtggtt gtcttctctg acaccagcat cagaggttag agaaagtctc caaacatgaa | 3600 |
| gctgagagag aggaagcaag ccagctgaaa gtgagaagtc tacagccact catcaatctg | 3660 |

-continued

```
tgttattgtg tttggagacc acaaatagac actataagta ctgcctagta tgtcttcagt    3720
actggcttta aaagctgtcc ccaaaggagt atttctaaaa tattttgagc attgttaagc    3780
agatttttaa cctcctgaga gggaactaat tggaaagcta ccactcacta caatcattgt    3840
taacctattt agttacaaca tctcattttt gagcatgcaa ataaatgaaa aagtcttcct    3900
aaaaaaatca tcttttatc ctggaaggag gaaggaaggt gagacaaaag ggagagaggg     3960
agggaagcct aatgaaacac cagttaccta agaccagaat ggagatcctc ctcactacct    4020
ctgttgaata cagcacctac tgaaagaact ttcattccct gaccatgaac agcctctcag    4080
cttctgtttt ccttcctcac agaaatcctt ctatcatgta agctatggcc cactccatga    4140
aggctgcatg gatcaatctg tgtctctgag tatctctgaa acctctaaaa catccaagct    4200
taccttcaag gagagcatgg tggtagtagc aaccaacggg aaggttctga gaagagacg     4260
gttgagttta agccaatcca tcactgatga tgacctggag gccatcgcca atgactcaga    4320
ggaaggtaag gggtcaagca caataatatc tttcttttac agttttaagc aagtagggac    4380
agtagaattt aggggaaaat taaacgtgga gtcagaataa caagaagaca accaagcatt    4440
agtctggtaa ctatacagag gaaaattaat ttttatcctt ctccaggagg gagaaatgag    4500
cagtggcctg aatcgagaat acttgctcac agccattatt tcttagccat attgtaaagg    4560
tcgtgtgact tttagccttt caggagaaag cagtaataag accacttacg agctatgttc    4620
ctctcatact aactatgcct ccttggtcat gttacataat cttttcgtga ttcagtttcc    4680
tctactgtaa aatggagata atcagaatcc cccactcatt ggattgttgt aaagattaag    4740
agtctcaggc tttacagact gagctagctg ggccctcctg actgttataa agattaaatg    4800
agtcaacatc ccctaacttc tggactagaa taatgtctgg tacaaagtaa gcacccaata    4860
aatgttagct attactatca ttattattat tattttattt tttttttttg agatggagtc    4920
tggctctgtc acccaggctg gagtgcagtg gcacaatctc ggctcactgc aagctctgcc    4980
tcctgggttc atgccattct cctgcctcag cctcccgagt aagctgggaa tacaggcacc    5040
cgccactgtt cccggctaat ttttgtatt tttagtagag acggagtttc accgtggtct    5100
ccatctcctc gtgatccacc caccttggcc tcccaaagtg ccgggattac aggcgtgagc    5160
caccgcgccc ggcctattat tattattatt actactacta ctaccatatat gaatactacc    5220
agcaatacta atttattaat gactggatta tgtctaaacc tcacaagaat cctaccttct    5280
cattttacat aaaaggaaac taagctcatt gagataggta aactgcccaa tggcatacat    5340
ctgtaagtgg gagagcctca aatctaattc agttctacct gagtaaaaaa atcatggttt    5400
ctcctccatc cctttactgt acaagcctcc acatgaacta taaacccaat attcctgttt    5460
ttaagataat acctaagcaa taacgcatgt tcacctagaa ggttttaaaa tgtaacaaaa    5520
tataagaaaa taaaaatcac tcatatcgtc agtgagagtt tactactgcc agcactatgg    5580
tatgtttcct taaatctttt gctatacaca tacctacatg tgaacaaata tgtctaacat    5640
caagaccaca ctatttacaa ctttatatcc agcttttctt acttagcaat gtattgagga    5700
cattttagag tgcccgtttt tcaccattat aagcaatgca acaatgaaca tctgtataaa    5760
taaatattca tttctctcac cctttatttc cttagaatat attcctagaa gtagaatttc    5820
ccagagccat gaggatttgt gacgctattg atatgtgcca ctttgcactc tctgtgacat    5880
atataattat ttttaatgca ttcatttttt tctcagagtg cattcgtttg aaaacataga    5940
cgggaaatac tggtagtctt ccttgtcagt tagaaacacc caaacaatga aaaatgaaaa    6000
```

-continued

```
agttgcacaa atagtctcta aaaacaatga aactattgcc tgaggaattg aagtttaaaa      6060
agaagcacat aagcaacaac aaggataatc ctagaaaacc agttctgctg actgggtgat      6120
ttcacttctc tttgcttcct catctggatt ggaatattcc taataccccc tccagaacta      6180
ttttccctgt tgtactaga ctgtgtatat catctgtgtt tgtacataga cattaatctg       6240
cacttgtgat catggtttta gaaatcatca agcctaggtc atcacttttt agcttcctga      6300
gcaatgtgaa atacaacttt atgaggatca tcaaatacga attcatcctg aatgacgccc      6360
tcaatcaaag tataattcga gccaatgatc agtacctcac ggctgctgca ttacataatc      6420
tggatgaagc aggtacatta aaatggcacc agacatttct gtcatcctcc cctcctttca      6480
tttacttatt tatttatttc aatctttctg cttgcaaaaa acatacctct tcagagttct      6540
gggttgcaca attcttccag aatagcttga agcacagcac ccccataaaa atcccaagcc      6600
agggcagaag gttcaactaa atctggaagt tccacaagag agaagtttcc tatctttgag      6660
agtaaagggt tgtgcacaaa gctagctgat gtactacctc tttggttctt tcagacattc      6720
ttaccctcaa ttttaaaact gaggaaactg tcagacatat taaatgattt actcagattt      6780
acccagaagc caatgaagaa caatcactct cctttaaaaa gtctgttgat caaactcaca      6840
agtaacacca aaccaggaag atctttatta tctctgataa catatttgtg aggcaaaacc      6900
tccaataagc tacaaatatg gcttaaagga tgaagtttag tgtccaaaaa cttttatcac      6960
acacatccaa ttttcatggc ggacatgttt tagtttcaac agtatacata ttttcaaagg      7020
tccagagagg caattttgca ataaacaagc aagacttttt ctgattggat gcacttcagc      7080
taacatgctt tcaactctac atttacaaat tattttgtgt tctattttc tacttaatat       7140
tatttctgca attttcccaa tattgacatc gtgtatgtat ttgccatttt taatatcact      7200
agacaattca atcaggttgc tacgttggtc ccttgggttt actctaaata gcttgattgc      7260
aaatatcttt gtatatatta ttgttttttc tcctatcttg taatttcttt gagcacatcc      7320
caaagaggaa tgcctagatc aatgggcaca ataatttga cagctcttat taaacattat      7380
tctgtaagta aaaactgaac tacttttcag tatcactagc aacatatgag tgtatcagct      7440
tcctaaaccc ctccatgtta ggtcattatg aacttatgat ctaacaaatt acagggtctt      7500
atcccactaa tgaaattata agagattcaa cacttattca gccccgaagg attcattcaa      7560
cgtagaaaat tctaagaaca ttaaccaagt atttacctgc ctagtgagtg tggaagacat      7620
tgtgaaggac acaaagatgt atagaattcc attcctgact tccaggtatt tacaccatag      7680
gtggggacct aactacacac acacacacac acacacacac acacacacac accatgcaca      7740
cacaatctac atcaacactt gattttatac aaatacaatg aatttacttt cttttttggtt     7800
cttctcttca ccagtgaaat ttgacatggg tgcttataag tcatcaaagg atgatgctaa      7860
aattaccgtg attctaagaa tctcaaaaac tcaattgtat gtgactgccc aagatgaaga      7920
ccaaccagtg ctgctgaagg tcagttgtcc tttgtctcca acttaccttc atttacatct      7980
catatgtttg taaataagcc caataggcag acacctctaa caaggtgaca ctgtcctctt      8040
tccttcctac cacagccccc acctacccac cccactccca ttgattccag aggcgtgcct      8100
aggcaggatc tatgagaaaa tataacagag agtaagagga aaattacctt ctttcttttt      8160
cctttccctg cctgacctta ttcacctccc atcccagagc atccatttat tccattgatc      8220
tttactgaca tctattatct gacctacaca atactagaca ttaggacaat gtggcctgcc      8280
tccaagaaac tcaaataagc caactgagat cagagaggat taatcacctg ccaatgggca      8340
caaagcaaca agctgggagc caagtcccaa aatgggggcct gctgcttcca gttcccctct      8400
```

```
ctctgcattg atgtcagcat tatccttcgt cccagtcctg tctccactac cactttcccc    8460
ctcaaacaca cacacacaca acagccttag atgttttctc cactgataag taggtgactc    8520
aatttgtaag tatataatcc aagaccttct attcccaagt agaatttatg tgcctgcctg    8580
tgcttttcta cctggatcaa gtgatgtcta cagagtaggg cagtagcttc attcatgaac    8640
tcattcaaca agcattattc actgagagcc ttgtattttt caggcatagt gccaacagca    8700
gtgtggacag tggtgcatca aagcctctag tctcatagaa cttagtcttc tggaggatat    8760
ggaaaacaga caacccaaac aaccaacaaa agagcaagat gctgcaaaaa aaaaaaaaat    8820
gaatagggtg ctaagataga gaaaagtggg agagtgctat ttagacaaag tggtaaaaac    8880
aaagcccctt gtgagatgag agctgccgac agaggggcg gtcatggtt gtgggttttt       8940 gggtaggaca ttcagaggag ggggcgggtc gtggttgtgg gttttgggt aggacattca     9000 gaggaggggg cgggtcgtgg ttgtgggttt tgggtagga cattcagagg aggggcggg      9060 tcgtggttgt gggttttggg gtaggacatt cagaggaggg ggcgggtcgt ggttgtgggt    9120
ttttgggaca ttcagaggag tctgaatgca cccaggccta caacttcaag atggtaaagg    9180
acagctccaa ggatcagaag aagcattctt ggaactgggg cattttgaga aggaggaaaa    9240
atatgcagag actagtgctt gcagagcttg catttggatt tcatttgagg tacaatgaaa    9300
acccattaat gggtttcaca cagtgcaatg gcctgacctc acttatattt cctaaaatag    9360
aaaacagatc agaaggaagg caatagagaa gcagaaagtc caatgaggag gtttcacagc    9420
agtcatgggg gtggggtaag gaaaagaagt ggaaagaaac agacagaatt gggttatatt    9480
ttggagatag aaccaacaga aggaagagga gaaacaacat ttactgagaa gggaaaaagt    9540
aggagaggaa taggtttggg aaataaatcc tgctgacatt ggaaacccca aggaagcctc    9600
aaaagtatat ttacttgctt tagatttaaa agaataggaa agaagcatct caacttggaa    9660
tttgaaatct attttttccat aaaagtattg ttaaattcta ctcatactca caagaaaagt    9720
acattctaaa gagtatattg aaagagttta ctgatatact taggaatttt gtgtgtatgt    9780
gtgtgtgtgt atgtgtgtgt gtgtgtttaa ccttcaattg ttgacttaaa tactgagata    9840
aatgtcatct aaatgctaaa ttgatttccc aaaggtatga tttgttcact tggagatcaa    9900
aatgtttagg gggcttagaa tcactgtagt gctcagattt gatgcaaaat gtcttaggcc    9960
tatgttgaag gcaggacaga aacaatgttt ccctcctacc tgcctggata cagtaagata   10020
ctagtgtcac tgacaatctt cataactaat ttagatctct ctccaatcaa ctaaggaaat   10080
caactcttat taatagactg ggccacacat ctactaggca tgtaataaat gcttgctgaa   10140
tgaacaaatg aatgaagagc ctatagcatc atgttacagc catagtccta aagtggtgtt   10200
tctcatgaag gccaaatgct aagggattga gcttcagtcc tttttctaac atcttgttct   10260
ctaacagaat tctcttcttt tcttcatagg agatgcctga gatacccaaa accatcacag   10320
gtagtgagac caacctcctc ttccttctggg aaactcacgg cactaagaac tatttcacat   10380
cagttgccca tccaaacttg tttattgcca caaagcaaga ctactgggtg tgcttggcag   10440
gggggccacc ctctatcact gactttcaga tactggaaaa ccaggcgtag gtctggagtc   10500
tcacttgtct cacttgtgca gtgttgacag ttcatatgta ccatgtacat gaagaagcta   10560
aatcctttac tgttagtcat ttgctgagca tgtactgagc cttgtaattc taaatgaatg   10620 tttcacactct ttgtaagagt ggaaccaaca ctaacatata atgttgttat ttaaagaaca   10680
ccctatattt tgcatagtac caatcatttt aattattatt cttcataaca attttaggag   10740
```

-continued

```
gaccagagct actgactatg gctaccaaaa agactctacc catattacag atgggcaaat      10800
taaggcataa gaaaactaag aaatatgcac aatagcagtt gaaacaagaa gccacagacc      10860
taggatttca tgatttcatt tcaactgttt gccttctgct tttaagttgc tgatgaactc      10920
ttaatcaaat agcataagtt tctgggacct cagttttatc attttcaaaa tggagggaat      10980
aatacctaag ccttcctgcc gcaacagttt tttatgctaa tcagggaggt cattttggta      11040
aaatacttct cgaagccgag cctcaagatg aaggcaaagc acgaaatgtt attttttaat      11100
tattatttat atatgtattt ataaatatat ttaagtaat tataatatac tatatttatg      11160 ggaaccccctt catcctctga gtgtgaccag gcatcctcca caatagcaga cagtgttttc      11220
tgggataagt aagtttgatt tcattaatac agggcatttt ggtccaagtt gtgcttatcc      11280
catagccagg aaactctgca ttctagtact tgggagacct gtaatcatat aataaatgta      11340
cattaattac cttgagccag taattggtcc gatctttgac tcttttgcca ttaaacttac      11400 ctggcattc ttgtttcatt caattccacc tgcaatcaag tcctacaagc taaaattaga      11460
tgaactcaac tttgacaacc atgagaccac tgttatcaaa actttctttt ctggaatgta      11520
atcaatgttt cttctaggtt ctaaaaattg tgatcagacc ataatgttac attattatca      11580
acaatagtga ttgatagagt gttatcagtc ataactaaat aaagcttgca acaaaattct      11640
ctgacacata gttattcatt gccttaatca ttatttact gcatggtaat tagggacaaa      11700
tggtaaatgt ttacataaat aattgtattt agtgttactt tataaaatca accaagatt      11760 ttatattttt ttctcctctt tgttagctgc cagtatgcat aaatggcatt aagaatgata      11820
atatttccgg gttcacttaa agctcatatt acacatacac aaaacatgtg ttcccatctt      11880
tatacaaact cacacataca gagctacatt aaaaacaact aataggccag gcacggtggc      11940
tcagacctgt aatcccagca ctttgggagg                                      11970
```

<210> SEQ ID NO 16
<211> LENGTH: 9721
<212> TYPE: DNA
<213> ORGANISM: Homo sapiens
<220> FEATURE:
<221> NAME/KEY: modified_base
<222> LOCATION: (135)..(136)
<223> OTHER INFORMATION: a, t, c, g, other or unknown

<400> SEQUENCE: 16

```
agaaagaaag agagagagaa agaaaagaaa gaggaaggaa ggaaggaagg aagaaagaca       60
ggctctgagg aaggtggcag ttcctacaac gggagaacca gtggttaatt tgcaaagtgg      120
atcctgtgga ggcanncaga ggagtcccct aggccaccca gacagggctt ttagctatct      180
gcaggccaga caccaaattt caggagggct cagtgttagg aatggattat ggcttatcaa      240
attcacagga aactaacatg ttgaacagct tttagatttc ctgtggaaaa tataacttac      300
taaagatgga gttcttgtga ctgactcctg atatcaagat actgggagcc aaattaaaaa      360
tcagaaggct gctggagag caagtccatg aaatgctctt tttcccacag tagaacctat      420
ttccctcgtg tctcaaatac ttgcacagag gctcactccc ttggataatg cagagcgagc      480
acgatacctg gcacatacta atttgaataa aatgctgtca aattcccatt cacccattca      540
agcagcaaac tctatctcac ctgaatgtac atgccaggca ctgtgctaga cttggctcaa      600
aaagatttca gtttcctgga ggaaccagga gggcaaggtt tcaactcagt gctataagaa      660
gtgttacagg ctggacacgg tggctcacgc ctgtaatccc aacatttggg aggccgaggc      720
gggcagatca caaggtcagg agatcgagac catcctggct aacatggtga aaccctgtct      780
```

-continued

```
ctactaaaaa tacaaaaaat tagccgggcg ttggcggcag gtgcctgtag tcccagctgc    840
tggggaggct gaggcaggag aatggtgtga acccggagg cggaacttgc aggggccga      900 gatcgtgcca ctgcactcca gcctgggcga cagagtgaga ctctgtctca aaaaaaaaa     960 aaaagtgtta tgatgcagac ctgtcaaaga ggcaaaggag ggtgttccta cactccaggc   1020
actgttcata acctggactc tcattcattc tacaaatgga gggctcccct gggcagatcc   1080
ctggagcagg cactttgctg gtgtctcggt taaagagaaa ctgataactc ttggtattac   1140
caagagatag agtctcagat ggatattctt acagaaacaa tattcccact tttcagagtt   1200
caccaaaaaa tcattttagg cagagctcat ctggcattga tctggttcat ccatgagatt   1260
ggctagggta acagcacctg gtcttgcagg gttgtgtgag cttatctcca gggttgcccc   1320
aactccgtca ggagcctgaa ccctgcatac cgtatgttct ctgccccagc caagaaggt   1380 caattttctc ctcagaggct cctgcaattg acagagagct cccgaggcag agaacagcac   1440
ccaaggtaga gacccacacc tcaatacag acagggaggg ctattggccc ttcattgtac    1500
ccatttatcc atctgtaagt gggaagattc ctaaacttaa gtacaaagaa gtgaatgaag   1560
aaaagtatgt gcatgtataa atctgtgtgt cttccacttt gtcccacata tactaaattt   1620
aaacattctt ctaacgtggg aaaatccagt attttaatgt ggacatcaac tgcacaacga   1680
ttgtcaggaa aacaatgcat atttgcatgg tgatacattt gcaaaatgtg tcatagtttg   1740
ctactccttg cccttccatg aaccagagaa ttatctcagt ttattagtcc cctcccctaa   1800
gaagcttcca ccaatactct tttcccttt cctttaactt gattgtgaaa tcaggtattc    1860
aacagagaaa tttctcagcc tcctacttct gcttttgaaa gctataaaaa cagcgaggga   1920
gaaactggca gataccaaac ctcttcgagg cacaaggcac aacaggctgc tctgggattc   1980
tcttcagcca atcttcattg ctcaagtatg actttaatct tccttacaac taggtgctaa   2040
gggagtctct ctgtctctct gcctctttgt gtgtatgcat attctctctc tctctctctt   2100
tctttctctg tctctcctct ccttcctctc tgcctcctct ctcagctttt tgcaaaaatg   2160
ccaggtgtaa tataatgctt atgactcggg aaatattctg ggaatggata ctgcttatct   2220
aacagctgac accctaaagg ttagtgtcaa agcctctgct ccagctctcc tagccaatac   2280
attgctagtt gggtttggt ttagcaaatg cttttctcta gacccaaagg acttctcttt    2340
cacacattca ttcatttact cagagatcat ttctttgcat gactgccatg cactggatgc   2400
tgagagaaat cacacatgaa cgtagccgtc atggggaagt cactcatttt ctccttttta   2460
cacaggtgtc tgaagcagcc atggcagaag tacctgagct cgccagtgaa atgatggctt   2520
attacaggtc agtggagacg ctgagaccag taacatgagc aggtctcctc tttcaagagt   2580
agagtgttat ctgtgcttgg agaccagatt tttcccctaa attgcctctt tcagtggcaa   2640
acagggtgcc aagtaaatct gatttaaaga ctactttccc attacaagtc cctccagcct   2700
tgggacctgg aggctatcca gatgtgttgt gcaagggct tcctgcagag gcaaatgggg    2760
agaaaagatt ccaagcccac aatacaagga atccctttgc aaagtgtggc ttggagggag   2820
agggagagct cagattttag ctgactctgc tgggctagag gttaggcctc aagatccaac   2880
agggagcacc agggtgccca cctgccaggc ctagaatctg ccttctggac tgttctgcgc   2940
atatcactgt gaaacttgcc aggtgtttca ggcagctttg agaggcaggc tgtttgcagt   3000
ttcttatgaa cagtcaagtc ttgtacacag ggaaggaaaa ataaacctgt ttagaagaca   3060
taattgagac atgtccctgt ttttattaca gtggcaatga ggatgacttg ttctttgaag   3120
```

```
ctgatggccc taaacagatg aaggtaagac tatgggttta actcccaacc caaggaaggg    3180
ctctaacaca gggaaagctc aaagaaggga gttctgggcc actttgatgc catggtattt    3240
tgttttagaa agactttaac ctcttccagt gagacacagg ctgcaccact tgctgacctg    3300
gccacttggt catcatatca ccacagtcac tcactaacgt tggtggtggt ggccacactt    3360
ggtggtgaca ggggaggagt agtgataatg ttcccatttc atagtaggaa gacaaccaag    3420
tcttcaacat aaatttgatt atcctttaa gagatggatt cagcctatgc caatcacttg    3480
agttaaactc tgaaaccaag agatgatctt gagaactaac atatgtctac cccttttgag    3540
tagaatagtt ttttgctacc tggggtgaag cttataacaa caagacatag atgatataaa    3600 caaaagatg aattgagact tgaaagaaaa ccattcactt gctgtttgac cttgacaagt    3660
cattttaccc gctttggacc tcatctgaaa aataaagggc tgagctggat gatctctgag    3720
attccagcat cctgcaacct ccagttctga aatattttca gttgtagcta agggcatttg    3780
ggcagcaaat ggtcattttt cagactcatc cttacaaaga gccatgttat attcctgctg    3840
tcccttctgt tttatatgat gctcagtagc cttcctaggt gcccagccat cagcctagct    3900
aggtcagttg tgcaggttgg aggcagccac ttttctctgg ctttatttta ttccagtttg    3960
tgatagcctc ccctagcctc ataatccagt cctcaatctt gttaaaaaca tatttcttta    4020
gaagttttaa gactggcata acttcttggc tgcagctgtg ggaggagccc attggcttgt    4080
ctgcctggcc tttgcccccc attgcctctt ccagcagctt ggctctgctc caggcaggaa    4140
attctctcct gctcaacttt cttttgtgca cttacaggtc tctttaactg tctttcaagc    4200
ctttgaacca ttatcagcct taaggcaacc tcagtgaagc cttaatacgg agcttctctg    4260
aataagagga aagtggtaac atttcacaaa agtactctc acaggatttg cagaatgcct    4320
atgagacagt gttatgaaaa aggaaaaaaa agaacagtgt agaaaaattg aatacttgct    4380
gagtgagcat aggtgaatgg aaaatgttat ggtcatctgc atgaaaaagc aaatcatagt    4440
gtgacagcat tagggataca aaagatata gagaaggtat acatgtatgg tgtaggtggg    4500
gcatgtacaa aaagatgaca agtagaatcg ggatttattc taaagaatag cctgtaaggt    4560
gtccagaagc cacattctag tcttgagtct gcctctacct gctgtgtgcc cttgagtaca    4620
cccttaacct ccttgagctt cagagaggga taatcttttt attttatttt attttatttt    4680
gttttgtttt gttttgtttt gtttatgag acagagtctc actctgttgc ccaggctgga    4740
gtgcagtggt acaatcttgg cttactgcat cctccacctc ctgagttcaa gcgattctcc    4800
ttcctcagtc tcctgaatag ctaggattac aggtgcaccc caccacaccc agctaatttt    4860
tgtattttta gtagagaagg ggtttcgcca tgttggccag gctggttttg aagtcctgac    4920
ctaaatgatt catccacctc ggcttcccaa agtgctggga ttacaggcat gagccaccac    4980
gcctggccca gagagggatg atctttagaa gctcgggatt cttcaagcc ctttcctcct    5040 ctctgagctt tctactctct gatgtcaaag catggttcct ggcaggacca cctcaccagg    5100
ctccctccct cgctctctcc gcagtgctcc ttccaggacc tggacctctg ccctctggat    5160
ggcggcatcc agctacgaat ctccgaccac cactacagca agggcttcag gcaggccgcg    5220
tcagttgttg tggccatgga caagctgagg aagatgctgg ttccctgccc acagaccttc    5280
caggagaatg acctgagcac cttctttccc ttcatctttg aagaaggtag ttagccaaga    5340
gcaggcagta gatctccact tgtgtcctct tggaagtcat caagcccag ccaactcaat    5400 tcccccagag ccaaagccct ttaaaggtag aaggcccagc ggggagacaa aacaaagaag    5460
gctggaaacc aaagcaatca tctctttagt ggaaactatt cttaaagaag atcttgatgg    5520
```

```
ctactgacat ttgcaactcc ctcactcttt ctcaggggcc tttcacttac attgtcacca   5580
gaggttcgta acctccctgt gggctagtgt tatgaccatc accatttttac ctaagtagct   5640
ctgttgctcg gccacagtga gcagtaatag acctgaagct ggaacccatg tctaatagtg   5700
tcaggtccag tgttcttagc caccccactc ccagcttcat ccctactggt gttgtcatca   5760
gactttgacc gtatatgctc aggtgtcctc caagaaatca aattttgcca cctcgcctca   5820
cgaggcctgc ccttctgatt ttatacctaa acaacatgtg ctccacattt cagaacctat   5880
cttcttcgac acatgggata acgaggctta tgtgcacgat gcacctgtac gatcactgaa   5940
ctgcacgctc cgggactcac agcaaaaaag cttggtgatg tctggtccat atgaactgaa   6000
agctctccac ctccagggac aggatatgga gcaacaaggg aaatggaaac atcctggttt   6060
ccctgcctgg cctcctggca gcttgctaat tctccatgtt ttaaacaaag tagaaagtta   6120
atttaaggca aatgatcaac acaagtgaaa aaaatatta aaaaggaata tacaaacttt   6180
ggtcctagaa atggcacatt tgattgcact ggccagtgca tttgttaaca ggagtgtgac   6240
cctgagaaat tagacggctc aagcactccc aggaccatgt ccacccaagt ctcttgggca   6300
tagtgcagtg tcaattcttc cacaatatgg ggtcatttga tggacatggc ctaactgcct   6360
gtgggttctc tcttcctgtt gttgaggctg aaacaagagt gctggagcga taatgtgtcc   6420
atcccctcc ccagtcttcc ccccttgccc caacatccgt cccacccaat gccaggtggt   6480
tccttgtagg gaaattttac cgcccagcag gaacttatat ctctccgctg taacgggcaa   6540
aagtttcaag tgcggtgaac ccatcattag ctgtggtgat ctgcctggca tcgtgccaca   6600
gtagccaaag cctctgcaca ggagtgtggg caactaaggc tgctgactt gaaggacagc   6660
ctcactcagg gggaagctat tgctctcag ccaggccaag aaaatcctgt ttctttggaa   6720
tcgggtagta agagtgatcc cagggcctcc aattgacact gctgtgactg aggaagatca   6780
aaatgagtgt ctctctttgg agccactttc ccagctcagc ctctcctctc ccagtttctt   6840
cccatgggct actctctgtt cctgaaacag ttctggtgcc tgatttctgg cagaagtaca   6900
gcttcacctc tttcctttcc ttccacattg atcaagttgt tccgctcctg tggatgggca   6960
cattgccagc cagtgacaca atggcttcct tccttccttc cttcagcatt taaaatgtag   7020
accctctttc attctccgtt cctactgcta tgaggctctg agaaaccctc aggcctttga   7080
ggggaaaccc taaatcaaca aaatgaccct gctattgtct gtgagaagtc aagttatcct   7140
gtgtcttagg ccaaggaacc tcactgtggg ttcccacaga ggctaccaat tacatgtatc   7200
ctactctcgg ggctaggggt tggggtgacc ctgcatgctg tgtccctaac cacaagaccc   7260
ccttctttct tcagtggtgt tctccatgtc ctttgtacaa ggagaagaaa gtaatgacaa   7320
aatacctgtg gccttgggcc tcaaggaaaa gaatctgtac ctgtcctgcg tgttgaaaga   7380
tgataagccc actctacagc tggaggtaag tgaatgctat ggaatgaagc ccttctcagc   7440
ctcctgctac cacttattcc cagacaattc accttctccc cgcccccatc cctaggaaaa   7500
gctgggaaca ggtctatttg acaagttttg cattaatgta aataaattta acataatttt   7560
taactgcgtg caaccttcaa tcctgctgca gaaaattaaa tcattttgcc gatgttatta   7620
tgtcctacca tagttacaac cccaacagat tatatattgt tagggctgct ctcatttgat   7680
agacaccttg ggaaatagat gacttaaagg gtcccattat cacgtccact ccactcccaa   7740
aatcaccacc actatcacct ccagctttct cagcaaaagc ttcatttcca agttgatgtc   7800
attctaggac cataaggaaa aatacaataa aaagcccctg gaaactaggt acttcaagaa   7860
```

-continued

```
gctctagctt aattttcacc cccccaaaaa aaaaaaattc tcacctacat tatgctcctc      7920
agcatttggc actaagtttt agaaagaag aagggctctt ttaataatca cacagaaagt      7980
tgggggccca gttacaactc aggagtctgg ctcctgatca tgtgacctgc tcgtcagttt      8040
cctttctggc aacccaaag aacatctttc ccataggcat ctttgtccct tgccccacaa      8100
aaattcttct ttctctttcg ctgcagagtg tagatcccaa aaattccca agaagaaga      8160 tggaaaagcg atttgtcttc aacaagatag aaatcaataa caagctggaa tttgagtctg      8220
cccagttccc caactggtac atcagcacct ctcaagcaga aaacatgccc gtcttcctgg      8280
gagggaccaa aggcggccag gatataactg acttcaccat gcaatttgtg tcttcctaaa      8340
gagagctgta cccagagagt cctgtgctga atgtggactc aatccctagg ctggcagaa      8400 agggaacaga aaggttttg agtacggcta tagcctggac tttcctgttg tctacaccaa      8460
tgcccaactg cctgccttag ggtagtgcta agaggatctc ctgtccatca gccaggacag      8520
tcagctctct cctttcaggg ccaatcccca gccctttgt tgagccaggc ctctctcacc      8580
tctcctactc acttaaagcc cgcctgacag aaaccacggc cacatttggt tctaagaaac      8640
cctctgtcat tcgctcccac attctgatga gcaaccgctt ccctatttat ttatttattt      8700
gtttgtttgt tttgattcat tggtctaatt tattcaaagg gggcaagaag tagcagtgtc      8760
tgtaaaagag cctagttttt aatagctatg gaatcaattc aatttggact ggtgtgctct      8820
ctttaaatca agtcctttaa ttaagactga aaatatataa gctcagatta tttaaatggg      8880
aatatttata aatgagcaaa tatcatactg ttcaatggtt ctgaaataaa cttcactgaa      8940
gaaaaaaaaa aaagggtctc tcctgatcat tgactgtctg gattgacact gacagtaagc      9000
aaacaggctg tgagagttct tgggactaag cccactcctc attgctgagt gctgcaagta      9060
cctagaaata tccttggcca ccgaagacta tcctcctcac ccatcccctt tatttcgttg      9120
ttcaacagaa ggatattcag tgcacatctg aacaggatc agctgaagca ctgcagggag      9180
tcaggactgg tagtaacagc taccatgatt tatctatcaa tgcaccaaac atctgttgag      9240
caagcgctat gtactaggag ctgggagtac agagatgaga acagtcacaa gtccctcctc      9300
agataggaga ggcagctagt tataagcaga acaaggtaac atgacaagta gagtaagata      9360
gaagaacgaa gaggagtagc caggaaggag ggaggagaac gacataagaa tcaagcctaa      9420
agggataaac agaagatttc cacacatggg ctgggccaat tgggtgtcgg ttacgcctgt      9480
aatcccagca ctttgggtgg caggggcaga aagatcgctt gagcccagga gttcaagacc      9540
agcctgggca acatagtgag actcccatct ctacaaaaaa taaataaata aataaaacaa      9600
tcagccaggc atgctggcat gcacctgtag tcctagctac ttgggaagct gacactggag      9660
gattgcttga gcccagaagt tcaagactgc agtgagctta tccgttgacc tgcaggtcga      9720
c                                                                     9721
```

<210> SEQ ID NO 17
<211> LENGTH: 12565
<212> TYPE: DNA
<213> ORGANISM: Homo sapiens

<400> SEQUENCE: 17

```
gtcgacctgc aggtcaacgg atctgagagg agagtagctt cttgtagata acagttggat       60
tatataccat gtcctgatcc ccttcatcat ccaggagagc agaggtggtc accctgatag      120
cagcaagcct gggggctgca gcttggtggg tagaggtact cagggtaca gatgtctcca      180 aacctgtcct gctgccttag ggagcttcta ataagttgat ggatttggtt aaaattaact      240
```

```
tggctacttg gcaggactgg gtcagtgagg accaacaaaa agaagacatc agattatacc    300 ctggggttt  gtatttcttg tgtttctttc tcttctttgt actaaaatat ttacccatga    360
ctgggaaaga gcaactggag tctttgtagc attatcttag caaaaattta caagtttgg     420 aaaacaatat tgcccatatt gtgtggtgtg tcctgtgaca ctcaggattc aagtgttggc    480
cgaagccact aaatgtgaga tgaagccatt acaaggcagt gtgcacatct gtccacccaa    540
gctggatgcc aacatttcac aaatagtgct tgcgtgacac aaatgcagtt ccaggaggcc    600
caaatgaaaa tgtttgtact gaaatttgtt aaagcttccc gacaaactag atttatcagt    660
aaggattgtt ttctgcaagg gggatgaaac ttgtggggtg agccatttgg gctgaggagg    720
agggaggttg gagctgagaa atgtggagac aatttccctt tagaaggact gaatctccct    780
gcctctctgg ggtgcggcag ccagcaggat ccaatggtgt atatgtctcc ccagctcccc    840
attcagtgat atccatgtcag tagcttgaaa ttatccgtgg tgggagtatt atgtcatgga    900
aattggcaaa tggaaacttt tattggagat tcaattgtta aacttttacc agcacaacac    960
tgccctgcct tcagagtcaa tgaccctatc caagtttaat ccatctgtcc actgtctcca   1020
acacgatctt tataaaacac acctgacaac attacccttt tattcagttt tttaaaagat   1080
aagtttccag ctcatcgggg tggctttaaa ggccatttct cctctggacc tcacccaact   1140
tttcaaatca cttttcctac ccctacctct aaatgctact caaactccag ccatcctgaa   1200
taataagact tttgaaaagt agattatggg ctgggcacag tggctcacac ctgtaatccc   1260
agcactttgg gaggccaaga tgggtggatc acctgaggtc gggagttcga gaccagcctg   1320
actaacatag tgaaaccctg tctctactaa aaatacaaaa ttagttgggg gtggtggcac   1380
aagcctgtaa tcccagctac tcaggaggtt gaggcagggg aattgcttga acctgggagg   1440
cggaggttgc ggtgagccta gattgctcca ctgcactcca gcctgggcaa caagagcgaa   1500
actccatctc aaaaaaataa ataaataat  aaagtagatt acatcagata cctctggcct   1560
aggttgttta tgaccaactc tcctgctgag aataactaga aaagctagac aaaacatatt   1620
tccaaaagat ctctttggag gcatcagaga atggccaagg ctgtaaggaa ctgcctgagc   1680
ccagagaggt ggagcccagc actggtgccc tttactcctg gggacatgtg ctggtttcaa   1740
aaacttcagc tgagctttg  agcattcatg gaacttggtg ggggagatga aatttgtacc   1800
ttaaatcctg cctacaggga gggtccctga taatccccac ccaatttgga aatctgggtc   1860
agccttcaca ggtactgaag ccctcctctg aatgatctca agtcctgcta gggtagaggt   1920
tacctgcttt tgaaaggctc ctggcctacc tgtgcagcag gagcaaaagt gaaccatctc   1980
agggtacaga taacaatcat ccagagcctt gaatgacctc tactgtgctt aatatatagt   2040
attcagcagt cagtaaaaag gatttaggca catgcaagat gacctgtgta tcaggagaa    2100 ataggcaata aattgagatc cagcaggat  ttgaatcatg gatttgaatc aggggcagcc   2160
ttcgaaagaa ctatggagaa tatactcaga tttaaaacat aagattggaa ttttggcag    2220 agaactaaca actgtacaaa aaaggaacca aatgaaatc  ctagaactga agatgcaat    2280 taaccgatgt tgagaaatag ccaacatcta ttgaacactt cccatgtgga cagctgtgct   2340
aaacacttta caggcatcaa cataagatgt gtcccttac  agcagtgcag tgtccctcct   2400
aagacatgga cagcctggtt tccctatctc tctgcttcat caaaacccct ttacgtgggg   2460
cttagacact cctgttgtct ctagtgtcta gtagcacagg gctcagcaca tggaagccac   2520
tagatacaat ttgatgacca ggacctccga tgaaagccat gggtgctgat tgggaaggca   2580
```

-continued

```
ttgtctttta tgtgctatgg tcttaaagct tcatccagga agcagaactc gggggtgct      2640 gaggacccag aaccgagaat aagattagtc agagatttcc tgtgggcaga atcataagg      2700 acgccaactg tttgggtgag ataagacgaa accaagagtg acttgtggc cagaagcgtg      2760 aggaagaggg agagagcttc ccttgtcccc tttcttcctc tccctaagcc acagtgattg     2820 acagccccc cgctttggag tcagagcagg cttgagactg gactgggaaa ggagggtggg      2880
tcaggataca gagcaggaag gctgggagtg cagggcagga gcaaggggct ggggcattca    2940
ttgtgcctga tctctcccac tttacctggg gtaaagaagc atatgcaaaa gccacggtgt   3000
gagtatttcc caagtgccag ggtcagggca tgattcatca cgtgcagcat ttcattcaat   3060
ccttatagta accgatgatg tggcttctat tattagctct atcagataat gaaactgaga   3120
ccaagacagg ctctgcacat tgtgtgggt aatgacacag ggggattcag acctagactc    3180
cataactcct gccccaggga ccaccccac cctcaccctg tgcatgtcga caaggacag     3240 actgggccac ttctcaggac acagcgggga aatgacacag agcagggagg ttccaggagc   3300
cccgagcgtc ttttctccag gagaatactc tctgaattca gactgggtc agagaaacat    3360 ttacccagga gccgcagtgt gggtggggct ttttacttga aacgctgtct gaaggcagtg   3420
gcaggatgaa ctctccaccc taccttggca agccacttct cttctgcaat ctgtaaggac   3480
attgttgaga gaattatggt cttccaattc cggagggttg aagaaagaca aataggagag   3540
aacctatcat agtcaggtgc tagctgcctt ctctttcaga gagtgtgaga ataaagtgat   3600
acacttgatt attagcaaat actttggaaa ttttaaacgc taatattcaa cacactctgg   3660
aagaggcaaa taagtagaca ggttcatata catcatctcc ttcagctagt cctcacaaaa   3720
acaaacaaat gaataaacaa aattcttctt tggccctcat aggaagacac tgtttcttga   3780
acgtgtttca aaaaggatgg gtgactcact caaggtcaca ctgtttatga ggacagtaca   3840
ggaatacaga catgccattt tgcctgaaaa aatccatcac ccagggaggt gacacaattt   3900
tgcagaaatg ttctatttcc tctgaaggat acattcttta aacctttggg aaattcattc   3960
atagtcttcc tcctttgaag gattactctc tggacacaaa gtgtttgatt ctgatttgtt   4020
ggttggaaga tgtgttggtt gagagaaaga ttctgatttg ttggttgaaa atagactcat   4080
caagatcaac tgctgtagta gtaaatattt tgacattttg tctgtattcc tgtgctgccc   4140
tcacaagctg catcaccttg agtgagtcat tcatactttt ttgtttgttt ttgttttgga   4200
gatggagtct tactctgttg cctaggctgg agtgcggtgg cgtgatcttg gctcactgcg   4260
acctccatct cctgggttca agtgatcctc ctgcctcagc ctcccgagta gctgggatta   4320
caggcacatg ccaccatccc tgctaatttt tgcatttca gtagagacgg agtttcacca   4380
tgttggtcag gttggtcttg aactcctgac ctcaggtgat ccgcccacct cagcctcccc   4440
aagtgctggg attacaggtg tgagccaccg tgcccagccc agccatcatt tttgaaacac   4500
gtttgagaaa tagtgtcttc ctttgagggc caaggagaca ttttttttgt ttatttgttt   4560 gttttttgtga ggactagctg aaggggggtga tgtatattaa cctgcctact tatttgcctc   4620 tcccagagt gtgatgaata ttagggttta agtttctga agcatttgtt aataaagccc       4680
ggggctggag gtcagaagac ctggatttct ctgcatactt ttgccatcag caagctgtgt    4740
gaccttggac agatcccttt tttgtctaaa tctttctgag tcttcttgaa aacaatgcca    4800
ggttgggaca ggatgattgc caagctcccg tccagctcta aaacactgca acgtatgctt    4860
ctgcaccagc actgtccatc ctgtagatca tgcagaaatt ctcttcaact ttttcctacc   4920
cataaaatag gagcatgctt accttttttcc taatgttcca ggccccgggt ctagatattg    4980
```

-continued

```
taagtaagga agttaatgtg tatcagagcc cattatgggc cagaagttct cctcttcctt      5040
cctacacctg cttcctccct ccctccctcc ctctttccct tccttccttc catccatttg      5100
tgaagaagac atgatcaccc tcattctgag agtgaagaga cagaggctca actaatgaaa      5160
tgatttgttc aaggtcacac gggtggcaca aggcaagtgg cagaggttga atttagaccc      5220
attcctgtcc aaatgctgag tttatgtcat cgtcccgaga ccataacttt aaagatgtaa      5280
gatagtggga aaagagttga tttcaaagca cctctcagaa ggactcactt tacatcaggg      5340
gtcagcagac tcaggccaaa tccggtccat tccccgcttt tgcaaagaaa gttgtagtgg      5400
aacacagcta ggcttattga tttatggatt gccaacgtcc ttttgtgaaa cagacagctg      5460
agctgagtaa tcgtggcgca caaaacctaa aatatttact atctcgtcct ttacagaatg      5520
tttgccaatc tatggtccgg agtccaaggc tgtccatttt tcaaagaaca caaagtgaca      5580
tgagactgtc ccatgtgcag ggagccctat cattttatta tgaaaaaacg gcctttctgc      5640
tcaaatctgt tttttaaaaa gtcaacaaac agactctggg tacctgtcag gaacagtagg      5700
gagtttggtt tccattgtgc tcttcttccc aggaactcaa tgaagggaaa atagaaatct      5760
taattttggg gaaattgcac aggggaaaaa ggggagggaa tcagttacaa cactccattg      5820
cgacacttag tggggttgaa agtgacaaca gcaagggttt ctcttttttgg aaatgcgagg      5880 agggtatttc cgcttctcgc agtggggcag ggtggcagac gcctagcttg ggtgagtgac      5940
tatttcttta taaaccacaa ctctgggccc gcaatggcag tccactgctt gctgcagtca      6000
cagaatggaa atctgcagag gcctccgcag tcacctaatc actctcctcc tcttcctgtt      6060
ccattcagag acgatctgcc gaccctctgg gagaaaatcc agcaagatgc aagccttcag      6120
gtaaggctac cccaaggagg agaaggtgag ggtggatcag ctggagactg gaaacatatc      6180
acagctgcca gggctgccag gccagagggc ctgagaactg ggtttgggct ggagaggatg      6240
tccattattc aagaaagagg ctgttacatg catgggcttc aggacttgtg tttcaaaata      6300
tcccagatgt ggatagtgcg accggagggc tgtcttactt tcccagagac tcaggaaccc      6360
agtgagtaat agatgcatgc caaggagtgg gactgcgatt caggcctagt tgaatgtgct      6420
gacagagaag cagagagggg caccaggggc acagcccgaa ggcccagact gatatgggca      6480
aggcctgtct gtgctgacat gtcggagggt cccactctcc agggaccttg gtttccccgt      6540
ctgtgacatc tgtgacatga gagtcacgat aactccttgt gtgccttaca gggttgttgt      6600
gaaaattaaa tgcacagata atagcgtaac agtattccgt gcattgtaaa gagcctgaaa      6660
accattatga tttgaaaatg gaatcggctt tgtgagacca tcactattgt aaagatgtga      6720
tgctgataga aatgacagga ctgcttgtgc atgccctctg cagtgtgaca ttccagcagt      6780
gaaatcatgt tggggtgact ctcccccac tctgacctt atgtttgtct gggccgaggc      6840
tgcaagtcgg gctctgtggg tgtatgagtg acaagtctct cccttccaga tatggggact      6900
gtctgcttcc ctaggttgcc tctccctgct ctgatcagct agaagctcca ggagatcctc      6960
ctggaggccc cagcaggtga tgtttatccc tccagactga ggctaaatct agaaactagg      7020
ataatcacaa acaggccaat gctgccatat gcaaagcact ttggtttgcc tggccacccc      7080
tcgtcgagca tgtgggctct tcagagcacc tgatgaggtg ggtacagtta gccacacttc      7140
acaggtgaag aggtgaggca caggtcccag gtcaggctgg ccggagctct gtttattacg      7200
tctcacagct ttgagtcctg ctctcaacca gagaggccct taccaagaa gaaaggattg      7260 ggacccagaa tcaggtcact ggctgaggta gagaggaagc cgggttgttc ccaagggtag      7320
```

-continued

```
ctgctcctgc aggactctga gcaggtcacc agctaatgga ggaaaggctc tagggaaaga      7380
cccttctggt ctcagactca gagcgagtta gctgcaaggt gttccgtctc ttgaaacttc      7440
tacctaggtg ctatggtagc cactagtctc aggtggctat ttaaatttat acttaaatga      7500
atgaaaatag aagaaaattt aaaatccaga cccttggtca cactatccac atttaaagag      7560
gtcaatagcc acatgtggtt agtggccacc ctattgggca gtgcagctac agaacatttt      7620
tgcatcccag aaagttcttt tggatgttgc tgctctacag catgctttgc tgaaacagaa      7680
gtgccttccc tgggaatctc agatgggaag caagtaagga ggggagtcaa atgtgggctc      7740
actgctcacc agctgtgagg gttgggcctg cctcttaacc attgtcagcc tcagtcttct      7800
catccatgca tgccgtgggt atactaaaat actataccccc tggaagagct ggatgcaaat      7860
ttgacaagtt ctgggggaca caggaaggtg ccaagcacaa ggctgggcac atggtggctg      7920
tgcactacag ctgagtcctt ttccttttca gaatctggga tgttaaccag aagaccttct      7980
atctgaggaa caaccaacta gttgctggat acttgcaagg accaaatgtc aatttagaag      8040
gtgagtggtt gccaggaaag ccaatgtatc tgggcatcac gtcactttgc ccgtctgtct      8100
gcagcagcat ggcctgcctg cacaaaccct aggtgcaatg tcctaatcct tgtttgggtct      8160
ttgtattcaa gtttgaagct gggagggcct ggctactgaa gggcacatat gagggtagcc      8220
tgaagagggt gtggagaggt agagtctagg tcagaggtca gtgcctatag caagtggtc      8280
ccagggccac agctgggaag ggcaaatacc agaaggcaag gttgaccatt cccttcctca      8340
agtgcctatt aaggctccat gttcctatgt tgttcaaacc ctaactcaat cccaaattaa      8400
tccaccatgt ataaggttga gctatgtctc ttattcctgg acaccatact cagccatatc      8460
tggtccacac attaacagct ggatgacctt gaagaagctt cacccactct gttcctcagc      8520
tttcccttca gtgggatgat atcaactgga caacaggatg tgcgattctt ttagttccag      8580
ccttccagga tgttttcact cccctgtttg ttgttgtagg atggtattac ctccaccttc      8640
ccaccttccc tatgccctgg ttctgtctcc tgtgcctcgc tctgaaagtg atgagacct      8700
acaattcctg tcctggtagt tctcctaatg aacacactga agcacgagga agctgagatt      8760
tttgttgcta catgagagca tggaggcctc ttagggagag aggaggttca gagactccta      8820
ggctcctggt ggagccccac tcatggcctt gttcattttc cctgcccctc agcaacactc      8880
ctattgacct ggagcacagg tatcctgggg aaagtgaggg aaatatggac atcacatgga      8940
acaacatcca ggagactcag gcctctagga gtaactgggt agtgtgcatc ctggggaaag      9000
tgagggaaat atggacatca catggaacaa catccaggag actcaggcct ctaggagtaa      9060
ctgggtagtg tgcatcctgg ggaaagtgag ggaaatatgg acatcacatg gaacaacatc      9120
caggagactc aggcctctag gagtaactgg gtagtgtgca tcctggggaa agtgagggaa      9180
atatggacat cacatggaac aacatccagg agactcaggc tctaggagt aactgggtag      9240
tgtgcttggt ttaatcttct atttacctgc agaccaggaa gatgagacct ctctgccctt      9300
ctgacctcgg gattttagtt ttgtggggac cagggaagag agaaaaatac ccggggtctc      9360
ttcattattg ctgcttcctc ttctattaac ctgaccctcc cctctgttct tccccagaaa      9420
agatagatgt ggtacccatt gagcctcatg ctctgttctt gggaatccat ggagggaaga      9480
tgtgcctgtc ctgtgtcaag tctggtgatg agaccagact ccagctggag gtaaaaacat      9540
gctttggatc tcaaatcacc ccaaaaccca gtggcttgaa acaaccaaaa ttttttctta      9600
tgattctgtg ggttgaccag gattagctgg gtagttctgt tccatgtggt ggaacatgct      9660
ggggtcactt tggaagctgc attcagcaga gtgccaggct tgcgctgggc atccaaggtg      9720
```

-continued

```
gtccctcatc ctccaggctc tctttccatg tgatctctca gtgtttaaga gttagttgga    9780
gcttccttac agcatggcgg ctgacttcca aaagggatta ttccaaaaag agcctcaaca    9840
tgcaggcgct tattatgact tctgcttgca tcatcctatt ggccaaagcc agtcacgtgg    9900
ctaagtctag cccctgtga gaggagactg cataagagtg tgaacaccag gagacacggt    9960
cactggggc accactgta accatctacc acaggacctg aatctctgtg tgctactccc    10020
ttgctcaagg gccccctac ccacgcagac ctgctgtctt ctagcaaagc ccatcctcag    10080
gacctttctc ttccaatcct tattgactca aattgattag ttggtgctcc acccagagcc    10140
ctgtgctcct ttatctcatg taatgttaat gggtttccca gccctgggaa acatggctt    10200
tgtctcaggg gcttgctgga tgcaaccta acctcaatgt gagtggccat actgtggcac    10260
tgtcccatcc ctcaccaggg acactgttct ggagggtgac tgcctgttct gtgaggagtg    10320
gggatggcta ggacattgca tggaacacac caccacccca tcttctcaga gctcaaaccc    10380
tgacagaaca ccagctccac aggccttggc ttctgctgat ggtgccgtgt atttaccaga    10440
cttagtggtc caaggccaga gtggcagatt tcccaaagtc aaggtgtgac agtgggacag    10500
cctctttgtg tctttgctgt cctaagaaac ctgggccagg ccaggcgcag tggctcacgc    10560
cttgtaatcc cagcactttg agaggccaag gtgggcagat cacgaggtca ggagtttgag    10620
accagcctgg ccaacattgg tgaaaccctg tctctattaa aaatagaaaa cattagacag    10680
gtgtggtggt gcatgcctgt aatcccagct actcaggagg ctgaggcagg agaatcgctt    10740
gaacccagga ggtggaggtt gcagtgagcc gagattgtgc cactgcactc agcctaggc    10800
gacagagcaa gactccgtct cgggaaaatt aattaataaa taaataaacc taggtcccag    10860
agtcccacag aatggcagac aggagcacct gggggctttt agggtatggc atttcccctg    10920
tactaactct gggctgtcca gaggcgattt catggcgtgg agtggagagg gaggcagcac    10980
aggacttcct aggcctcagc tctcacctgc ccatcttttg atttccaggc agttaacatc    11040
actgacctga gcgagaacag aaagcaggac aagcgcttcg ccttcatccg ctcagacagt    11100
ggccccacca ccagttttga gtctgccgcc tgccccggtt ggttcctctg cacagcgatg    11160
gaagctgacc agcccgtcag cctcaccaat atgcctgacg aaggcgtcat ggtcaccaaa    11220
ttctacttcc aggaggacga gtagtactgc ccaggcctgc ctgttcccat tcttgcatgg    11280
caaggactgc agggactgcc agtcccctg ccccagggct cccggctatg ggggcactga    11340
ggaccagcca ttgaggggtg gaccctcaga aggcgtcaca acaacctggt cacaggactc    11400
tgcctcctct tcaactgacc agcctccatg ctgcctccag aatggtcttt ctaatgtgtg    11460
aatcagagca cagcagcccc tgcacaaagc ccttccatgt cgcctctgca ttcaggatca    11520
aaccccgacc acctgcccaa cctgctctcc tcttgccact gcctcttcct ccctcattcc    11580
accttcccat gccctggatc catcaggcca cttgatgacc cccaaccaag tggctcccac    11640
accctgtttt acaaaaaaga aagaccagt ccatgaggga ggttttaag ggtttgtgga    11700
aaatgaaaat taggatttca tgatttttt ttttcagtcc ccgtgaagga gagcccttca    11760
tttggagatt atgttctttc ggggagaggc tgaggactta aaatattcct gcatttgtga    11820
aatgatggtg aaagtaagtg gtagcttttc ccttcttttt cttcttttt tgtgatgtcc    11880
caacttgtaa aaattaaaag ttatggtact atgttagccc cataattttt ttttcctttt    11940
taaaacactt ccataatctg gactcctctg tccaggcact gctgcccagc ctccaagctc    12000
catctccact ccagattttt tacagctgcc tgcagtactt tacctcctat cagaagtttc    12060
```

-continued

```
tcagctccca aggctctgag caaatgtggc tcctgggggt tctttcttcc tctgctgaag   12120
gaataaattg ctccttgaca ttgtagagct tctggcactt ggagacttgt atgaaagatg   12180
gctgtgcctc tgcctgtctc cccaccaggc tgggagctct gcagagcagg aaacatgact   12240
cgtatatgtc tcaggtccct gcagggccaa gcacctagcc tcgctcttgg caggtactca   12300
gcgaatgaat gctgtatatg ttgggtgcaa agttccctac ttcctgtgac ttcagctctg   12360
ttttacaata aaatcttgaa aatgcctata ttgttgacta tgtccttggc cttgacaggc   12420
tttgggtata gagtgctgag gaaactgaaa gaccaatgtg tyttycttac cccagaggct   12480
ggcgcctggc ctcttctctg agagttcttt tcttccttca gcctcactct ccctggataa   12540
catgagagca aatctctctg cgggg                                         12565
```

```
<210> SEQ ID NO 18
<211> LENGTH: 25
<212> TYPE: DNA
<213> ORGANISM: Homo sapiens

<400> SEQUENCE: 18
tgtacctaag cccacccttt agagc                                         25

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
tggcctccag aaacctccaa                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
gctgatattc tggtgggaaa                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
ggcaagagca aaactctgtc                                               20

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 22
gggatgttaa ccagaagacc ttctatct                                      28

<210> SEQ ID NO 23
<211> LENGTH: 27
```

```
<212> TYPE: DNA
<213> ORGANISM: Artificial Sequence
<220> FEATURE:
<223> OTHER INFORMATION: Description of Artificial Sequence: Primer

<400> SEQUENCE: 23
caaccactca ccttctaaat tgacatt                                           27

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 24
aacaaccaac tagttgctgg atacttgcaa                                        30

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Probe

<400> SEQUENCE: 25
acaaccaact agttgccgga tacttgc                                           27

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:
      Illustrative zinc finger peptide

<400> SEQUENCE: 26

Thr Lys Pro Arg
  1

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence:
      Illustrative zinc finger peptide

<400> SEQUENCE: 27

Ile Thr Gly Ser Glu
  1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence:
      Illustrative zinc finger peptide

<400> SEQUENCE: 28

Val Thr Lys Phe Tyr Phe
  1               5

<210> SEQ ID NO 29
<211> LENGTH: 6
<212> TYPE: PRT
```

-continued

```
<213> ORGANISM: Artificial Sequence
<220> FEATURE:
<223> OTHER INFORMATION: Description of Artificial Sequence:
      Illustrative zinc finger peptide

<400> SEQUENCE: 29

Val Thr Asp Phe Tyr Phe
 1               5
```

DIAGNOSTICS AND THERAPEUTICS FOR RESTENOSIS

RELATED U.S. APPLICATIONS

This application is a continuation-in-part of U.S. application Ser. No. 09/431,352 filed Nov. 1, 1999, which application is hereby incorporated by reference.

1. BACKGROUND OF THE INVENTION

Restenoisis

Percutaneous transluminal coronary angioplasty (PTCA) is used to treat obstructive coronary artery disease by compressing atheromatous plaque to the sides of the vessel wall. PTCA is widely used with an initial success rate of over 90%. Approximately 666,000 angioplasties were conducted in the United States alone in 1996, and more of these procedures were performed on men (452,000) than women (214,000). Of this total, 482,000 were percutaneous transluminal coronary angioplasty (P.T.C.A. (American Heart Association; www.amhrt.org). Despite the frequent application of this procedure and its high initial success rate, the long-term success of PTCA is limited by intraluminal renarrowing or restenosis at the site of the procedure. This occurs within 6 months following the procedure in approximately 30% to 40% of patients who undergo a single vessel procedure and in more than 50% of those who undergo multivessel angioplasty.

Stent placement has largely supplanted balloon angioplasty because it is able to more widely restore intraluminal dimensions which has the effect of reducing restenosis by approximately 50%. Ironically, stent placement actually increases neointimal growth at the treatment site, but because a larger lumen can be achieved with stent placement, the tissue growth is more readily accommodate, and sufficient luminal dimensions are maintained, so that the restenosis rate is nearly halved by stent placement compared with balloon angioplasty alone.

The pathophysiological mechanisms involved in restenosis are not fully understood. While a number of clinical, anatomical and technical factors have been linked to the development of restenosis, at least 50% of the process has yet to be explained. However, it is known that following endothelial injury, a series of repair mechanisms are initiated. Within minutes of the injury, a layer of platelets and fibrin is deposited over the damaged endothelium. Within hours to days, inflammatory cells begin to infiltrate the injured area. Within 24 hours after an injury, vascular smooth muscle cells (SMCs) located in the vessel media commence DNA synthesis. A few days later, these activated, synthetic SMCs migrate through the internal elastic lamina towards the luminal surface. A neointima is formed by these cells by their continued replication and their production of extracellular matrix. An increase in the intimal thickness occurs with ongoing cellular proliferation matrix deposition. When these processes of vascular healing progress excessively, the pathological condition is termed intimal hyperplasia or neointimial hyperplasia. Histological studies in animal models have identified neointimal hyperplasia as the central element in restenosis.

Neointimal hyperplasia is understood to figure prominently in peripheral vascular restenosis following reconstructive procedures. One series of 5,000 arterial reconstructions reports 50% of late failures to be due to neointimal hyperplasia (Imparato et al. (1972) Surg. 72:1107–1117). Restenosis following stenting is similarly thought to involve an important component of neointimal hyperplasia (Dussaillant et al. (1995) J. Am. Coll. Cardiol 26:720–724).

In the coronary system, by contrast, restenosis following balloon angioplasty involves vascular remodeling as well as neointimal hyperplasia. The importance of vascular remodeling in this setting may be attributable to the nature of the injury to the vessel wall following balloon angioplasty. Commonly, the injury to the vessel wall with this procedure involves dissection planes extending through the atherosclerotic plaque into the vessel media (Mintz et al. (1996) Circ. 94:35043). Furthermore, plaque fracture, medial stretch, focal medial rupture and adventitial stretch all may occur following angioplasty. Repair of the deeper layers of the vessel wall takes place by the general processes of wound healing, including inflammation, neovascularization, fibroblast proliferation and eventual collagen deposition. Cumulatively, these processes lead to remodeling of the coronary vessel wall that may culminate in restenosis.

The biology of vascular wall healing implicated in restenosis therefore includes the general processes of wound healing and the specific processes of neointimal hyperplasia. Inflammation is generally regarded as an important component in both these processes. (Munro and Cotran (1993) Lab. Investig. 58:249–261; and Badimon et al. (1993), Supp II 87:3–6). Understanding the effects of acute and chronic inflammation in the blood vessel wall can thus suggest methods for diagnosing and treating restenosis and related conditions.

In its initial phase, inflammation is characterized by the adherence of leukocytes to the vessel wall. Leukocyte adhesion to the surface of damaged endothelium is mediated by several complex glycoproteins on the endothelial and neutrophil surfaces. Two of these binding molecules have been well-characterized: the endothelial leukocyte adhesion molecule-1 (ELAM-1) and the intercellular adhesion molecule-1 (ICAM-1). During inflammatory states, the attachment of neutrophils to the involved cell surfaces is greatly increased, primarily due to the upregulation and enhanced expression of these binding molecules. Substances thought to be primary mediators of the inflammatory response to tissue injury, including interleukin-1 (IL-1), tumor necrosis factor alpha (TNF-α), lymphotoxin and bacterial endotoxins, all increase the production of these binding substances.

After binding to the damaged vessel wall, leukocytes migrate into it. Once in place within the vessel wall, the leukocytes, in particular activated macrophages, then release additional inflammatory mediators, including IL-1, TNF, prostaglandin $E_2$, ($PGE_2$), bFGF, and transforming growth factors α and β (TGFα, TGFβ). All of these inflammatory mediators recruit more inflammatory cells to the damaged area, and regulate the further proliferation and migration of smooth muscle. A well-known growth factor elaborated by the monocyte-macrophage is monocyte- and macrophage-derived growth factor (MDGF), a stimulant of smooth muscle cell and fibroblast proliferation. MDGF is understood to be similar to platelet-derived growth factor (PDGF); in fact, the two substances may be identical. By stimulating smooth muscle cell proliferation, inflammation can contribute to the development and the progression of neointimal hyperplasia.

Leukocytes, attracted to the vessel wall by the abovementioned chemical mediators of inflammation, produce substances that have direct effects on the vessel wall that may exacerbate the local injury and prolong the healing response. First, leukocytes activated by the processes of inflammation secrete lysosomal enzymes that can digest collagen and other structural proteins. Releasing these enzymes within the vessel wall can affect the integrity of its extracellular matrix, permitting SMCs and other migratory cells to pass through the wall more readily. Hence, the release of these lysosomal proteases can enhance the processes leading to neointimal hyperplasia Second, activated leukocytes produce free radicals by the action of the NADPH system on their cell membranes. These free radicals can damage cellular elements directly, leading to an extension of a local injury or a prolongation of the cycle of injury-inflammation-healing.

The responses to vascular injury that lead to restenosis have certain features in common with the processes leading to the development of the vascular lesions of atherosclerosis. Currently, it is understood that the lesions of atherosclerosis are initiated by some form of injury to arterial endothelium, whether due to hemodynamic factors, endothelial dysfunction or a combination of these or other factors (Schoen, "Blood vessels, "pp. 467–516 in Pathological Basis of Disease (Philadelphia: Saunders, 1994)). Inflammation has been implicated in the formation and progression of atherosclerotic lesions. Several inflammatory products, including IL-1β, have been identified in atherosclerotic lesions or in the endothelium of diseased coronary arteries (Galea, et al. (1996) Arterioscler Thromb Vasc Biol. 16:1000–6). Also, serum concentrations of IL-1β are elevated in patients with coronary disease (Hasdai, et al. (1996) Heart, 76:24–8). Realizing the importance of inflammatory processes in the final common pathways of vascular response to injury allows analogies to be drawn between the lesions seen in restenosis and those seen in atherosclerosis.

Currently, approximately 500,000 patients per year undergo vascular reconstructive procedures, with half involving the coronary vessels and the other half involving the periphery. Restenosis and progressive atherosclerosis are the most common mechanisms for late failure in these reconstructions. It would be desirable to determine which patients would respond well to invasive treatments for occlusive vascular disease such as angioplasty and intravascular stent placement. It would be further desirable to identify those patients at increased risk for stenosis so that they could be targeted with appropriate therapies to prevent, modulate or reverse the condition. It would be desirable, moreover, to identify those individuals for whom PTCA and stent placement is a suboptimal therapeutic choice because of the risk of restenosis. Those patients might become candidates at earlier stages for vascular reconstructive procedures, possibly combined with other pharmacological interventions.

Genetics of the IL-1 Gene Cluster

The IL-1 gene cluster is on the long arm of chromosome 2 (2q13) and contains at least the genes for IL-1α (IL-1A), IL-1β (IL-1B), and the IL-1 receptor antagonist (IL-1RN), within a region of 430 Kb (Nicklin, et al. (1994) Genomics, 19: 382–4). The agonist molecules, IL-1α and IL-1β, have potent pro-inflammatory activity and are at the head of many inflammatory cascades. Their actions, often via the induction of other cytokines such as IL-6 and IL-8, lead to activation and recruitment of leukocytes into damaged tissue, local production of vasoactive agents, fever response in the brain and hepatic acute phase response. All three IL-1 molecules bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Inappropriate production of IL-1 plays a central role in the pathology of many autoimmune and inflammatory diseases, including rheumatoid arthritis, inflammatory bowel disorder, psoriasis, and the like. In addition, there are stable inter-individual differences in the rates of production of IL-1, and some of this variation may be accounted for by genetic differences at IL-1 gene loci. Thus, the IL-1 genes are reasonable candidates for determining part of the genetic susceptibility to inflammatory diseases, most of which have a multifactorial etiology with a polygenic component. Indeed, there is increasing evidence that certain alleles of the IL-1 genes are over-represented in these diseases.

Certain alleles from the IL-1 gene cluster are already known to be associated with particular disease states. For example, IL-1RN allele 2 has been shown to be associated with coronary artery disease (PCT/US/98/04725, and U.S. Ser. No. 08/813456), osteoporosis (U.S. Pat. No. 5,698,399), nephropathy in diabetes mellitus (Blakemore, et al. (1996) Hum. Genet 97(3): 369–74), alopecia areata (Cork, et al., (1995) J. Invest. Dermatol. 104(5 Supp.): 15S–16S; Cork et al. (1996) Dermatol Clin 14: 671–8), Graves disease (Blakemore, et al. (1995) J. Clin. Endocrinol. 80(1): 111–5), systemic lupus erythematosus (Blakemore, et al. (1994) Arthritis Rheum. 37: 1380–85), lichen sclerosis (Clay, et al. (1994) Hum. Genet. 94: 407–10), and ulcerative colitis (Mansfield, et al. (1994) Gastroenterol. 106(3): 637–42).

In addition, the IL-1A allele 2 from marker –889 and IL-1B (TaqI) allele 2 from marker +3954 have been found to be associated with periodontal disease (U.S. Pat. No. 5,686,246; Kornmman and diGiovine (1998) Ann Periodont 3: 327–38; Hart and Komman (1997) Periodontol 2000 14: 202–15; Newman (1997) Compend Contin Educ Dent 18: 881 –4; Komman et al. (1997) J. Clin Periodontol 24: 72–77). The IL-1A allele 2 from marker –889 has also been found to be associated with juvenile chronic arthritis, particularly chronic iridocyclitis (McDowell, et al. (1995) Arthritis Rheum. 38: 221–28 ). The IL-1B (TaqI) allele 2 from marker +3954 of IL-1B has also been found to be associated with psoriasis and insulin dependent diabetes in DR3/4 patients (di Giovine, et al. (1995) Cytokine 7: 606; Pociot, et al. (1992) Eur J. Clin. Invest. 22: 396–402). Additionally, the IL-1RN (VNTR) allele 1 has been found to be associated with diabetic retinopathy (see U.S. Ser No. 09/037472, and PCT/GB97/02790). Furthermore allele 2 of IL-1RN (VNTR) has been found to be associated with ulcerative colitis in Caucasian populations from North America and Europe (Mansfield, J. et al., (1994) Gastroenterology 106: 637–42). Interestingly, this association is particularly strong within populations of ethnically related Ashkenazi Jews (PCT WO97/25445).

Genotype Screening

Traditional methods for the screening of heritable diseases have depended on either the identification of abnormal gene products (e.g., sickle cell anemia) or an abnormal phenotype (e.g., mental retardation). These methods are of limited utility for heritable diseases with late onset and no easily identifiable phenotypes such as, for example, a predisposition to restenosis. With the development of simple and inexpensive genetic screening methodology, it is now possible to identify polymorphisms that indicate a propensity to develop disease, even when the disease is of polygenic origin. The number of diseases that can be screened by molecular biological methods continues to grow with increased understanding of the genetic basis of multifactorial disorders.

Genetic screening (also called genotyping or molecular screening), can be broadly defined as testing to determine if a patient has mutations (or alleles or polymorphisms) that either cause a disease state or are "linked" to the mutation causing a disease state. Linkage refers to the phenomenon that DNA sequences which are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given human population, they tend to either both occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

While the frequency of meiotic recombination between two markers is generally proportional to the physical distance between them on the chromosome, the occurrence of "hot spots" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage with this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore identification of a human haplotype which spans or is linked to a disease-causing mutational change, serves as a predictive measure of an individual's likelihood of having inherited that disease-causing mutation. Importantly, such prognostic or diagnostic procedures can be utilized without necessitating the identification and isolation of the actual disease-causing lesion. This is significant because the precise determination of the molecular defect involved in a disease process can be difficult and laborious, especially in the case of multifactorial diseases such as inflammatory disorders.

Indeed, the statistical correlation between an inflammatory disorder and an IL-1 polymorphism does not necessarily indicate that the polymorphism directly causes the disorder. Rather the correlated polymorphism may be a benign allelic variant which is linked to (i.e. in linkage disequilibrium with) a disorder-causing mutation which has occurred in the recent human evolutionary past, so that sufficient time has not elapsed for equilibrium to be achieved through recombination events in the intervening chromosomal segment. Thus, for the purposes of diagnostic and prognostic assays for a particular disease, detection of a polymorphic allele associated with that disease can be utilized without consideration of whether the polymorphism is directly involved in the etiology of the disease. Furthermore, where a given benign polymorphic locus is in linkage disequilibrium with an apparent disease-causing polymorphic locus, still other polymorphic loci which are in linkage disequilibrium with the benign polymorphic locus are also likely to be in linkage disequilibrium with the disease-causing polymorphic locus. Thus these other polymorphic loci will also be prognostic or diagnostic of the likelihood of having inherited the disease-causing polymorphic locus. Indeed, a broad-spanning human haplotype (describing the typical pattern of co-inheritance of alleles of a set of linked polymorphic markers) can be targeted for diagnostic purposes once an association has been drawn between a particular disease or condition and a corresponding human haplotype. Thus, the determination of an individual's likelihood for developing a particular disease of condition can be made by characterizing one or more disease-associated polymorphic alleles (or even one or more disease-associated haplotypes) without necessarily determining or characterizing the causative genetic variation.

2. SUMMARY OF THE INVENTION

In one aspect, the present invention provides novel methods and kits for determining whether a subject has or is predisposed to developing restenosis. Diagnosis of the presence of a restenosis disorder identifies those patients predisposed to the development of a restenosis disease, characterized by clinical events related to the recurrence of the initial vascular stenosis that is being treated by the stent. Determining which patients are at risk for developing the disease because they have the disorder thus opens the possibility of selecting therapies for the initial vascular stenosis most likely to avoid subsequent stenoses. Such patients might be preferred candidates for surgical revascularization rather than percutaneous transluminal angioplasty, for example, or such patients may benefit from pharmacological or topical interventions at an early stage that could affect the progression of the restenosis disorder.

In one embodiment, the method comprises determining whether a restenosis associated allele is present in a nucleic acid sample obtained from the subject., In a preferred embodiment, the restenosis associated allele is selected from the group consisting of allele 1 of each of the following markers: IL-1A (+4845), IL-1B(+3954), IL-1B(−511), IL-1RN (+2018) and IL-1RN (VNTR) or an allele that is in linkage disequilibrium with one of the aforementioned alleles. In preferred embodiments, the presence of a particular allelic pattern of one or more of the abovementioned IL-1 polymorphic loci is used to predict the susceptibility of an individual to developing restenosis. In particular, there are three patterns of alleles at four polymorphic loci in the IL-1 gene cluster that show various associations with particular cardiovascular disorders. These patterns are referred to herein as patterns 1, 2 and 3. Pattern 1 comprises an allelic pattern including allele 2 of IL-1A (+4845) or IL-1B(+3954) and allele 1 of IL-1B(−511) or IL-1RN (+2018), or an allele that is in linkage disequilibrium with one of the aforementioned allele. In a preferred embodiment, this allelic pattern permits the diagnosis of occlusive cardiovascular disorder. Pattern 2 comprises an allelic pattern including allele 2 of IL-1B (−511) or IL-1RN (+2018) and allele 1 of IL-1A (+4845) or IL-1B (+3954), or an allele that is in linkage disequilibrium with one of the aforementioned alleles. In a preferred embodiment, this allelic pattern permits the diagnosis of occlusive cardiovascular disorder. Pattern 3 comprises an allelic pattern including allele 1 of IL-1A (+4845) or allele 1 of IL-1B (+3954), and allele 1 of IL-1B (−511) or allele 1 of IL-1RN (+2018), or an allele that is in linkage disequilibrium with one of the aforementioned alleles. In a preferred embodiment, this allelic pattern permits the diagnosis of a restenosis disorder.

In another embodiment, the method of the invention may be employed by detecting the presence of an IL-1 associated polymorphism that is in linkage disequilibrium with one or more of the aforementioned restenosis-predictive alleles. For example, the following alleles of the IL-1 (44112332) haplotype are known to be in linkage disequilibrium:

allele 4 of the 222/223 marker of IL-1A
allele 4 of the gz5/gz6 marker of IL-1A
allele 1 of the −889 marker of IL-1A
allele 1 of the +3954 marker of IL-1B
allele 2 of the −511 marker of IL-1B
allele 3 of the gaat.p33330 marker
allele 3 of the Y31 marker
allele 2 of the VNTR or (+2018) marker of IL-1RN Also, the following alleles of the IL-1 (33221461) haplotype are in linkage disequilibrium:

allele 3 of the 222/223 marker of IL-1A
allele 3 of the gz5/gz6 marker of IL-1A
allele 2 of the −889 marker of IL-1A
allele 2 of the +3954 marker of IL-1B
allele 1 of the −511 marker of IL-1B
allele 4 of the gaat.p33330 marker
allele 6 of the Y31 marker
allele 1 of the VNTR or (+2018) marker of IL-IRN A restenosis associated allele can be detected by any of a variety of available techniques, including: 1) performing a hybridization reaction between a nucleic acid sample and a probe that is capable of hybridizing to the allele; 2) sequencing at least a portion of the allele; or 3) determining the electrophoretic mobility of the allele or fragments thereof (e.g., fragments generated by endonuclease digestion). The allele can optionally be subjected to an amplification step prior to performance of the detection step. Preferred amplification methods are selected from the group consisting of: the polymerase chain reaction (PCR), the ligase chain reaction (LCR), strand displacement amplification (SDA), cloning, and variations of the above (e.g. RT-PCR and allele specific amplification). Oligonucleotides necessary for amplification may be selected for example, from within the IL-1 gene loci, either flanking the marker of interest (as required for PCR amplification) or directly overlapping the marker (as in ASO hybridization). In a particularly preferred embodiment, the sample is hybridized with a set of primers, which hybridize 5' and 3' in a sense or antisense sequence to the restenosis associated allele, and is subjected to a PCR amplification.

A restenosis associated allele may also be detected indirectly, e.g. by analyzing the protein product encoded by the DNA. For example, where the marker in question results in the translation of a mutant protein, the protein can be detected by any of a variety of protein detection methods. Such methods include immunodetection and biochemical tests, such as size fractionation, where the protein has a change in apparent molecular weight either through truncation, elongation, altered folding or altered post-translational modifications.

In another aspect, the invention features kits for performing the above-described assays. The kit can include a nucleic acid sample collection means and a means for determining whether a subject carries a restenosis associated allele. The kit may also contain a control sample either positive or negative or a standard and/or an algorithmic device for assessing the results and additional reagents and components including: DNA amplification reagents, DNA polymerase, nucleic acid amplification reagents, restrictive enzymes, buffers, a nucleic acid sampling device, DNA purification device, deoxynucleotides, oligonucleotides (e.g. probes and primers) etc.

As described above, the control samples may be positive or negative controls. Further, the control sample may contain the positive (or negative) products of the allele detection technique employed. For example, where the allele detection technique is PCR amplification, followed by size fractionation, the control sample may comprise DNA fragments of the appropriate size. Likewise, where the allele detection technique involves detection of a mutated protein, the control sample may comprise a sample of mutated protein. However, it is preferred that the control sample comprises the material to be tested. For example, the controls may be a sample of genomic DNA or a cloned portion of the IL-1 gene cluster. Preferably, however, the control sample is a highly purified sample of genomic DNA where the sample to be tested is genomic DNA.

The oligonucleotides present in said kit may be used for PCR amplification of the region of interest or for direct allele specific oligonucleotide (ASO) hybridization to the markers in question. Thus, the oligonucleotides may either flank the marker of interest (as required for PCR amplification) or directly overlap the marker (as in ASO hybridization).

Such oligonucleotides can include, but are not limited to:

5' ATG GTT TTA GAA ATC ATC AAG CCT AGG GCA 3' (SEQ ID No. 1) and 5' AAT GAA AGG AGG GGA GGA TGA CAG AAA TGT 3' (SEQ ID No. 2) which can be used to amplify the human IL-1A (+4845) polymorphic locus;

5' TGG CAT TGA TCT GGT TCA TC 3' (SEQ ID No. 3) and 5' GTT TAG GAA TCT TCC CAC TT-3' (SEQ ID No. 4) which can be used to amplify the human IL-1B (−511) polymorphic locus;

5'-CTC AGG TGT CCT CGA AGA AAT CAA A-3' (SEQ ID No. 5) and 5' GCT TTT TTG CTG TGA GTC CCG-3' (SEQ ID No. 6) which can be used to amplify the human IL-1B (+3954) polymorphic locus;

5'-CTC.AGC.AAC.ACT.CCT.AT-3' (SEQ ID NO. 7) and 5'-TCC.TGG.TCT.GCA.GCT.AA-3' (SEQ ID NO. 8) which can be used to amplify the human IL-1RN (VNTR) polymorphic locus;

5'-CTA TCT GAG GAA CAA CCA ACT AGT AGC-3' (SEQ ID NO. 9) and 5'-TAG GAC ATT GCA CCT AGG GTT TGT-3' (SEQ ID NO. 10) which can be used to amplify the human IL-1RN (+2018) polymorphic locus;

5' ATT TTT TTA TAA ATC ATC AAG CCT AGG GCA 3' (SEQ. ID No. 11) and 5' AAT TAA AGG AGG GAA GAA TGA CAG AAA TGT 3' (SEQ. ID No. 12) which can also be used to amplify the human IL-1A (+4845) polymorphic locus;

5'-AAG CTT GTT CTA CCA CCT GAA CTA GGC.-3' (SEQ. ID NO. 13) and 5'-TTA CAT ATG AGC CTT CCA TG.-3' (SEQ. ID NO. 14) which can be used to amplify the human IL-1A (−889) polymorphic locus;

Information obtained using the assays and kits described herein (alone or in conjunction with information on another genetic defect or environmental factor, which contributes to restenosis) is useful for determining whether a non-symptomatic subject has or is likely to develop restenosis. In addition, the information can allow a more customized approach to preventing the onset or progression of restenosis. For example, this information can enable a clinician to more effectively prescribe a therapy that will address the molecular basis of restenosis. In yet a further aspect, the invention features methods for treating or preventing the development of restenosis in a subject by administering to the subject an appropriate restenosis therapeutic of the invention. In still another aspect, the invention provides in vitro or in vivo assays for screening test compounds to identify restenosis therapeutics. In one embodiment, the assay comprises contacting a cell transfected with a restenosis causative mutation that is operably linked to an appropriate promoter with a test compound and determining the level of expression of a protein in the cell in the presence and in the absence of the test compound. In a preferred embodiment, the restenosis causative mutation results in decreased production of IL-1 receptor antagonist, and increased production of the IL-1 receptor antagonist in the presence of the test compound indicates that the compound is an agonist of IL-1 receptor antagonist activity. In another preferred embodiment, the restenosis causative mutation results in increased production of IL-1α or IL-1β, and decreased production of IL-1α or IL-1β in the presence of the test compound indicates that the compound is an antagonist of IL-1α or IL-1β activity. In another embodiment, the invention features transgenic non-human animals and their use in identifying antagonists of IL-1α or IL-1β activity or agonists of IL-1Ra activity.

Other embodiments and advantages of the invention are set forth in part in the description which follows, and will be obvious from this description.

3. BRIEF DESCRIPTION OF THE FIGURES

FIG. 1 shows the nucleic acid sequence for IL-1A (GEN X03833; SEQ ID No. 15).

FIG. 2 shows the nucleic acid sequence for IL-1B (GEN X04500; SEQ ID No. 16).

FIG. 3 shows the nucleic acid sequence for the secreted IL-1RN (GEN X64532; SEQ ID No. 17).

Figure 7:
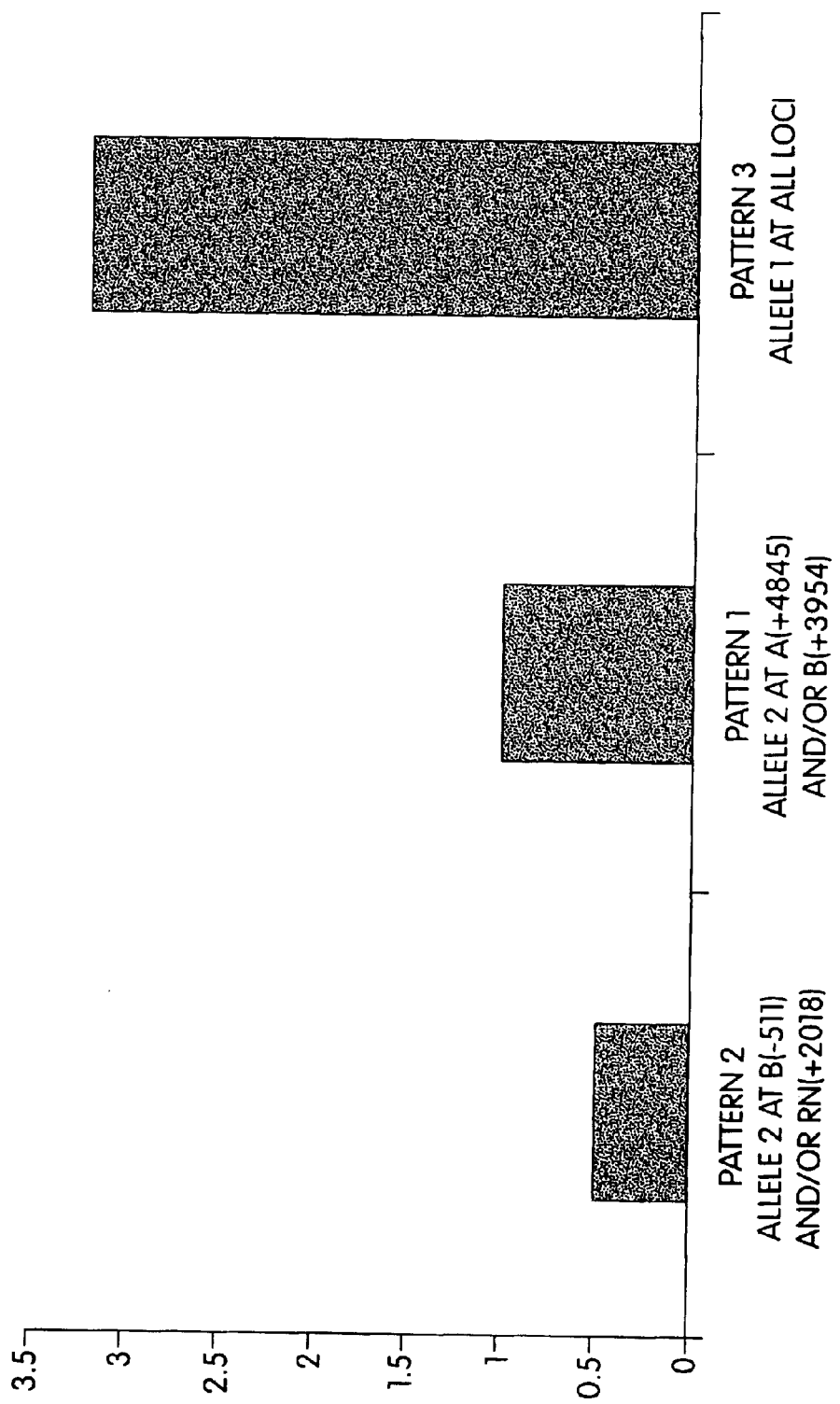

FIG. 7 indicates the relative risk for restenosis associated with each of the IL-1 polymorphic patterns.

Figure 8:
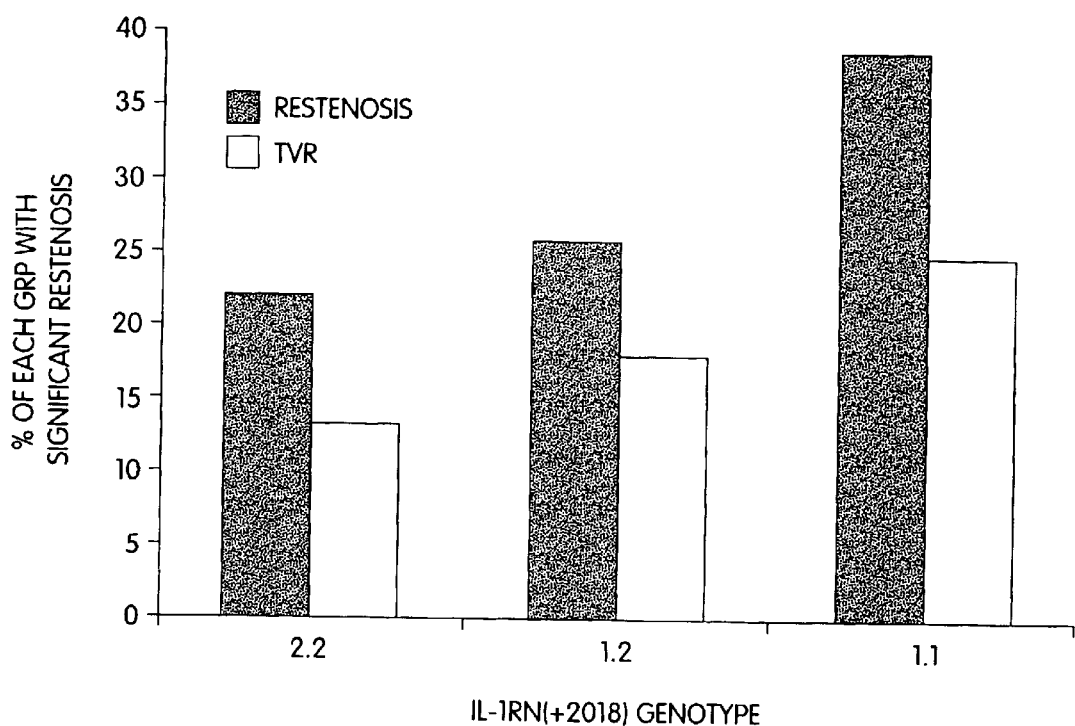

FIG. 8 indicates the association between homozygous and heterozygous allelic patterns at the IL-1RN(+2018) locus and the occurrence of restenosis and target vessel revascularization.

Figure 9:
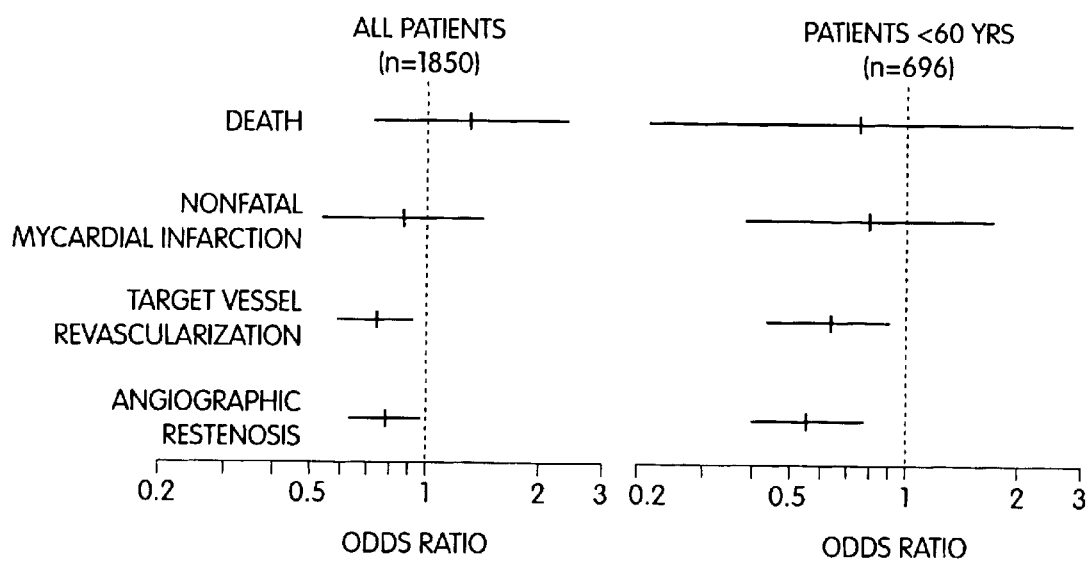

FIG. 9 is a graph showing the odds ratios for clinical events and angiographic restenosis associated with the presence of the IL-1RN*2 allele for the whole population (left panel) and patients <60 years (right panel)

Figure 10:
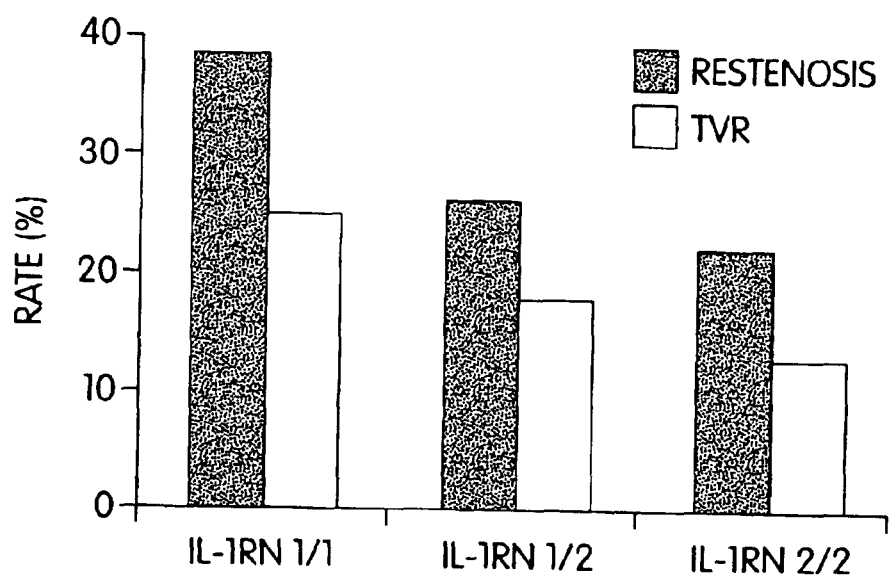

FIG. 10. is a bar graph showing the decrease in the incidence of restenosis and target vessel revascularization (TVR) in patients <60 years with the increase in the number of IL-1RN*2 alleles.

4. DETAILED DESCRIPTION OF THE INVENTION

4.1 Definitions

For convenience, the meaning of certain terms and phrases employed in the specification, examples, and appended claims are provided below.

The term "allele" refers to the different sequence variants found at different polymorphic regions. For example, IL-1RN (VNTR) has at least five different alleles. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site, as for IL-1RN (VNTR) allele 1, which is an allelic pattern having at least one copy of IL-1RN allele 1 at the VNTR of the IL-1RN gene loci. Alternatively, an allelic pattern may consist of either a homozygous or heterozygous state at a single polymorphic site. For example, IL-1RN (VNTR) allele 2,2 is an allelic pattern in which there are two copies of the second allele at the VNTR marker of IL-1RN and that corresponds to the homozygous IL-RN (VNTR) allele 2 state. Alternatively, an allelic pattern may consist of the identity of alleles at more than one polymorphic site.

The term "antibody" as used herein is intended to refer to a binding agent including a whole antibody or a binding fragment thereof which is specifically reactive with an IL-1B polypeptide. Antibodies can be fragmented using conventional techniques and the fragments screened for utility in the same manner as described above for whole antibodies. For example, $F(ab)_2$ fragments can be generated by treating an antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for an IL-1B polypeptide conferred by at least one CDR region of the antibody.

"Biological activity" or "bioactivity" or "activity" or "biological function", which are used interchangeably, for the purposes herein means an effector or antigenic function that is directly or indirectly performed by an IL-1 polypeptide (whether in its native or denatured conformation), or by any subsequence thereof Biological activities include binding to a target peptide, e.g., an IL-1 receptor. An IL-1 bioactivity can be modulated by directly affecting an IL-1 polypeptide. Alternatively, an IL-1 bioactivity can be modulated by modulating the level of an IL-1 polypeptide, such as by modulating expression of an IL-1 gene.

As used herein the term "bioactive fragment of an IL-1 polypeptide" refers to a fragment of a full-length IL-1 polypeptide, wherein the fragment specifically mimics or antagonizes the activity of a wild-type IL-1 polypeptide. The bioactive fragment preferably is a fragment capable of interacting with an interleukin receptor.

The term "an aberrant activity", as applied to an activity of a polypeptide such as IL-1, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant IL-1 activity due to overexpression or underexpression of an IL-1 locus gene encoding an IL-1 locus polypeptide.

"Cells", "host cells" or "recombinant host cells" are terms used interchangeably herein to refer not only to the particular subject cell, but to the progeny or potential progeny of such a cell. Because certain modifications may occur in succeeding generations due to either mutation or environmental influences, such progeny may not, in fact be identical to the parent cell, but is still included within the scope of the term as used herein.

A "chimera," "mosaic," "chimeric mammal" and the like, refers to a transgenic mammal with a knock-out or knock-in construct in at least some of its genome-containing cells.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified sample of genomic DNA.

A "cardiovascular disease" is a cardiovascular disorder, as defined herein, characterized by clinical events including clinical symptoms and clinical signs. Clinical symptoms are those experiences reported by a patient that indicate to the clinician the presence of pathology. Clinical signs are those objective findings on physical or laboratory examination that indicate to the clinician the presence of pathology. "Cardiovascular disease" includes both "coronary artery disease" and "peripheral vascular disease," both terms being defined below. Clinical symptoms in cardiovascular disease include chest pain, shortness of breath, weakness, fainting spells, alterations in consciousness, extremity pain, paroxysmal nocturnal dyspnea, transient ischemic attacks and other such phenomena experienced by the patient. Clinical signs in cardiovascular disease include such findings as EKG abnormalities, altered peripheral pulses, arterial bruits, abnormal heart sounds, rales and wheezes, jugular venous distention, neurological alterations and other such findings discerned by the clinician. Clinical symptoms and clinical signs can combine in a cardiovascular disease such as a myocardial infarction (MI) or a stroke (also termed a "cerebrovascular accident" or "CVA"), where the patient will report certain phenomena (symptoms) and the clinician will perceive other phenomena (signs) all indicative of an underlying pathology. "Cardiovascular disease" includes those diseases related to the cardiovascular disorders of fragile plaque disorder, occlusive disorder and stenosis. For example, a cardiovascular disease resulting from a fragile plaque disorder, as that term is defined below, can be termed a "fragile plaque disease." Clinical events associated with fragile plaque disease include those signs and symptoms where the rupture of a fragile plaque with subsequent acute thrombosis or with distal embolization are hallmarks. Examples of fragile plaque disease include certain strokes and myocardial infarctions. As another example, a cardiovascular disease resulting from an occlusive disorder can be termed an "occlusive disease." Clinical events associated with occlusive disease include those signs and symptoms where the progressive occlusion of an artery affects the amount of circulation that reaches a target tissue. Progressive arterial occlusion may result in progressive ischemia that may ultimately progress to tissue death if the amount of circulation is insufficient to maintain the tissues. Signs and symptoms of occlusive disease include claudication, rest pain, angina, and gangrene, as well as physical and laboratory findings indicative of vessel stenosis and decreased distal perfusion. As yet another example, a cardiovascular disease resulting from restenosis can be termed an in-stent stenosis disease. In-stent stenosis disease includes the signs and symptoms resulting from the progressive blockage of an arterial stent that has been positioned as part of a procedure like a percutaneous transluminal angioplasty, where the presence of the stent is intended to help hold the vessel in its newly expanded configuration. The clinical events that accompany in-stent stenosis disease are those attributable to the restenosis of the reconstructed artery.

A "cardiovascular disorder" refers broadly to both to coronary artery disorders and peripheral arterial disorders. The term "cardiovascular disorder" can apply to any abnormality of an artery, whether structural, histological, biochemical or any other abnormality. This term includes those disorders characterized by fragile plaque (termed herein "fragile plaque disorders"), those disorders characterized by vaso-occlusion (termed herein "occlusive disorders"), and those disorders characterized by restenosis. A "cardiovascular disorder" can occur in an artery primarily, that is, prior to any medical or surgical intervention. Primary cardiovascular disorders include, among others, atherosclerosis, arterial occlusion, aneurysm formation and thrombosis. A "cardiovascular disorder" can occur in an artery secondarily, that is, following a medical or surgical intervention. Secondary cardiovascular disorders include, among others, post-traumatic aneurysm formation, restenosis, and post-operative graft occlusion.

A "cardiovascular disorder causative functional mutation" refers to a mutation which causes or contributes to the development of a cardiovascular disorder in a subject. Preferred mutations occur within the IL-1 complex. A cardiovascular disorder causative functional mutation occurring within an IL-1 gene (e.g. IL-1A, IL-1B or IL-1RN) or a gene locus, which is linked thereto, may alter, for example, the open reading frame or splicing pattern of the gene, thereby resulting in the formation of an inactive or hypoactive gene product. For example, a mutation which occurs in intron 6 of the IL-1A locus corresponds to a variable number of tandem repeat 46 bp sequences corresponding to from five to 18 repeat units (Bailly, et al. (1993) Eur. J. Immunol. 23: 1240–45). These repeat sequences contain three potential binding sites for transcriptional factors: an SP1 site, a viral enhancer element, and a glucocorticoid-responsive element; therefore individuals carrying IL-1A intron 6 VNTR alleles with large numbers of repeat units may be subject to altered transcriptional regulation of the IL-1A gene and consequent perturbations of inflammatory cytokine production. Indeed, there is evidence that increased repeat number at this polymorphic IL-1A locus leads to decreased IL-1α synthesis (Bailly et al. (1996) Mol Immunol 33: 999–1006). Alternatively, a mutation can result in a hyperactive gene product. For example, allele 2 of the IL-1B (G at +6912) polymorphism occurs in the 3' UTR (untranslated region) of the IL-1B mRNA and is associated with an approximately four-fold increase in the steady state levels of both IL-1B mRNA and IL-1B protein compared to those levels associated with allele 1 of the IL-1B gene at +6912). Further, an IL-1B (−511) mutation occurs near a promoter binding site for a negative glucocorticoid response element (Zhang et al. (1997) DNA Cell Biol 16: 145–52). This element potentiates a four-fold repression of IL-1B expression by dexamethosone and a deletion of this negative response elements causes a 2.5-fold increase in IL-1B promoter activity. The IL-1B (−511) polymorphism may thus directly affect cytokine production and inflammatory responses. These examples demonstrate that genetic variants occurring in the IL-1A or IL-1B gene can directly lead to the altered production or regulation of IL-1 cytokine activity.

A "cardiovascular disorder therapeutic" refers to any agent or therapeutic regimen (including pharmaceuticals, nutraceuticals and surgical means) that prevents or postpones the development of or reduces the extent of an abnormality constitutive of a cardiovascular disorder in a subject. Cardiovascular disorder therapeutics can be directed to the treatment of any cardiovascular disorder, including fragile plaque disorder, occlusive disorder and restenosis. Examples of therapeutic agents directed to each category of cardiovascular disorder are provided herein. It is understood that a therapeutic agent may be useful for more than one category of cardiovascular disorder. The therapeutic can be a polypeptide, peptidomimetic, nucleic acid or other inorganic or organic molecule, preferably a "small molecule" including vitamins, minerals and other nutrients. Preferably the therapeutic can modulate at least one activity of an IL-1 polypeptide, e.g., interaction with a receptor, by mimicking or potentiating (agonizing) or inhibiting (antagonizing) the effects of a naturally-occurring polypeptide. An IL-1 agonist can be a wild-type protein or derivative thereof having at least one bioactivity of the wild-type, e.g., receptor binding activity. An IL-1 agonist can also be a compound that upregulates expression of a gene or which increases at least one bioactivity of a protein. An IL-1 agonist can also be a compound which increases the interaction of a polypeptide with another molecule, e.g., a receptor. An IL-1 antagonist can be a compound which inhibits or decreases the interaction between a protein and another molecule, e.g., a receptor or an agent that blocks signal transduction or post-translation processing (e.g., IL-1 converting enzyme (ICE) inhibitor). Accordingly, a preferred antagonist is a compound which inhibits or decreases binding to a receptor and thereby blocks subsequent activation of the receptor. An IL-1 antagonist can also be a compound that downregulates expression of a gene or which reduces the amount of a protein present. The antagonist can be a dominant negative form of a polypeptide, e.g., a form of a polypeptide which is capable of interacting with a target peptide, e.g., a receptor, but which does not promote the activation of the receptor. The antagonist can also be a nucleic acid encoding a dominant negative form of a polypeptide, an antisense nucleic acid, or a ribozyme capable of interacting specifically with an RNA. Yet other antagonists are molecules which bind to a polypeptide and inhibit its action. Such molecules include peptides, e.g., forms of target peptides which do not have biological activity, and which inhibit binding to receptors. Thus, such peptides will bind to the active site of a protein and prevent it from interacting with target peptides. Yet other antagonists include antibodies that specifically interact with an epitope of a molecule, such that binding interferes with the biological function of the polypeptide. In yet another preferred embodiment, the antagonist is a small molecule, such as a molecule capable of inhibiting the interaction between a polypeptide and a target receptor. Alternatively, the small molecule can function as an antagonist by interacting with sites other than the receptor binding site. Preferred therapeutics include lipid lowering drugs, antiplatelet agents, anti-inflammatory agents and antihypertensive agents.

"Cerebrovascular disease," as used herein, is a type of peripheral vascular disease (as defined below) where the peripheral vessel blocked is part of the cerebral circulation. The cerebral circulation includes the carotid and the vertebral arterial systems. This definition of cerebrovascular disease is intended specifically to include intracranial hemorrhage that does not occur as a manifestation of an arterial blockage. Blockage can occur suddenly, by mechanisms such as plaque rupture or embolization. Blockage can occur progressively, with narrowing of the artery via myointimal hyperplasia and plaque formation. Blockage can be complete or partial. Certain degrees and durations of blockage result in cerebral ischemia, a reduction of blood flow that lasts for several seconds to minutes. The prolongation of cerebral ischemia can result in cerebral infarction. Ischemia and infarction can be focal or widespread. Cerebral ischemia or infarction can result in the abrupt onset of a non-convulsive focal neurological defect, a clinical event termed a "stroke" or a "cerebrovascular accident (CVA)". Cerebrovascular disease has two broad categories of pathologies: thrombosis and embolism. Thrombotic strokes occur without warning symptoms in 80–90% of patients; between 10 and 20% of thrombotic strokes are heralded by transient ischemic attacks. A cerebrovascular disease can be associated with a fragile plaque disorder. The signs and symptoms of this type of cerebrovascular disease are those associated with fragile plaque, including stroke due to sudden arterial blockage with thrombus or embolus formation. A cerebrovascular disease can be associated with occlusive disorder. The signs and symptoms of this type of cerebrovascular disease relate to progressive blockage of blood flow with global or local cerebral ischemia. In this setting, neurological changes can be seen, including stroke.

A "clinical event" is an occurrence of clinically discernible signs of a disease or of clinically reportable symptoms of a disease. "Clinically discernible" indicates that the sign can be appreciated by a health care provider. "Clinically reportable" indicates that the symptom is the type of phenomenon that can be described to a health care provider. A clinical event may comprise clinically reportable symptoms even if the particular patient cannot himself or herself report them, as long as these are the types of phenomena that are generally capable of description by a patient to a health care provider.

A "coronary artery disease" ("CAD") refers to a vascular disorder relating to the blockage of arteries serving the heart. Blockage can occur suddenly, by mechanisms such as plaque rupture or embolization. Blockage can occur progressively, with narrowing of the artery via myointimal hyperplasia and plaque formation. Those clinical signs and symptoms resulting from the blockage of arteries serving the heart are manifestations of coronary artery disease. Manifestations of coronary artery disease include angina, ischemia, myocardial infarction, cardiomyopathy, congestive heart failure, arrhythmias and aneurysm formation. It is understood that fragile plaque disease in the coronary circulation is associated with arterial thrombosis or distal embolization that manifests itself as a myocardial infarction. It is understood that occlusive disease in the coronary circulation is associated with arterial stenosis accompanied by anginal symptoms, a condition commonly treated with pharmacological interventions and with angioplasty.

A "disease" is a disorder characterized by clinical events including clinical signs and clinical symptoms. The diseases discussed herein include cardiovascular disease, peripheral vascular disease, CAD, cerebrovascular disease, and those diseases in any anatomic location associated with fragile plaque disorder, with occlusive disorder or with restenosis.

A "disorder associated allele" or "an allele associated with a disorder" refers to an allele whose presence in a subject indicates that the subject has or is susceptible to developing a particular disorder. One type of disorder associated allele is a "cardiovascular disorder associated allele," the presence of which in a subject indicates that the subject has or is susceptible to developing a cardiovascular disorder. These include broadly within their scope alleles which are associated with "fragile plaque disorders," alleles associated with "occlusive disorders," and alleles associated with restenosis. Examples of alleles associated with "fragile plaque disorders" include those alleles comprising the IL-1 pattern 1- i.e. allele 2 of the IL-1A +4825; allele 2 of the +3954 marker of IL-1B; and allele 1 of the +2018 marker of IL-1RN; and allele 1 of the (−511) marker of the IL-1B gene or an allele that is in linkage disequilibrium with one of the aforementioned alleles. Examples of alleles associated with "occlusive disorders" include those comprising the IL-1 pattern 2- i.e. allele 1 of the IL-1A +4825; allele 1 of the +3954 marker of IL-1B; and allele 2 of the +2018 marker of IL-1RN; and allele 2 of the (−511) marker of the IL-1B gene or an allele that is in linkage disequilibrium with one of the aforementioned alleles. Examples of alleles associated with restenosis include the combination of either allele 1 of the +4825 marker of IL-1A or allele 1 of the +3954 marker as combined with either allele 1 of the −511 marker of IL-1B or allele 1 of the +2018 marker of IL-1RN, or an allele that is in linkage disequilibrium with one of the aforementioned alleles. A "periodontal disorder associated allele" refers to an allele whose presence in a subject indicates that the subject has or is susceptible to developing a periodontal disorders.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

The term "haplotype" as used herein is intended to refer to a set of alleles that are inherited together as a group (are in linkage disequilibrium) at statistically significant levels ($p_{corr}<0.05$). As used herein, the phrase "an IL-1 haplotype" refers to a haplotype in the IL-1 loci.

The term "hyperplasia" as used herein is intended to refer to an abnormal or unusual increase in growth or division of the cells composing a tissue or organ. It is understood that the term "hyperplasia," as used herein, encompasses a wide variety of specific proliferative states including "neointimal hyperplasia" or "neointimal growth," which refers to hyperplasia of the of cells in the endothelial layer of a blood vessel and "myointimal hyperplasia" or "myointimal growth," which refers to an abnormal proliferation of smooth muscle cells of the vascular wall. The terms myointimal and neointimal are used interchangeably herein.

An "IL-1 agonist" as used herein refers to an agent that mimics, upregulates (potentiates or supplements) or otherwise increases an IL-1 bioactivity or a bioactivity of a gene in an IL-1 biological pathway. IL-1 agonists may act on any of a variety of different levels, including regulation of IL-1 gene expression at the promoter region, regulation of mRNA splicing mechanisms, stabilization of mRNA, phosphorylation of proteins for translation, conversion of proIL-1 to mature IL-1 and secretion of IL-1. Agonists that increase IL-1 synthesis include: lipopolysaccharides, IL-1B, cAMP inducing agents, NFκB activating agents, AP-1 activating agents, TNF-α, oxidized LDL, advanced glycosylation end products (AGE), sheer stress, hypoxia, hyperoxia, ischemia reperfusion injury, histamine, prostaglandin E 2 (PGE2), IL-2, IL-3, IL-12, granulocyte macrophage-colony stimulating factor (GM-CSF), monocyte colony stimulating factor (M-CSF), stem cell factor, platelet derived growth factor (PDGF), complement C5A, complement C5b9, fibrin degradation products, plasmin, thrombin, 9-hydroxyoctadecaenoic acid, 13-hydroxyoctadecaenoic acid, platelet activating factor (PAF), factor H, retinoic acid, uric acid, calcium pyrophosphate, polynucleosides, c-reactive protein, α-antitrypsin, tobacco antigen, collagen, β-1 integrins, LFA-3, anti-HLA-DR, anti-IgM, anti-CD3, phytohemagglutinin (CD2), sCD23, ultraviolet B radiation, gamma radiation, substance P, isoproterenol, methamphetamine and melatonin. Agonists that stabilize IL-1 mRNA include bacterial endotoxin and IL-1. Other agonists, that function by increasing the number of IL-1 type 1 receptors available, include IL-1, PKC activators, dexamethasone, IL-2, IL-4 and PGE2. Other preferred antagonists interfere or inhibit signal transduction factors activated by IL-1 or utilized in an IL-1 signal transduction pathway (e.g NFκB and AP-1, PI3 kinase, phospholipase A2, protein kinase C, JNK-1, 5-lipoxygenase, cyclooxygenase 2, tyrosine phosphorylation, iNOS pathway, Rac, Ras, TRAF). Still other agonists increase the bioactivity of genes whose expression is induced by IL-1, including: IL-1, IL-1Ra, TNF, IL-2, IL-3, IL-6, IL-12, GM-CSF, G-CSF, TGF-β, fibrinogen, urokinase plasminogen inhibitor, Type 1 and type 2 plasminogen activator inhibitor, p-selectin (CD62), fibrinogen receptor, CD-11/CD18, protease nexin-1, CD44, Matrix metalloproteinase-1 (MMP-1),MMP-3, Elastase, Collagenases, Tissue inhibitor of metalloproteinases-1 (TIMP-1),Collagen, Triglyceride increasing Apo CIII, Apolipoprotein, ICAM-1, ELAM-1, VCAM-1, L-selectin, Decorin, stem cell factor, Leukemia inhibiting factor, IFNα, β,γ, L-8, IL-2 receptor, IL-3 receptor, IL-5 receptor, c-kit receptor, GM-CSF receptor, Cyclooxygenase-2 (COX-2), Type 2 phospholipase A2, Inducible nitric oxide synthase (iNOS), Endothelin-1,3, Gamma glutamyl transferase, Mn superoxide dismutase, C-reactive protein, Fibrinogen, Serum amyloid A, Metallothioneins, Ceruloplasmin, Lysozyme, Xanthine dehydrogenase, Xanthine oxidase, Platelet derived growth factor A chain (PDGF), Melanoma growth stimulatory activity (gro-α,β,γ, Insulin-like growth factor-1(IGF-1), Activin A, Pro-opiomelanocortiotropin, corticotropin releasing factor, B amyloid precursor, Basement membrane protein-40, Laminin B1 and B2, Constitutive heat shock protein p70, P42 mitogen, activating protein kinase, ornithine decarboxylase, heme oxygenase and G-protein α subunit).

An "IL-1 antagonist" as used herein refers to an agent that downregulates or otherwise decreases an IL-1 bioactivity. IL-1 antagonists may act on any of a variety of different levels, including regulation of IL-1 gene expression at the promoter region, regulation of mRNA splicing mechanisms, stabilization of mRNA, phosphorylation of proteins for translation, conversion of proIL-1 to mature IL-1 and secretion of IL-1. Antagonists of IL-1production include: corticosteroids, lipoxygenase inhibitors, cyclooxygenase inhibitors, γ-interferon, IL4, IL-10, IL-13, transforming growth factor β (TGF-β), ACE inhibitors, n-3 polyunsaturated fatty acids, antioxidants and lipid reducing agents. Antagonists that destabilize IL-1mRNA include agents that promote deadenylation. Antagonists that inhibit or prevent phosphorylation of IL-1 proteins for translation include pyridinyl-imadazole compounds, such as tebufelone and compounds that inhibit microtubule formation (e.g. colchicine, vinblastine and vincristine). Antagonists that inhibit or prevent the conversion of proIL-1 to mature IL-1 include interleukin converting enzyme (ICE) inhibitors, such as εICE isoforms, ICE α, β, and γ isoform antibodies, CXrm-A, transcript X, endogenous tetrapeptide competitive substrate inhibitor, trypsin, elastase, chymotrypsin, chymase, and other nonspecific proteases. Antagonists that prevent or inhibit the scretion of IL-1 include agents that block anion transport. Antagonists that interefere with IL-1 receptor interactions, include: agents that inhibit glycosylation of the type I IL-1 receptor, antisense oligonucleotides against IL-1RI, antibodies to IL-1RI and antisense oligonucleotides against IL-1RacP. Other antagonists, that function by decreasing the number of IL-1 type 1 receptors available, include TGF-β, COX inhibitors, factors that increase IL-1 type II receptors, dexamethasone, PGE2, IL-1 and IL-4. Other preferred antagonists interfere or inhibit signal transduction factors activated by IL-1 or utilized in an IL-1 signal transduction pathway (e.g NFκB and AP-1, PI3 kinase, phospholipase A2, protein kinase C, JNK-1, 5-lipoxygenase, cyclooxygenase 2, tyrosine phosphorylation, iNOS pathway, Rac, Ras, TRAF). Still other antagonists interfere with the bioactivity of genes whose expression is induced by IL-1, including: IL-1, IL-1Ra, TNF, IL-2, IL-3, IL-6, IL-12, GM-CSF, G-CSF, TGF-β, fibrinogen, urokinase plasminogen inhibitor, Type 1 and type 2 plasminogen activator inhibitor, p-selectin (CD62), fibrinogen receptor, CD-11/CD18, protease nexin-1, CD44, Matrix metalloproteinase-1 (MMP-1),MMP-3, Elastase, Collagenases, Tissue inhibitor of metalloproteinases-1 (TIMP-1),Collagen, Triglyceride increasing Apo CIII, Apolipoprotein, ICAM-1, ELAM-1, VCAM-1, L-selectin, Decorin, stem cell factor, Leukemia inhibiting factor, IFNα,β,γ, L-8, IL-2 receptor, IL-3 receptor, IL-5 receptor, c-kit receptor, GM-CSF receptor, Cyclooxygenase-2 (COX-2), Type 2 phospholipase A2, Inducible nitric oxide synthase (iNOS), Endothelin-1,3, Gamma glutamyl tnansferase, Mn superoxide dismutase, C-reactive protein, Fibrinogen, Serum amyloid A, Metallothioneins, Ceruloplasmin, Lysozyme, Xanthine dehydrogenase, Xanthine oxidase, Platelet derived growth factor A chain (PDGF), Melanoma growth stimulatory activity (gro-α,β,γ), Insulin-like growth factor-1 (IGF-1), Activin A, Pro-opiomelanocortiotropin, corticotropin releasing factor, B amyloid precursor, Basement membrane protein40, Laminin B1 and B2, Constitutive heat shock protein p70, P42 mitogen, activating protein kinase, ornithine decarboxylase, heme oxygenase and G-protein α subunit). Other preferred antagonists include: hymenialdisine, herbimycines (e.g. herbamycin A), CK-103A and its derivatives (e.g. 4,6-dihydropyridazino[4,5-c]pyridazin-5 (1H)-one), CK-119, CK-122, iodomethacin, aflatoxin B1, leptin, heparin, bicyclic imidazoles (e.g SB203580), PD15306 HCl, podocarpic acid derivatives, M-20, Human [Gly2] Glucagon-like peptide-2, FR167653, Steroid derivatives, glucocorticoids, Quercetin, Theophylline, NO-synthetase inhibitors, RWJ 68354, Euclyptol (1.8-cineole), Magnosalin, N-Acetylcysteine, Alpha-Melatonin-Stimulating Hormone (α-MSH), Triclosan (2,4,4'-trichloro-2'-hydroxyldiphenyl ether), Prostaglandin E2 and 4-aminopyridine Ethacrynic acid and 4,4'-diisothiocyanatostilbene-2,2'-disulfonic acid (DIDS), Glucose, Lipophosphoglycan, aspirin, Catabolism-blocking agents, Diacerhein, Thiol-modulating agents, Zinc, Morphine, Leukotriene biosynthesis inhibitors (e.g. MK886), Platelet-activating factor receptor antagonists (e.g. WEB 2086), Amiodarone, Tranilast, S-methyl-L-thiocitrulline, Beta-adrenoreceptor agonists (e.g. Procaterol, Clenbuterol, Fenoterol, Terbutaline, Hyaluronic acid, anti-TNF-α antibodies, anti-IL-1α autoantibodies, IL-1 receptor antagonist, IL-1R-associated kinase, soluble TNF receptors and antiinflamatory cytokines (e.g IL4, IL-13, IL-10, IL-6, TGFβ, angiotensin II, Soluble IL-1 type II receptor, Soluble IL-1 type I receptor, Tissue plasminogen activator, Zinc finger protein A20 IL-1 Peptides (e.g (Thr-Lys-Pro-Arg) (Tufisin), (Ile-Thr-Gly-Ser-Glu) IL-1-alpha, Val-Thr-Lys-Phe-Tyr-Phe, Val-Thr-Asp-Phe-Tyr-Phe, Interferon alpha2b, Interferon beta, IL-1-beta analogues (e.g. IL-1-beta tripeptide:

Lys-D-Pro-Thr), glycosylated IL-1-alpha, and IL-1ra peptides.

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al, *Genomics* 19: 382–84, 1994). The terms "IL-1A", "IL-1B", and "IL-1RN" as used herein refer to the genes coding for IL-1, IL-1, and IL-1 receptor antagonist, respectively. The gene accession number for IL-1A, IL-1B, and IL-1RN are X03833, X04500, and X64532, respectively.

"IL-1 functional mutation" refers to a mutation within the IL-1 gene cluster that results in an altered phenotype (i.e. effects the function of an IL-1 gene or protein). Examples include: IL-1A(+4845) allele 2, IL-1B (+3954) allele 2, IL-1B (+6912) allele 2 and IL-1RN (+2018) allele 2.

"IL-1X (Z) allele Y" refers to a particular allelic form, designated Y, occurring at an IL-1 locus polymorphic site in gene X, wherein X is IL-1A, B, or RN or some other gene in the IL-1 gene loci, and positioned at or near nucleotide Z, wherein nucleotide Z is numbered relative to the major transcriptional start site, which is nucleotide +1, of the particular IL-1 gene X. As further used herein, the term "IL-1X allele (Z)" refers to all alleles of an IL-1 polymorphic site in gene X positioned at or near nucleotide Z. For example, the term "IL-1RN(+2018) allele" refers to alterative forms of the IL-1RN gene at marker+2018. "IL-1RN (+2018) allele 1" refers to a form of the IL-1RN gene which contains a cytosine (C) at position +2018 of the sense strand. Clay et al., *Hum. Genet.* 97:723–26, 1996. "IL-1RN (+2018) allele 2" refers to a form of the IL-1RN gene which contains a thymine (T) at position +2018 of the plus strand. When a subject has two identical IL-1RN alleles, the subject is said to be homozygous, or to have the homozygous state. When a subject has two different IL-1RN alleles, the subject is said to be heterozygous, or to have the heterozygous state. The term "IL-1RN (+2018) allele 2,2" refers to the homozygous IL-1 RN (+2018) allele 2 state. Conversely, the term "IL-1RN (+2018) allele 1,1" refers to the homozygous IL-1RN (+2018) allele 1 state. The term "IL-1RN (+2018) allele 1,2"refers to the heterozygous allele 1 and 2 state.

"IL-1 related" as used herein is meant to include all genes related to the human IL-1 locus genes on human chromosome 2 (2q 12–14). These include IL-1 genes of the human IL-1 gene cluster located at chromosome 2 (2q 13–14) which include: the IL-1A gene which encodes interleukin-1α, the IL-1B gene which encodes interleukin-1β, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1α, interleukin-1β, and interleukin-1RN are related in so much as they all bind to IL-1 type I receptors, however only interleukin-1α and interleukin-1β are agonist ligands which activate IL-1 type I receptors, while interleukin-1RN is a naturally occurring antagonist ligand.

Where the term "IL-1" is used in reference to a gene product or polypeptide, it is meant to refer to all gene products encoded by the interleukin-1 locus on human chromosome 2 (2q 12–14) and their corresponding homologs from other species or functional variants thereof. The term IL-1 thus includes secreted polypeptides which promote an inflammatory response, such as IL-1α and IL-1β, as well as a secreted polypeptide which antagonize inflammatory responses, such as IL-1 receptor antagonist and the IL-1 type II (decoy) receptor.

An "IL-1 receptor" or "IL-1R" refers to various cell membrane bound protein receptors capable of binding to and/or transducing a signal from IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

An "IL-1 polypeptide" and "IL-1 protein" are intended to encompass polypeptides comprising the amino acid sequence encoded by the IL-1 genomic DNA sequences shown in FIGS. 1, 2, and 3, or fragments thereof, and homologs thereof and include agonist and antagonist polypeptides.

"In-stent stenosis" refers to the progressive occlusion within a stent that has been placed during angioplasty. In-stent stenosis is a form of restenosis that takes place within an arterial stent.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

The term "interact" as used herein is meant to include detectable relationships or associations (e.g. biochemical interactions) between molecules, such as interactions between protein-protein, protein-nucleic acid, nucleic acid-nucleic acid and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g, based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell. In a simple example, the knock-out construct is comprised of a gene, such as the IL-1RN gene, with a deletion in a critical portion of the gene so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker (such as the neo gene) so that the gene can be represented as follows: IL-1RN 5'/neo/IL-1RN 3', where IL-1RN5' and IL-1RN 3', refer to genomic or cDNA sequences which are, respectively, upstream and downstream relative to a portion of the IL-1RN gene and where neo refers to a neomycin resistance gene. In another knock-out construct, a second selectable marker is added in a flanking position so that the gene can be represented as: IL-1RN/neo/EL-1RN/TK, where TK is a thymidine kinase gene which can be added to either the IL-1RN5' or the IL-1RN3' sequence of the preceding construct and which further can be selected against (i.e. is a negative selectable marker) in appropriate media This two-marker construct allows the selection of homologous recombination events, which removes the flanking TK marker, from non-homologous recombination events which typically retain the TK sequences. The gene deletion and/or replacement can be from the exons, introns, especially intron junctions, and/or the regulatory regions such as promoters.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage equilibrium". The cause of linkage disequilibrium is often unclear. It can be due to selection for certain allele combinations or to recent admixture of genetically heterogeneous populations. In addition, in the case of markers that are very tightly linked to a disease gene, an association of an allele (or group of linked alleles) with the disease gene is expected if the disease mutation occurred in the recent past, so that sufficient time has not elapsed for equilibrium to be achieved through recombination events in the specific chromosomal region. When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern. An example of linkage disequilibrium is that which occurs between the alleles at the IL-1RN (+2018) and IL-1RN (VNTR) polymorphic sites. The two alleles at IL-1RN (+2018) are 100% in linkage disequilibrium with the two most frequent alleles of IL-1RN (VNTR), which are allele 1 and allele 2.

The term "marker" refers to a sequence in the genome that is known to vary among individuals. For example, the IL-1RN gene has a marker that consists of a variable number of tandem repeats (VNTR).

"Modulate" refers to the ability of a substance to regulate bioactivity. When applied to an IL-1 bioactivity, an agonist or antagonist can modulate bioactivity for example by agonizing or antagonizing an IL-1 synthesis, receptor interaction, or IL-1 mediated signal transduction mechanism.

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

A "non-human animal" of the invention includes mammals such as rodents, non-human primates, sheep, dogs, cows, goats, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any members of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

"Occlusive disorder" refers to that cardiovascular disorder characterized by the progressive thickening of an arterial wall, associated with the presence of an atherosclerotic intimal lesion within an artery. Occlusive disorder leads to progressive blockage of the artery. With sufficient progression, the occlusive disorder can reduce flow in the artery to the point that clinical signs and symptoms are produced in the tissues perfused by the artery. These clinical events relate to ischemia of the perfused tissues. When severe, ischemia is accompanied by tissue death, called infarction or gangrene. Occlusive disorder is associated with the allele pattern 2 s at the IL-1 locus. An "occlusive disorder therapeutic" refers to any agent or therapeutic regimen (including pharmaceuticals, nutraceuticals and surgical means) that prevents or postpones the development of or reduces the extent of an abnormality constitutive of an occlusive disorder in a subject. Examples of occlusive disorder therapeutics include those agents that are antioxidants, those that lower serum lipids, those that block the action of oxidized lipids and other agents that influence lipid metabolism or otherwise have lipid-active effects.

A "peripheral vascular disease" ("TVD") is a cardiovascular disease resulting from the blockage of the peripheral (i.e., non-coronary) arteries. Blockage can occur suddenly, by mechanisms such as plaque rupture or embolization, as occurs in fragile plaque disease. Blockage can occur progressively, with narrowing of the artery via myointimal hyperplasia and plaque formation, as in occlusive disease. Blockage can be complete or partial. Those clinical signs and symptoms resulting from the blockage of peripheral arteries are manifestations of peripheral vascular disease. Manifestations of peripheral vascular diseases include, inter alia, claudication, ischemia, intestinal angina, vascular-based renal insufficiency, transient ischemic attacks, aneurysm formation, peripheral embolization and stroke. Ischemic cerebrovascular disease is a type of peripheral vascular disease. The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The term "propensity to disease," also "predisposition" or "susceptibility" to disease or any similar phrase, means that certain alleles are hereby discovered to be associated with or predictive of ILD. The alleles are thus over-represented in frequency in individuals with disease as compared to healthy individuals. Thus, these alleles can be used to predict disease even in pre-symptomatic or pre-diseased individuals.

The term "restenosis" refers to any preocclusive lesion that develops following a reconstructive procedure in a diseased blood vessel. The term is not only applied to the recurrence of a pre-existing stenosis, but also to previously normal vessels such as vein grafts that become partially occluded following vascular bypass. Restenosis refers to any luminal narrowing that occurs following an injury to the vessel wall. Injuries resulting in restenosis can therefore include trauma to an atherosclerotic lesion (as seen with angioplasty), a resection of a lesion (as seen with endarterectomy), an external trauma (e.g., a cross-clamping injury), or a surgical anastomosis. Restenosis typically results from a hyperplasia.

Restenosis can occur as the result of any kind of vascular reconstruction, whether in the coronary vasculature or in the periphery (Colbum and Moore (1998) Myointimal Hyperplasia pp. 690–709 in Vascular Surgery: A Comprehensive Review (Philadelphia: Saunders, 1998)). For example, studies have reported symptomatic restenosis rates of 30–50% following coronary angioplasties (see Berk and Harris (1995) Adv. Intem. Med. 40:455–501). After carotid endarterectomies, as a further example, 20% of patients studied had a luminal narrowing greater than 50% (Clagett et al. (1986) J. Vasc. Surg. 3:10–23). Yet another example of restenosis is seen in infrainguinal vascular bypasses, where 40–60% of prosthetic grafts and 20–40% of the vein grafts are occluded at three years (Dalman and Taylor (1990) Ann. Vasc. Surg. 3:109–312, Szilagyi et al. (1973) Ann. Surg. 178:232–246). Different degrees of symptomatology accompany preocclusive lesions in different anatomical locations, due to a combination of factors including the different calibers of the vessels involved, the extent of residual disease and local hemodynamics.

A "restenosis associated allele" refers to an allele whose presence in a subject indicates that the subject has or is susceptible to developing a restenosis. Examples of restenosis associated alleles include allele 1 of the +4845 marker of IL-1A; allele 1 of the +3954 marker of IL-1B ; allele 1 of the −511 marker of IL-1B; and allele 1 of the +2018 marker of L-1RN. Still other linked polymorphic loci associated with restenosis include: the IL-1RN(VNTR) polymorphism, the IL-1RN gene +1731 polymorphism; the IL-1RN gene +1812 polymorphism; the IL-1RN gene +1868 polymorphism; the IL-1RN gene +1887 polymorphism; the IL-1RN +8006 polymorphism, the IL-1RN +8061 polymorphism, the IL-1B −31 polymorphism and the IL-1B −511 polymorphism. Other restenosis associated alleles that have been described in the art include certain alleles in angiotensin converting enzymes (See e.g. Kasi et al., (1996) Am. J. Cardiol. 77: 875–77).

A "restenosis causative functional mutation" refers to a mutation which causes or contributes to the development of restenosis in a subject. Preferred mutations occur within the IL-1 complex. A restenosis causative functional mutation occurring within an IL-1 gene (e.g. IL-1A, IL-1B or IL-1RN) or a gene locus, which is linked thereto, may alter, for example, the open reading frame or splicing pattern of the gene, thereby resulting in the formation of an inactive or hypoactive gene product. For example, a mutation which occurs in intron 6 of the IL-1A locus corresponds to a variable number of tandem repeat 46 bp sequences corresponding to from five to 18 repeat units (Bailly, et al. (1993) Eur. J. Immunol. 23: 1240–45). These repeat sequences contain three potential binding sites for transcriptional factors: an SP1 site, a viral enhancer element, and a glucocorticoid-responsive element; therefore individuals carrying IL-1A intron 6 VNTR alleles with large numbers of repeat units may be subject to altered transcriptional regulation of the IL-1A gene and consequent perturbations of inflammatory cytokine production. Indeed, there is evidence that increased repeat number at this polymorphic IL-1A locus leads to decreased IL-1α synthesis (Bailly et al. (1996) Mol Immunol 33: 999–1006). Alternatively, a mutation can result in a hyperactive gene product. For example, allele 2 of the IL-1B (G at +6912) polymorphism occurs in the 3' UTR (untranslated region) of the IL-1B mRNA and is associated with an approximately four-fold increase in the steady state levels of both IL-1B mRNA and IL-1B protein compared to those levels associated with allele 1 of the IL-1B gene© at +6912). Further, an IL-1B (−511) mutation occurs near a promoter binding site for a negative glucocorticoid response element (Zhang et al. (1997) DNA Cell Biol 16: 145–52). This element potentiates a four-fold repression of IL-1B expression by dexamethosone and a deletion of this negative response elements causes a 2.5-fold increase in IL-1B promoter activity. The IL-1B (−511) polymorphism may thus directly affect cytokine production and inflammatory responses. These examples demonstrate that genetic variants occurring in the IL-1A or IL-1B gene can directly lead to the altered production or regulation of IL-1 cytokine activity.

A "restenosis therapeutic" refers to any agent or therapeutic regimen (including pharmaceuticals, nutraceuticals and surgical means) that prevents or postpones the development of or alleviates the symptoms of a restenosis in a subject. A restenosis therapeutic can be a polypeptide, peptidomimetic, nucleic acid or other inorganic or organic molecule, preferably a "small molecule" including vitamins, minerals and other nutrients. Preferably a restenosis therapeutic can modulate at least one activity of an IL-1 polypeptide, e.g., interaction with a receptor, by mimicking or potentiating (agonizing) or inhibiting (antagonizing) the effects of a naturally-occurring polypeptide. An agonist can be a wild-type protein or derivative thereof having at least one bioactivity of the wild-type, e.g., receptor binding activity. An agonist can also be a compound that upregulates expression of a gene or which increases at least one bioactivity of a protein. An agonist can also be a compound which increases the interaction of a polypeptide with another molecule, e.g., a receptor. An antagonist can be a compound which inhibits or decreases the interaction between a protein and another molecule, e.g., a receptor or an agent that blocks signal transduction or post-translation processing (e.g., IL-1 converting enzyme (ICE) inhibitor). Accordingly, a preferred antagonist is a compound which inhibits or decreases binding to a receptor and thereby blocks subsequent activation of the receptor. An antagonist can also be a compound that downregulates expression of a gene or which reduces the amount of a protein present. The antagonist can be a dominant negative form of a polypeptide, e.g., a form of a polypeptide which is capable of interacting with a target peptide, e.g., a receptor, but which does not promote the activation of the receptor. The antagonist can also be a nucleic acid encoding a dominant negative form of a polypeptide, an antisense nucleic acid, or a ribozyme capable of interacting specifically with an RNA. Yet other antagonists are molecules which bind to a polypeptide and inhibit its action. Such molecules include peptides, e.g., forms of target peptides which do not have biological activity, and which inhibit binding to receptors. Thus, such peptides will bind to the active site of a protein and prevent it from interacting with target peptides. Yet other antagonists include antibodies that specifically interact with an epitope of a molecule, such that binding interferes with the biological function of the polypeptide. In yet another preferred embodiment, the antagonist is a small molecule, such as a molecule capable of inhibiting the interaction between a polypeptide and a target receptor. Alternatively, the small molecule can function as an antagonist by interacting with sites other than the receptor binding site. Preferred restenosis therapeutics include agents that suppress the development of neointimal hyperplasia, including lipid lowering drugs, anti-platelet agents, anti-inflammatory agents, antihypertensive agents and anticoagulants; and agents that directly inhibit cellular growth. Furthermore, surgical decisions at the time of the primary procedure or at the time of a secondary surgical operation could differ depending on whether the patient was at higher risk for a more prolific inflammation-mediated injury response. The decision to employ a stent as part of an endovascular procedure could be governed, for example, by an awareness of a patient's higher risk for more aggressive vascular response to injury.

A "risk factor" is a factor identified to be associated with an increased risk. A risk factor for a cardiovascular disorder or a cardiovascular disease is any factor identified to be associated with an increased risk of developing those conditions or of worsening those conditions. A risk factor can also be associated with an increased risk of an adverse clinical event or an adverse clinical outcome in a patient with a cardiovascular disorder. Risk factors for cardiovascular disease include smoking, adverse lipid profiles, elevated lipids or cholesterol, diabetes, hypertension, hypercoagulable states, elevated homocysteine levels, and lack of exercise. Carrying a particular polymorphic allele is a risk factor for a particular cardiovascular disorder, and is associated with an increased risk of the particular disorder.

"Small molecule" as used herein, is meant to refer to a composition, which has a molecular weight of less than about 5 kD and most preferably less than about 4 kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule to hybridize to at least approximately 6 consecutive nucleotides of a sample nucleic acid.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transgenic" means a nucleic acid sequence (encoding, e.g., one of the IL-1 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of an IL-1 polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques. The term is intended to include all progeny generations. Thus, the founder animal and all F1, F2, F3, and so on, progeny thereof are included.

The term "treating" as used herein is intended to encompass curing as well as ameliorating at least one symptom of a disease or at least one abnormality associated with a disorder. Treating a cardiovascular disorder can take place by administering a cardiovascular disorder therapeutic. Treating a cardiovascular disorder can also take place by modifying risk factors that are related to the cardiovascular disorder.

A "treatment plan" refers to at least one intervention undertaken to modify the effect of a risk factor upon a patient. A treatment plan for a cardiovascular disorder or disease can address those risk factors that pertain to cardiovascular disorders or diseases. A treatment plan can include an intervention that focuses on changing patient behavior, such as stopping smoking. A treatment plan can include an intervention whereby a therapeutic agent is administered to a patient. As examples, cholesterol levels can be lowered with proper medication, and diabetes can be controlled with insulin. Nicotine addiction can be treated by withdrawal medications. A treatment plan can include an intervention that is diagnostic. The presence of the risk factor of hypertension, for example, can give rise to a diagnostic intervention whereby the etiology of the hypertension is determined. After the reason for the hypertension is identified, further treatments may be administered.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.2 Predictive Medicine

4.2.1. Polymorphisms Associated with Restenosis

Figure 4:
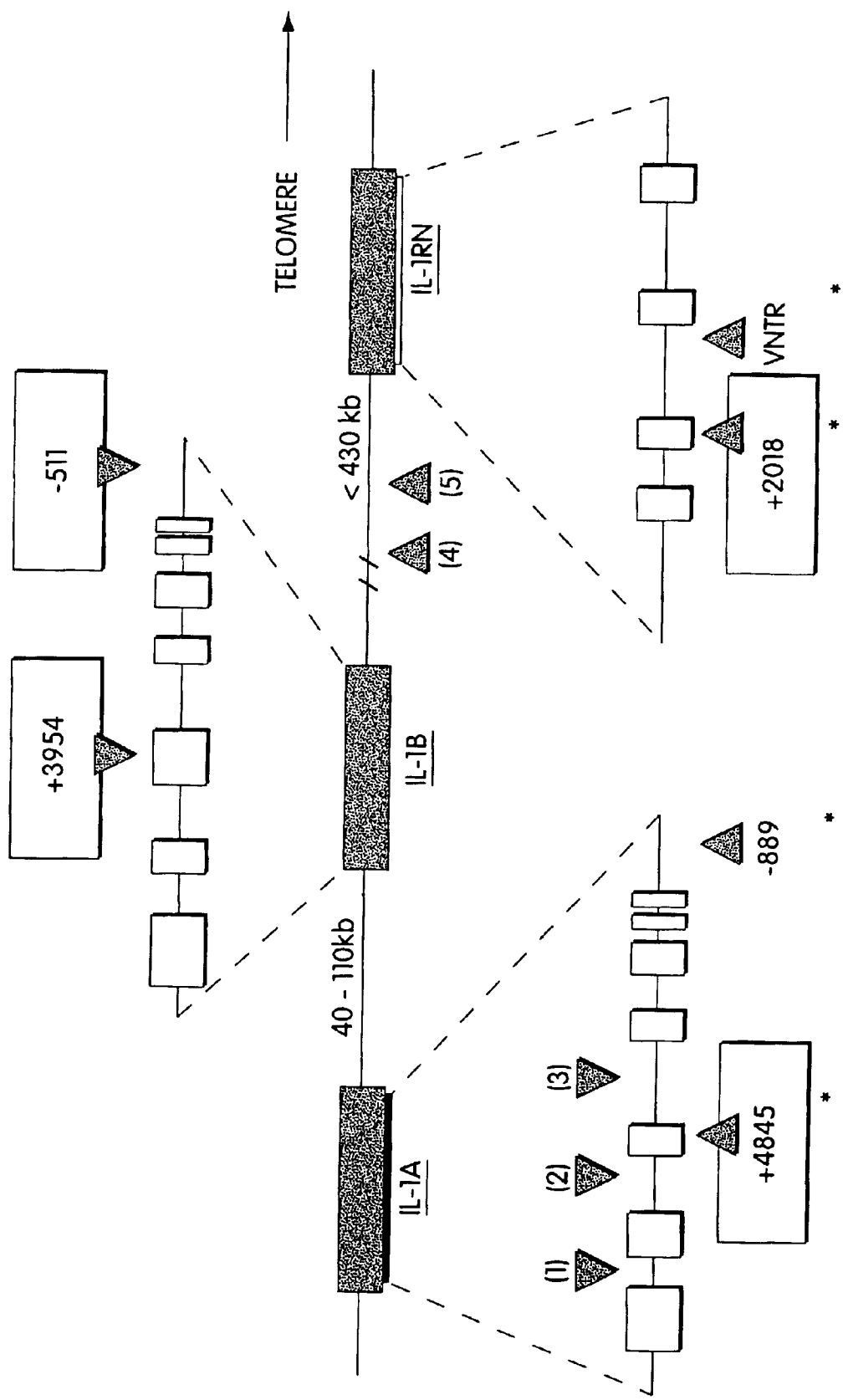
FIG. 4 depicts the organization of the IL-1 genes, and associated polymorphic loci, on human chromosome 2.
Figure 5:
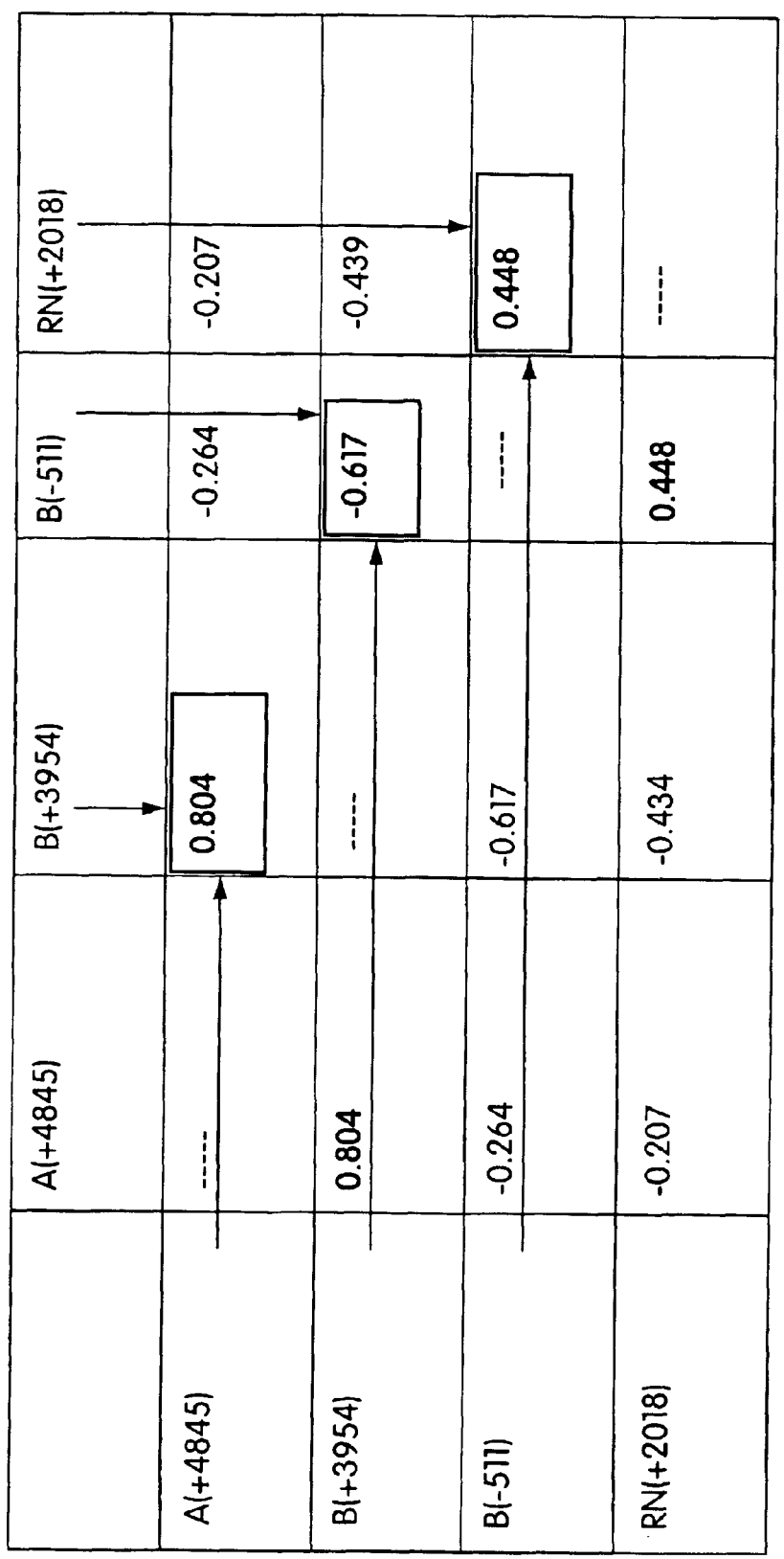
FIG. 5 shows linkage disequilibrium values for the IL-1 polymorphic loci in a Caucasian population.
Figure 6:
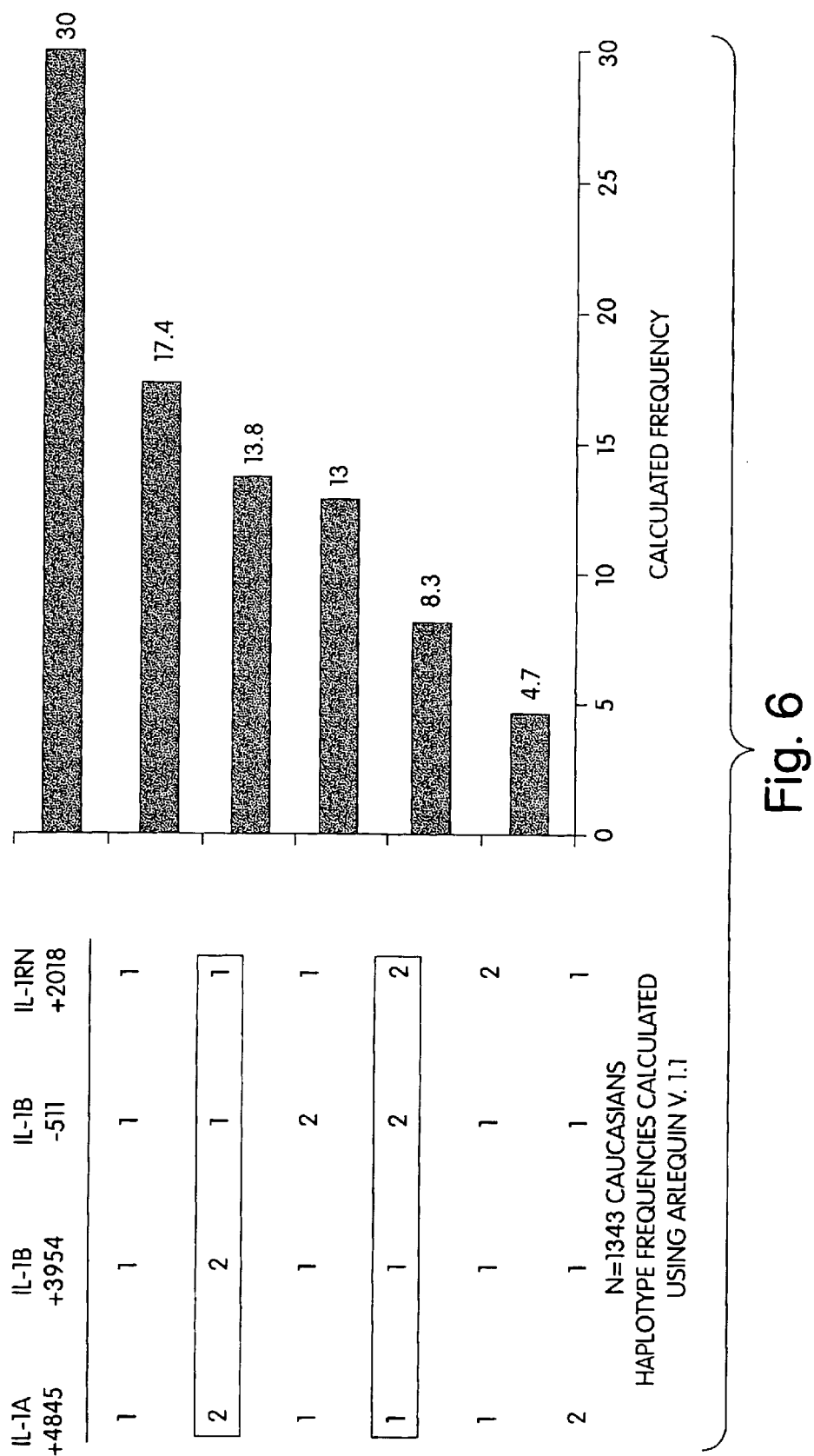
FIG. 6 is a bar graph illustrating the frequency of particular IL-1 polymorphic allelic patterns in a Caucasian population.

The present invention is based at least in part, on the identification of alleles that are associated (to a statistically significant extent) with the development of a restenosis in subjects. Therefore, detection of these alleles, alone or in conjunction with another means in a subject indicate that the subject has or is predisposed to the development of a restenosis. For example, IL-1 polymorphic alleles which are associated with a propensity for developing restenosis include allele 1 of each of the following markers: IL-1A (+4845), IL-1B (+3954), IL-1B (−511), IL-1RN (+2018) and IL-1RN (VNTR) or an allele that is in linkage disequilibrium with one of the aforementioned alleles. In particularly preferred embodiments, the presence of a particular allelic pattern of one or more of the abovementioned IL-1 polymorphic loci is used to predict the susceptibility of an individual to developing restenosis. In particular, there are three patterns of alleles at four polymorphic loci in the IL-1 gene cluster that show various associations with particular cardiovascular disorders. These patterns are referred to herein as patterns 1, 2 and 3. Pattern 1 comprises an allelic pattern including allele 2 of IL-1A (+4845) or IL-1B (+3954) and allele 1 of IL-1B (−511) or IL-1RN (+2018), or an allele that is in linkage disequilibrium with one of the aforementioned allele. In a preferred embodiment, this allelic pattern permits the diagnosis of fragile plaque disorder. Pattern 2 comprises an allelic pattern including allele 2 of IL-1B (511) or IL-1RN (+2018) and allele 1 of IL-1A (+4845) or IL-1B (+3954), or an allele that is in linkage disequilibrium with one of the aforementioned alleles. In a preferred embodiment, this allelic pattern permits the diagnosis of occlusive cardiovascular disorder. Pattern 3 comprises an allelic pattern including allele 1 of IL-1A (+4845) or allele 1 of IL-1B (+3954), and allele 1 of IL-1B (−511) or allele 1 of IL-1RN (+2018), or an allele that is in linkage disequilibrium with one of the aforementioned alleles. In a preferred embodiment, this allelic pattern permits the diagnosis of a restenosis disorder These IL-1 locus polymorphisms represent single base variations within the IL-1A/IL-1B/IL-1RN gene cluster (see FIG. 4). The IL-1A (+4845) polymorphism is a single base variation (allele 1 is G, allele 2 is T) at position +4845 within Exon V of the IL-1A gene which encodes the inflammatory cytokine IL-1a (Gubler, et al.(1989) Interleukin, inflammation and disease (Bomford and Henderson, eds.) p.31–45, Elsevier publishers; and Van den velden and Reitsma (1993) Hum Mol Genetics 2:1753–50). The IL-1A (+4845) polymorphism occurs in the coding region of the gene and results in a single amino acid variation in the encoded protein (Van den Velden and Reitsma (1993) Hum Mol Genet 2: 1753). The IL-1B (−511) polymorphism is a single base pair variation (allele 1 is C, allele 2 is T) which occurs 511 base pairs upstream of the site of IL-1B gene transcription initiation (Di Giovine et al. (1992) Hum Mol Genet 1: 450). The IL-1B (+3954) polymorphism was first described as a Taq I restriction fragment length polymorphism (RFLP) (Pociot et al. (1992) Eur J Clin Invest 22: 396–402) and has subsequently been characterized as a single base variation (allele 1 is C, allele 2 is T) at position +3954 in Exon V of the IL-1B gene (di Giovine et al. (1995) Cytokine 7: 600–606). This single nucleotide change in the open reading frame of IL-1B does not appear to qualitatively affect the sequence of the encoded IL-1 beta polypeptide because it occurs at the third position of a TTC phenylalanine codon (F) of allele 1 and therefore allele 2 merely substitutes a TTT phenylalanine codon at this position which encodes amino acid 105 of the IL-1B gene product. Finally, the IL-RN variable number of tandem repeats (VNTR) polymorphism occurs within the second intron the IL-1 receptor antagonist encoding gene (Steinkasserer (1991) Nucleic Acids Res 19: 5090–5). Allele 2 of the of the IL-1RN (VNTR) polymorphism corresponds to two repeats of an 86-base pair sequence, while allele 1 corresponds to four repeats, allele 3 to three repeats, allele 4 to five repeats, and allele 5 to six repeats (Tarlow et al. (1993) Hum Genet 91: 403–4). Detection of any one of these IL-1 allelic variants in an individual suggests an increased likelihood of developing restenosis in comparison to a control individual who does not carry the allele 2 variant at the same locus.

However, because these alleles are in linkage disequilibrium with other alleles, the detection of such other linked alleles can also indicate that the subject has or is predisposed to the development of a restenosis. For example, the following alleles of the IL-1 (33221461) haplotype are in linkage disequilibrium:

> allele 3 of the 222/223 marker of IL-1A
> allele 3 of the gz5/gz6 marker of IL-1A
> allele 2 of the −889 marker of IL-1A
> allele 2 of the +3954 marker of IL-1B
> allele 1 of the −511 marker of IL-1B
> allele 4 of the gaat.p33330 marker -continued > allele 6 of the Y31 marker
> allele 1 of the VNTR or (+2018) marker of IL-1RN Therefore, allele 1 of IL-1B (−511) and allele 1 of IL-1RN (VNTR) are in strong linkage disequilibrium with one another and each of these is in linkage disequilibrium with allele 1 of the −511 marker of IL-1B. Furthermore, in alternative embodiments of the present invention, genotyping analysis at the 222/223 marker of IL-1A, the gz5/gz6 marker of IL-1A, the −889 marker of IL-1A, the +3954 marker of IL-1B, the gaat.p33330 marker of the IL-1B/IL-1RN intergenic region, or the Y31 marker of the IL-1B/IL-1RN intergenic region is determined, and the presence of a polymorphic allele which is linked to one or more of the preferred restenosis-predictive alleles is detected.

In addition, allele 1 of the IL-1RN (+2018) polymorphism (Clay et al. (1996) Hum Genet 97: 723–26), also referred to as exon 2 (8006) (GenBank:X64532 at 8006) is known to be in linkage disequilibrium with allele 1 of the IL-1RN (VNTR) polymorphic locus, which in turn is a part of the 33221461 human haplotype. In contrast, allele 2 of the IL-1RN (+2018) locus (i.e. C at +2018), is an allelic variant associated with the 44112332 haplotype and allele 2 of the IL-1RN (VNTR) polymorphic locus. The IL-1RN (VNTR) therefore provides an alternative target for prognostic genotyping analysis to determine an individual's likelihood of developing restenosis. Similarly, three other polymorphisms in an IL-1RN alternative exon (Exon 1ic, which produces an intracellular form of the gene product) are also in linkage disequilibrium with allele 2 of IL-1RN (VNTR) (Clay et al. (1996) Hum Genet 97: 723–26). These include: the IL-1RN exon 1 ic (1812) polymorphism (GenBank:X77090 at 1812); the IL-1RN exon 1ic (1868) polymorphism (GenBank:X77090 at 1868); and the IL-1RN exon 1ic (1887) polymorphism (GenBank:X77090 at 1887). Furthermore yet another polymorphism in the promoter for the alternatively spliced intracellular form of the gene, the Pic (1731) polymorphism (GenBank:X77090 at 1731), is also in linkage disequilibrium with allele 2 of the IL-1RN (VNTR) polymorphic locus (Clay et al. (1996) Hum Genet 97: 723–26). The corresponding sequence alterations for each of these IL-1RN polymorphic loci is shown below.

| Allele # | Exon 2 (+2018 of IL-1RN) | Exon 1ic-1 (1812 of GB: X77090) | Exon 1ic-2 (1868 of GB: X77090) | Exon 1ic-3 (1887 of GB: X77090) | Pic (1731 of GB: X77090) |
|---|---|---|---|---|---|
| 1 | T | G | A | G | G |
| 2 | C | A | G | C | A |

For each of these polymorphic loci, the allele 1 sequence variant has been determined to be in linkage disequilibrium with allele 1 of the IL-1RN (VNTR) locus (Clay et al. (1996) Hum Genet 97: 723–26).

Further, allele 1 of IL-1B (+3954), which has been pointed out as a prognostic indicator of an increased propensity for developing restenosis is a component of a second haplotype, the 44112332 haplotype of co-inherited IL-1 locus polymorphic alleles (Cox, et al. (1998) Am. J. Hum. Genet. 62: 1180–88). Specifically, the 44112332 haplotype comprises the following genotype:

allele 4 of the 222/223 marker of IL-1A
allele 4 of the gz5/gz6 marker of IL-1A
allele 1 of the −889 marker of IL-1A
allele 1 of the +3954 marker of IL-1B
allele 2 of the −511 marker of IL-1B
allele 3 of the gaat.p33330 marker
allele 3 of the Y31 marker
allele 2 of the VNTR marker of IL-1RN In addition to the allelic patterns described above, as described herein, one of skill in the art can readily identify other alleles (including polymorphisms and mutations) that are in linkage disequilibrium with an allele associated with restenosis. For example, a nucleic acid sample from a first group of subjects without restenosis can be collected, as well as DNA from a second group of subjects with restenosis. The nucleic acid sample can then be compared to identify those alleles that are over-represented in the second group as compared with the first group, wherein such alleles are presumably associated with restenosis. Alternatively, alleles that are in linkage disequilibrium with a restenosis associated allele can be identified, for example, by genotyping a large population and performing statistical analysis to determine which alleles appear more commonly together than expected. Preferably the group is chosen to be comprised of genetically related individuals. Genetically related individuals include individuals from the same race, the same ethnic group, or even the same family. As the degree of genetic relatedness between a control group and a test group increases, so does the predictive value of polymorphic alleles which are ever more distantly linked to a disease-causing allele. This is because less evolutionary time has passed to allow polymorphisms which are linked along a chromosome in a founder population to redistribute through genetic cross-over events. Thus race-specific, ethnic-specific, and even family-specific diagnostic genotyping assays can be developed to allow for the detection of disease alleles which arose at ever more recent times in human evolution, e.g., after divergence of the major human races, after the separation of human populations into distinct ethnic groups, and even within the recent history of a particular family line.

Linkage disequilibrium between two polymorphic markers or between one polymorphic marker and a disease-causing mutation is a meta-stable state. Absent selective pressure or the sporadic linked reoccurrence of the underlying mutational events, the polymorphisms will eventually become disassociated by chromosomal recombination events and will thereby reach linkage equilibrium through the course of human evolution. Thus, the likelihood of finding a polymorphic allele in linkage disequilibrium with a disease or condition may increase with changes in at least two factors: decreasing physical distance between the polymorphic marker and the disease-causing mutation, and decreasing number of meiotic generations available for the dissociation of the linked pair. Consideration of the latter factor suggests that, the more closely related two individuals are, the more likely they will share a common parental chromosome or chromosomal region containing the linked polymorphisms and the less likely that this linked pair will have become unlinked through meiotic cross-over events occurring each generation. As a result, the more closely related two individuals are, the more likely it is that widely spaced polymorphisms may be co-inherited. Thus, for individuals related by common race, ethnicity or family, the reliability of ever more distantly spaced polymorphic loci can be relied upon as an indicator of inheritance of a linked disease-causing mutation.

Appropriate probes may be designed to hybridize to a specific gene of the IL-1 locus, such as IL-1A, IL-1B or IL-1RN or a related gene. These genomic DNA sequences are shown in FIGS. 1, 2 and 3, respectively, and further correspond to formal SEQ ID Nos. 15, 16 to and 17, respectively. Alternatively, these probes may incorporate other regions of the relevant genomic locus, including intergenic sequences. Indeed the IL-1 region of human chromosome 2 spans some 400,000 base pairs and, assuming an average of one single nucleotide polymorphism every 1,000 base pairs, includes some 400 SNPs loci alone. Yet other polymorphisms available for use with the immediate invention are obtainable from various public sources. For example, the human genome database collects intragenic SNPs, is searchable by sequence and currently contains approximately 2,700 entries (http://hgbase.interactiva.de). Also available is a human polymorphism database maintained by the Massachusetts Institute of Technology (MIT SNP database (http://www.genome.wi.mit.edu/SNP/humai/index.html)). From such sources SNPs as well as other human polymorphisms may be found.

For example, examination of the IL-1 region of the human genome in any one of these databases reveals that the IL-1 locus genes are flanked by a centromere proximal polymorphic marker designated microsatellite marker AFM220ze3 at 127.4 cM (centiMorgans) (see GenBank Acc. No. Z17008) and a distal polymorphic marker designated microsatellite anchor marker AFM087xa1 at 127.9 cM (see GenBank Acc. No. Z16545). These human polymorphic loci are both CA dinucleotide repeat microsatellite polymorphisms, and, as such, show a high degree of heterozygosity in human populations. For example, one allele of AFM220ze3 generates a 211 bp PCR amplification product with a 5' primer of the sequence TGTACCTAAGCCCACCCTT-TAGAGC (SEQ ID No. 18) and a 3' primer of the sequence TGGCCTCCAGAAAC-CTCCAA (SEQ ID No. 19). Furthermore, one allele of AFM087xa1 generates a 177 bp PCR amplification product with a 5' primer of the sequence GCTGATATTCTGGTGG-GAAA (SEQ ID No.20) and a 3' primer of the sequence GGCAAGAGCAAAACTCTGTC (SEQ ID No.21). Equivalent primers corresponding to unique sequences occurring 5' and 3' to these human chromosome 2 CA dinucleotide repeat polymorphisms will be apparent to one of skill in the art. Reasonable equivalent primers include those which hybridize within about 1 kb of the designated primer, and which further are anywhere from about 17 bp to about 27 bp in length. A general guideline for designing primers for amplification of unique human chromosomal genomic sequences is that they possess a melting temperature of at least about 50° C., wherein an approximate melting temperature can be estimated using the formula $T_{melt}=[2\times(\# \text{ of A or T})+4\times(\# \text{ of G or C})]$.

A number of other human polymorphic loci occur between these two CA dinucleotide repeat polymorphisms and provide additional targets for determination of a restenosis prognostic allele in a family or other group of genetically related individuals. For example, the National Center for Biotechnology Information web site (www.ncbi.nlm.nih.gov/genemap/) fists a number of polymorphism markers in the region of the IL-1 locus and provides guidance in designing appropriate primers for amplification and analysis of these markers.

Accordingly, the nucleotide segments of the invention may be used for their ability to selectively form duplex molecules with complementary stretches of human chromosome 2 q 12–13 or cDNAs from that region or to provide primers for amplification of DNA or cDNA from this region. The design of appropriate probes for this purpose requires consideration of a number of factors. For example, fragments having a length of between 10, 15, or 18 nucleotides to about 20, or to about 30 nucleotides, will find particular utility. Longer sequences, e.g., 40, 50, 80, 90, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe. Furthermore, depending on the application envisioned, one will desire to employ varying conditions of hybridization to achieve varying degrees of selectivity of probe towards target sequence. For applications requiring high selectivity, one will typically desire to employ relatively stringent conditions to form the hybrids. For example, relatively low salt and/or high temperature conditions, such as provided by 0.02 M–0.15M NaCl at temperatures of about 50° C. to about 70° C. Such selective conditions may tolerate little, if any, mismatch between the probe and the template or target strand.

Other alleles or other indicia of restenosis can be detected or monitored in a subject in conjunction with detection of the alleles described above. For example, echocardiography may be performed during exercise, since studies have found an association between the occurrence of clinical restenosis and both a positive post-percutaneous transluminal coronary angioplasty exercise echo as well as high values of the pre-surgical wall-motion score index and duration of wall-motion abnormalities (Peters et al. (1997) Circulation 95: 2254–61; Dagianti et al. (1997) Circulation 95: 1176–84; Gentile (1994) Cardiologia 39: 651–6). Furthermore, angioscopic studies have shown that the color (yellow versus white) of a patient's arterial plaque is highly predictive of the occurrence of restenosis following balloon angioplasty individuals with stable angina (Itoh et al. (1995) Circulation 91: 1389–96). In addition, certain polymorphisms in the gene encoding angiotensin converting enzyme have been associated with the occurrence of restenosis after coronary angioplasty in unstable angina pectoris (See e.g. Kasi et al., (1996) Am J Cardiol 77: 875–77).

In addition, behavioral studies have shown an association between hostility and other aspects of a type A behavior pattern and an increased risk for restenosis following percutaneous transluminal coronary angioplasty (Goodman et al. (1996) Mayo Clin Proc 71: 729–34). Still other studies have demonstrated an association between various serum proteins and an increased likelihood of restenosis. For example a drop in the level of antibodies against heat shock protein-65 after percutaneous transluminal coronary angioplasty is associated with a decreased risk of developing restenosis relative to individuals in which no decrease in the level of these antibodies occurred (Mukhedjee et al. (1996) Throm Haemost 75: 258–60). Another study has demonstrated an association between an elevation of serum amyloid A and the occurrence of restenosis following angioplasty (Blum et al. (1998) Clin Cardiol 21: 655–58). Relatively high levels of plasminogen activator inhibitor type-1 and relatively low levels of plasmin-plasmin inhibitor complex are also associated with restenosis (Ishiwata et al. (1997) Am Heart J 133: 387–92), as are high levels of serum lipoprotein A (Hearn et al. (1992) Am J Cardiol 69: 736–39) and elevated levels of monounsaturated fatty acids (Foley et al. (1992) Cathet Cardiovasc Diagn 25: 25–30).

4.2.2 Detection of Alleles

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A.-C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46–59 (1993)).

For mutations that produce premature termination of protein translation, the protein truncation test (PTT) offers an efficient diagnostic approach (Roest, et. al., (1993) Hum. Mol. Genet. 2:1719–21; van der Luijt, et. al., (1994) Genomics 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Any cell type or tissue may be utilized to obtain nucleic acid samples for use in the diagnostics described herein. In a preferred embodiment, the DNA sample is obtained from a bodily fluid, e.g, blood, obtained by known techniques (e.g. venipuncture) or saliva. Alternatively, nucleic acid tests can be performed on dry samples (e.g. hair or skin). When using RNA or protein, the cells or tissues that may be utilized must express an IL-1 gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of an IL-1 proinflammatory haplotype and having about 5, 10, 20, 25, or 30 nucleotides around the mutation or polymorphic region. In a preferred embodiment of the invention, several probes capable of hybridizing specifically to other allelic variants involved in a restenosis are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), and Q- Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of an IL-1 proinflammatory haplotype under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, the allele of an IL-1 proinflammatory haplotype is identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed by Maxim and Gilbert ((1977) Proc. Natl Acad Sci USA 74:560) or Sanger (Sanger et al (1977) Proc. Nat. Acad. Sci USA 74:5463). It is also contemplated that any of a variety of automated sequencing procedures may be utilized when performing the subject assays (see, for example Biotechniques (1995) 19:448), including sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labeled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl Acad Sci USA 85:4397; and Saleeba et al (1992) Methods Enzymol. 217:286295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on an allele of an IL-1 locus haplotype is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify an IL-1 locus allele. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125–144; and Hayashi (1992) Genet Anal Tech Appl 9:73–79). Single-stranded DNA fragments of sample and control IL-1 locus alleles are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of alleles in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) *Nature* 324:163); Saiki et al (1989) Proc. Natl Acad. Sci USA 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al. ((1988) Science 241:1077–1080). The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923–27). In this method, PCR is used to achieve the exponential amplification of target DNA, which is then detected using OLA.

Several techniques based on this OLA method have been developed and can be used to detect alleles of an IL-1 locus haplotype. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Another embodiment of the invention is directed to kits for detecting a predisposition for developing a restenosis. This kit may contain one or more oligonucleotides, including 5' and 3' oligonucleotides that hybridize 5'and 3' to at least one allele of an IL-1 locus haplotype. PCR amplification oligonucleotides should hybridize between 25 and 2500 base pairs apart, preferably between about 100 and about 500 bases apart, in order to produce a PCR product of convenient size for subsequent analysis.

Particularly preferred primers for use in the diagnostic method of the invention include the following:

```
5'ATG GTT TTA GAA ATC ATC AAG CCT AGG GCA 3'(SEQ ID No. 1)and

5'AAT GAA AGG AGG GGA GGA TGA CAG AAA TGT 3'(SEQ ID No. 2)

5'TGG CAT TGA TCT GGT TCA TC-3'(SEQ ID No. 3) and

5'GTT TAG GAA TCT TCC CAC TT-3'(SEQ ID No. 4);

5'CTC AGG TGT CCT CGA AGA AAT CAA A 3'(SEQ ID No. 5) and

5'GCT TTT TTG CTG TGA GTC CCG 3'(SEQ ID No. 6);

5'-CTC.AGC.AAC.ACT.CCT.AT-3'(SEQ ID NO. 7) and

5'-TCC.TGG.TCT.GCA.GCT.AA-3'(SEQ ID NQ. 8);

5'-CTA TCT GAG GAA CAA ACT AGT AGC-3'(SEQ ID NO. 9) and

5'-TAG GAC ATT GCA CCT AGG GTT TGT -3'(SEQ ID NO. 10);

5'ATT TTT TTA TAA ATC ATC AAG CCT AGG GCA 3'(SEQ. ID No. 11) and

5'AAT TAA AGG AGG GAA GAA TGA CAG AAA TGT 3'(SEQ. ID No. 12)

5'-AAG CTT GTT CTA CCA CCT GAA CTA GGC.-3'(SEQ D NO. 13) and

5'-TTA CAT ATG AGC CTT CCA TG.-3'(SEQ ID NO. 14);
```

The design of additional oligonucleotides for use in the amplification and detection of IL-1 polymorphic alleles by the method of the invention is facilitated by the availability of both updated sequence information from human chromosome 2q13—which contains the human IL-1 locus, and updated human polymorphism information available for this locus. For example, the DNA sequence for the IL-1A, IL-1B and IL-1RN is shown in FIGS. 1 (GenBank Accession No. X03833), 2 (GenBank Accession No. X04500) and 3 (GenBank Accession No. X64532) respectively. Suitable primers for the detection of a human polymorphism in these genes can be readily designed using this sequence information and standard techniques known in the art for the design and optimization of primers sequences. Optimal design of such primer sequences can be achieved, for example, by the use of commercially available primer selection programs such as Primer 2.1, Primer 3 or GeneFisher (See also, Nicklin M. H. J., Weith A. Duff G. W., "A Physical Map of the Region Encompassing the Human Interleukin-1α, interleukin-1β, and Interleukin-1Receptor Antagonist Genes" Genomics 19: 382 (1995); Nothwang H. G., et al. "Molecular Cloning of the Interleukin-1 gene Cluster: Construction of an Integrated YAC/PAC Contig and a partial transcriptional Map in the Region of Chromosome 2q13" Genomics 41:370 (1997); Clark, et al. (1986) Nucl. Acids. Res., 14:7897–7914 [published erratum appears in Nucleic Acids Res., 15:868 (1987) and the Genome Database (GDB) project at the URL http://www.gdb.org).

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moieties, metal binding moieties, antigen or antibody moieties, and the like.

The kit may, optionally, also include DNA sampling means. DNA sampling means are well known to one of skill in the art and can include, but not be limited to substrates, such as filter papers, the AmpliCard™ (University of Sheffield, Sheffield, England S10 2JF; Tarlow, J W, et al., *J. of Invest. Dematol.* 103:387–389 (1994)) and the like; DNA purification reagents such as Nucleon™ kits, lysis buffers, proteinase solutions and the like; PCR reagents, such as 10×reaction buffers, thermostable polymerase, dNTPs, and the like; and allele detection means such as the HinfI restriction enzyme, allele specific oligonucleotides, degenerate oligonucleotide primers for nested PCR from dried blood.

4.2.3. Pharmacogenomics

Knowledge of the particular alleles associated with restenosis, alone or in conjunction with information on other genetic defects contributing to restenosis, such as the PL(A1/A2) polymorphism in a platelet glycoprotein (See Abbate et al. (1998) Am J Cardiol 82: 524–5), allows a customization of the restenosis therapy to the individual's genetic profile, the goal of "pharmacogenomics". For example, subjects having an allele 2 of any of the following markers: IL-1A (+4845), IL-1B (−511), IL-1B (+3954) or IL-1RN (VNTR) or any nucleic acid sequence in linkage disequilibrium with any of these alleles may have or be predisposed to developing restenosis and may respond better to particular therapeutics that address the particular molecular basis of the disease in the subject. Thus, comparison of an individual's IL-1 profile to the population profile for restenosis, permits the selection or design of drugs or other therapeutic regimens that are expected to be safe and efficacious for a particular patient or patient ail population (i.e., a group of patients having the same genetic alteration).

In addition, the ability to target populations expected to show the highest clinical benefit, based on genetic profile can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since measuring the effect of various doses of an agent on a restenosis causative mutation is useful for optimizing effective dose).

The treatment of an individual with a particular therapeutic can be monitored by determining protein (e.g. IL-1α, IL-1β, or IL-1Ra), mRNA and/or transcriptional level. Depending on the level detected, the therapeutic regimen can then be maintained or adjusted (increased or decreased in dose). In a preferred embodiment, the effectiveness of treating a subject with an agent comprises the steps of: (i) obtaining a preadministration sample from a subject prior to administration of the agent; (ii) detecting the level or amount of a protein, mRNA or genomic DNA in the preadministration sample; (iii) obtaining one or more post-administration samples from the subject; (iv) detecting the level of expression or activity of the protein, mRNA or genomic DNA in the post-administration sample; (v) comparing the level of expression or activity of the protein, mRNA or genomic DNA in the preadministration sample with the corresponding protein, mRNA or genomic DNA in the postadministration sample, respectively; and (vi) altering the administration of the agent to the subject accordingly.

Cells of a subject may also be obtained before and after administration of a therapeutic to detect the level of expression of genes other than an IL-1 gene to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

4.3 Restenosis Therapeutics

Modulators of IL-1 (e.g. IL-1α, IL-1β or IL-1 receptor antagonist) or a protein encoded by a gene that is in linkage disequilibrium with an IL-1 gene can comprise any type of compound, including a protein, peptide, peptidomimetic, small molecule, or nucleic acid.

Preferred agonists include nucleic acids (e.g. encoding an IL-1 protein or a gene that is up- or down-regulated by an IL-1 protein), proteins (e.g. IL-1 proteins or a protein that is up- or down-regulated thereby) or a small molecule (e.g. that regulates expression or binding of an IL-1 protein). Preferred antagonists, which can be identified, for example, using the assays described herein, include nucleic acids (e.g. single (antisense) or double stranded (triplex) DNA or PNA and ribozymes), protein (e.g. antibodies) and small molecules that act to suppress or inhibit IL-1 transcription and/or protein activity.

70 4.3.1. Effective Dose

Toxicity and therapeutic efficacy of such compounds can be determined by standard pharmaceutical procedures in cell cultures or experimental animals, e.g., for determining The $LD_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.3.2. Formulation and Use

Compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.4 Assays to Identify Restenosis Therapeutics

Based on the identification of mutations that cause or contribute to the development of restenosis, the invention further features cell-based or cell free assays, e.g., for identifying restenosis therapeutics. In one embodiment, a cell expressing an IL-1 receptor, or a receptor for a protein that is encoded by a gene which is in linkage disequilibrium with an IL-1 gene, on the outer surface of its cellular membrane is incubated in the presence of a test compound alone or in the presence of a test compound and another protein and the interaction between the test compound and the receptor or between the protein (preferably a tagged protein) and the receptor is detected, e.g., by using a microphysiometer (McConnell et al. (1992) *Science* 257:1906). An interaction between the receptor and either the test compound or the protein is detected by the microphysiometer as a change in the acidification of the medium. This assay system thus provides a means of identifying molecular antagonists which, for example, function by interfering with protein- receptor interactions, as well as molecular agonist which, for example, function by activating a receptor.

Cellular or cell-free assays can also be used to identify compounds which modulate expression of an IL-1 gene or a gene in linkage disequilibrium therewith, modulate translation of an mRNA, or which modulate the stability of an mRNA or protein. Accordingly, in one embodiment, a cell which is capable of producing an IL-1, or other protein is incubated with a test compound and the amount of protein produced in the cell medium is measured and compared to that produced from a cell which has not been contacted with the test compound. The specificity of the compound vis a vis the protein can be confirmed by various control analysis, e.g., measuring the expression of one or more control genes. In particular, this assay can be used to determine the efficacy of antisense, ribozyme and triplex compounds.

Cell-free assays can also be used to identify compounds which are capable of interacting with a protein, to thereby modify the activity of the protein. Such a compound can, e.g., modify the structure of a protein thereby effecting its ability to bind to a receptor. In a preferred embodiment, cell-free assays for identifying such compounds consist essentially in a reaction mixture containing a protein and a test compound or a library of test compounds in the presence or absence of a binding partner. A test compound can be, e.g., a derivative of a binding partner, e.g., a biologically inactive target peptide, or a small molecule.

Accordingly, one exemplary screening assay of the present invention includes the steps of contacting a protein or functional fragment thereof with a test compound or library of test compounds and detecting the formation of complexes. For detection purposes, the molecule can be labeled with a specific marker and the test compound or library of test compounds labeled with a different marker. Interaction of a test compound with a protein or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the protein or functional fragment thereof is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an IL-1 or other protein, (ii) an appropriate receptor, and (iii) a test compound; and (b) detecting interaction of the protein and receptor. A statistically significant change (potentiation or inhibition) in the interaction of the protein and receptor in the presence of the test compound, relative to the interaction in the absence of the test compound, indicates a potential antagonist (inhibitor). The compounds of this assay can be contacted simultaneously. Alternatively, a protein can first be contacted with a test compound for an appropriate amount of time, following which the receptor is added to the reaction mixture. The efficacy of the compound can be assessed by generating dose response curves from data obtained using various concentrations of the test compound. Moreover, a control assay can also be performed to provide a baseline for comparison.

Complex formation between a protein and receptor may be detected by a variety of techniques. Modulation of the formation of complexes can be quantitated using, for example, detectably labeled proteins such as radiolabeled, fluorescently labeled, or enzymatically labeled proteins or receptors, by immunoassay, or by chromatographic detection.

Typically, it will be desirable to immobilize either the protein or the receptor to facilitate separation of complexes from uncomplexed forms of one or both of the proteins, as well as to accommodate automation of the assay. Binding of protein and receptor can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the receptor, e.g. an $^{35}$S-lebeled receptor, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of protein or receptor found in the bead fraction quantitated from the gel using standard electrophoretic techniques such as described in the appended examples. Other techniques for immobilizing proteins on matrices are also available for use in the subject assay. For instance, either protein or receptor can be immobilized utilizing conjugation of biotin and streptavidin. Transgenic animals can also be made to identify agonists and antagonists or to confirm the safety and efficacy of a candidate therapeutic. Transgenic animals of the invention can include non-human animals containing a restenosis causative mutation under the control of an appropriate endogenous promoter or under the control of a heterologous promoter.

The transgenic animals can also be animals containing a transgene, such as reporter gene, under the control of an appropriate promoter or fragment thereof. These animals are useful, e.g., for identifying drugs that modulate production of an IL-1 protein, such as by modulating gene expression. Methods for obtaining transgenic non-human animals are well known in the art. In preferred embodiments, the expression of the restenosis causative mutation is restricted to specific subsets of cells, tissues or developmental stages utilizing, for example, cis-acting sequences that control expression in the desired pattern. In the present invention, such mosaic expression of a protein can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of a mutation can be regulated via site-specific genetic manipulation in vivo, are known to those skilled in the art.

The transgenic animals of the present invention all include within a plurality of their cells a restenosis causative mutation transgene of the present invention, which transgene alters the phenotype of the "host cell". In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the causative mutation transgene can be regulated via control of recombinase expression.

Use of the cre/loxP recombinase system to regulate expression of a causative mutation transgene requires the construction of a transgenic animal containing transgenes encoding both the Cre recombinase and the subject protein. Animals containing both the Cre recombinase and the restenosis causative mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "trarsgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or H-2q haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J*. 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

The present invention is further illustrated by the following examples which should not be construed as limiting in any way. The contents of all cited references (including literature references, issued patents, published patent applications as cited throughout this application) are hereby expressly incorporated by reference. The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984); U.S. Pat. No. 4,683,195; U.S. Pat. No. 4,683,202; and Nucleic Acid Hybridization (B. D. Hames & S. J. Higgins eds., 1984).

5. EXAMPLES

5.1. IL-1RN*2 Allele Association With Decreased Risk of Restenosis

In this example, DNA samples collected form 171 patients attending for elective percutaneous transluminal coronary angioplasty were studied at 4 and 6 months postsurgery using angiography. At follow-up angiography, the patients were separated into restenosers (>50% luminal narrowing) and non-restenosers (<50% luminal narrowing), and were further assessed for their genotype at the following IL-1 polymorphisms: IL-1A (−889), IL-1B (−511), IL-1B (+3954), IL-1RN (intron 2 VNTR).

Methods

Patients 171 patients who were scheduled to undergo follow-up angiography after elective PTCA without stenting as part of other protocols were studied. Quantitive coronary angiography was performed on-line (Philips Integris HM 3000, (S); Siemens Micor (L)). Patients were electively recruited in Sheffield where follow-up angiography was performed at 6 months. 117 patients were recruited from Leicester. These patients had been part of the SHARP study (Subcutaneous Heparin and Angioplasty Restenosis Prevention) where follow-up had been performed at 4 months±2 weeks (Samani N. J., et al., *Lancet*. 1995;345:1013–1016), and 67% of the original cohort were electively recalled for the current study. The SHARP study did not show any effect of subcutaneous heparin upon rates of restenosis.

A dichotomous definition of restenosis was used setting restenosis as a luminal narrowing >50% and non-restenosis <50%, at follow-up angiography. Using this definition, the cohort comprised 39% restenosers and 61% non-restenosers.

These studies were approved by the North Sheffield Ethics Committee and by the Leicester Ethics Committee, and patients gavie their written informed consent.

Analysis of Genetic Polymorphisms

Genomic DNA was extracted from whole blood using standard methods and PCR for variants within the IL-1 locus performed as previously described (Francis S E, et al. *Circulation* 1999;99:861–866) or using an automated Taqman™ FRET-based system. The less common IL-1RN gene variant is referred to as IL-1R*2.

Differences in genotype distribution were assessed by chi-square analysis of the relevant 2*2 contingency table (table 2). Odds ratios with 95% confidence intervals were also calculated. To summarize results over the Leicester and Sheffield cohorts Mantel Haenszel analyses were performed. A p-value of less than 0.05 was used to indicate nominal significance. For an overall type 1 error of 0.05, a corrected critical p-value of 0.013 should be used to account for multiple testing. Here we have corrected accounting for the 4 loci tested. However, due to linkage disequilibrium between these loci, this correction is likely to be conservative. IL-1RN (VNTR) was collapsed and analysed as a biallelic marker since very few genotypes were recorded with the rarer alleles. Neither of the cohorts studied were significantly different from the Hardy Weinberg Equilibrium for any of the polymorphisms.

Demographic data were expressed as percent with actual counts in parentheses. These variables were compared by $\chi^2$ test.

Results

Demographics

The Sheffield and Leicester combined cohorts were well matched for baseline clinical features (Table 1).

Genetic analysis

The Mantel-Haenzel results summarized over the Leicester and Sheffield cohorts showed no significant differences in genotypic distributions at the IL-1A (−889), IL-1B (+3954) and IL-1B (−511) loci between restenosers and non-restenosers (Table II).

The frequency of allele 2 (IL-1RN*2) was however increased in the non-restenosers: 34% versus 23% in restenosers (FIG. 1, Table II). Genotype distribution analysis indicated a significant association between homozygosity for allele*2 and non-restenosis (MH, p=0.0196 (L+S); p=0.0131 (L+S, SVD only, Table II)). When the populations are analysed separately, the data trends concur, but are only significant in the Sheffield SVD cohort (p=0.0384 (S); p=0.1573 (L)). This is most likely because of the low statistical power of these tests, since sample sizes are small due to data subdivision.

Interestingly, and a further implication that the results are more specifically applicable to SVD only, when carriage of IL-1RN*2 is compared between SVD and MVD groups in the Leicester cohort, there is a significant increase of carriage of IL-RN*2 in the SVD group (p=0.0342). This result is strengthened when the Sheffield SVD patients are added (p=0.0314).

Discussion

These data suggest a genetic susceptibility to restenosis mediated by polymorphism at the IL-1 locus.

Specifically, the data presented here indicate that IL-1RN*2 is associated with a lower restenosis rate in patients with SVD. This supports previous data indicating that distinct populations with different prepensitites to restenosis exist, and that the precess is at least to some extent patient-related rather than lesion dependent or both (Lehmann K G, et al. *Circulation*, 1996;93: 1123–1132; Weintraub W S, et al. *Am J Cardiol*. 1993;72: 1107–1113). Our previous data (Francis S E, et al. *Circulation* 1999;99:861–866)., that IL-1RN*2 is associated with SVD on the basis of angiography, led us to speculate that there may be a true genetic distinction between SVD and MVD. If so, this might indicate that IL-1RN*2 genotype could either lead more rapidly to SVD or protest against progression to MVD. The data presented here add to this.

Since restenosis is a biological phenomenon characterized by an early to inflammatory response, these new data suggest that IL-1RN*2 may modulate the arterial wall response to injury in such a way as to reduce the likelihood of restenosis. Whilst there are many potential mechanisms by which this could occur, a protection or beneficial effect of IL-1RN*2 upon vessel wall healing in response to injury is suggested. This might also support the hypothesis that IL-1RN*2 slows progression toward MVD made in our earlier study (Francis SE, et al. *Circulation* 1999;99:861–866).

The mechanism by which IL-1RN*2 modulates the vessel wall response to injury is unclear. This polymorphism has functional correlates but these appear highly cell-type specific. In monocytes, IL-1RN*2 is associated with increased IL-1ra production under basal and stimulated conditions (Wilkinson R J, et al. *J Exp Med.* 1999;189:1863–1873). In contrast, within cells of the columnar epithelium in inflammatory bowel disease (Carter M J, *Gastroenterology.* 1998;114(4):3882), and in endothelial cells (Dewberry R M, et al. *Heart.* 1999;81(Suppl 1); 78 [abstract]), IL-1RN*2 os associated with reduced production of IL-1ra Since the inflammatory influx seen following experimental PTCA in pigs is highly neutrophilic and IL-1B staining abundant, predominantly in the luminal endothelium even into the late phase of healing (Chamberlin J, et al. *Cardiovasc Res.* 1999;44(1):156–165), we speculate that the relatively pro-inflammatory endothelial cell phenotype created by the IL-1RN*2 genotype may be important to PTCA. This suggests that modifying the inflammatory response at the time of injury may indeed be beneficial acting to limit the healing response that leads to luminal re-narrowing.

The IL-1RN VNTR polymorphism is known to be in linkage disequilibrium with other genes in the IL-1 locus (Cox A, et al. *Am J Hum Genet.* 1998;62(5):1180–1188), and although there are some weakly consistent trends which exist for IL-1A (=4845) and IL-1B (+3954), there are no other significant associations with restenosis or non-restenosis for the other IL-1 polymorphisms within the cluster. Hence, a specific complex haplotype is not supported by these data. However, linkage disequilibrium between this polymorphism and other unidentified gene polymorphisms cannot be excluded.

Due to sub-division of the data, this study has small sample sizes for many of the analyses performed. This reduces power and to some extent the reliability and confidence in these findings. However, the results here are strengthened by the fact that two separate cohorts were collected, and that very similar directional trends were found in both populations. It was consistently found that evidence for association was strengthened by summarizing over the two cohorts, which further illustrates the concordance. It is, of course, possible that spurious results could have arisen due to genetic admixture within the cohorts, but again the consistence between the two populations argues away from this.

We favor the interpretation that polymorphic variation within the IL-1 locus has an important impact on arterial disease. Our original published work (Francis S E, et al. *Circulation* 1999;99:861–866) showed an association with single vessel coronary disease in two independent populations (Sheffield and London). The study reported here shows association with a different clinical phenotype in a population predominantly from Leicester. Other investigators have demonstrated association between IL-1RN+2016, a single nucleotide polymorphism (SNP) in linkage disequilibrium with IL-1RN*2, and carotid intimal/medial changes in African Americans (Pankow J S, et al. Association of Interleukin-1 gene variants and carotid arterial wall thickness: the ARID Study. 71*st EAS Congress and Satellite Symposia*) These all argue strongly that polymorphism within the IL-1 locus does have an impact on the pathogenesis of atherosclerotic lesions, although the mechanism remains to be elucidated.

The biological control of IL-1 is complex (Dinarello C A. *Blood.* 1991;77:1627–1632). IL-1 actions are inhibited by a non-signaling receptor IL-1RII in membrane bound or soluble form and also by IL-1ra (Symons J A, et al. *J Exp Med.* 1991;177:557–560) which binds without agonist activity to be signaling receptor IL-1RI (Symons J A, et al. *Proc Natl. Acad Sci.* 1995;92:1714–1718). IL-1ra is an acute phase protein and induced by cytokines and bacterial products (Arend W P. *Adv Immunol.* 1993;54:167–227). Levels of IL-1 and IL-1ra in vivo vary in parallel suggesting a coordinated pattern of regulation (Arend W P. *Adv Immunol.* 1993;54:167–227). IL-1ra is detected in the endothelium of diseased coronary arteries (Dewberry R M, et al. *Heart.* 1999;81(Suppl 1); 78 [abstract]) and inhibits fatty streak formation in the apolipoprotein E deficient mouse (Hirsch E, et al. *Proc Natl Acad Sci.* 1996;93:11008–11013). These data taken together strongly implicate IL-1ra in the control of inflammation in the arterial wall.

In conclusion, the results reported here suggest an important association between IL-1RN*2 and protection from restenosis in individuals with SVD. They also might suggest that inflammation may be a positive influence rather than wholly negative after arterial injury. Validation studies in larger study groups including a post-stenting and a reappraisal of the complex injury-repair mechanisms employed by the arterial wall are indicated.

TABLE 1

Clinical Characteristics of Patients with and without Restenosis

|  | Restenosis | Non-restenosis | P |
|---|---|---|---|
| Leicester |  |  |  |
| no. of patients | 49 | 69 |  |
| age (yrs) mean ± SEM | 59.08 ± 1.19 | 57.08 ± 0.91 | ns |
| Women (%) | 12.2 [6] | 17.4 [12] | nd |
| Hypertension (%) | 24 [12] | 17.3 [12] | nd |
| Smoking (%) | 29 [14] | 34.7 [24] | nd |
| Diabetes (%) | 2.04 [1] | 4.34 [3] | nd |
| MI (%) | 48.9 [24] | 43.4 [30] | nd |
| Multivessel disease (%) | 48.9 [24] | 39.1 [27] | nd |
| Sheffield |  |  |  |
| no. of patients | 18 | 35 |  |
| age (yrs) mean ± SEM | 53.61 ± 1.77 | 53.88 ± 1.45 | ns |
| Women (%) | 17 [3] | 11.4 [4] | nd |
| Hypertension (%) | 61.1 [11] | 37.1 [13] | nd |
| Smoking (%) | 77.7 [14] | 74.2 [26] | nd |
| Diabetes (%) | 5.5 [1] | 11.4 [4] | nd |
| MI (%) | 57.1 [8] | 42.8 [15] | nd |
| Multivessel disease (%) | 0 | 0 | nd |
| Sheffield and Leicester |  |  |  |
| no. of patients | 67 | 104 |  |
| age (yrs) mean ± SEM | 57.97 ± 1.44 | 55.98 ± 0.98 | ns |
| Women (%) | 13.4 [9] | 15.3 [16] | ns |
| Hypertension (%) | 34.3 [23] | 24.0 [25] | ns |
| Smoking (%) | 41.7 [28] | 48.0 [50] | ns |
| Diabetes (%) | 2.98 [2] | 6.7 [7] | ns |
| MI (%) | 47.7 [32] | 43.2 [45] | ns |
| Multivessel disease (%) | 35.8 [24] | 25.9 [27] | ns |

Values in parentheses are the number of patients affected in that cohort.
Hypertension defined as diastolic bp > 95 mmHg (Leicester); Sytolic bp > 160 mmHg.
Smoking: current or former (Sheffield), current (Leicester).
ns - not significant, where normal statistical significance, P < 0.05.nd-not done.

TABLE II

Carriage of alleles within the IL-1 locus in Sheffield and Leicester restenosis and non-restenosis cohorts.

|  | 11 | 12/22 | 11 | 12/22 | 11/12 | 22 | 11/12 | 22 |
|---|---|---|---|---|---|---|---|---|
| Leicester SVD & MVD | | | | | | | | |
| restenosis | 20 | 24 | 26 | 19 | 36 | 7 | 46 | 3 |
| non | 34 | 27 | 42 | 19 | 47 | 12 | 58 | 10 |
| p-value | 0.2399 | | 0.2982 | | 0.6194 | | 0.6191 | |
| OR | 1.6 | | 1.5 | | 1.3 | | 2.6 | |
| 95% CI | 0.7, 3.6 | | 0.7, 3.3 | | 0.5, 3.7 | | 0.7, 10.2 | |
| Sheffield SVD only | | | | | | | | |
| restenosis | 8 | 10 | 10 | 8 | 15 | 3 | 16 | 0 |
| non | 20 | 14 | 22 | 11 | 29 | 4 | 25 | 7 |
| p-value | 0.4329 | | 0.3244 | | 0.6691 | | 0.0384 | |
| OR | 1.6 | | 1.8 | | 0.7 | | N/A | |
| 95% CI | 0.5, 5.2 | | 0.6, 5.7 | | 0.1, 3.5 | | N/A | |
| MH | | | | | | | | |
| p-value | 0.1604 | | 0.1594 | | 0.8333 | | 0.0196 | |

MH Mantel-Haenzsel summary statistic
N/A OR and p-value not applicable since one of the values in the contingency table is 0.
Note: Alleles are grouped according to previously described commonest haplotype (Cox A, et al. Am J Hum Genet. 1998;62(5):1180–1188), carriage of *2 for IL-1A [+4845]; IL1B [+3954] and carriage of *1 for IL-1B [−511] and IL-1Rn [VNTR].

TABLE III

Homozygosity at IL-1RN*2 illustrates the difference between SVD and MVD in the Sheffield and Leicester cohorts.

|  | SVD | | MVD | |
|---|---|---|---|---|
|  | 11/12 | 22 | 11/12 | 22 |
| Leicester | | | | |
| restenosis | 24 | 1 | 22 | 2 |
| non | 35 | 7 | 23 | 3 |
| p-value | 0.1573 | | 0.7699 | |
| OR | 4.8 | | 1.4 | |
| 95% CI | 0.6, 41.6 | | 0.1, 4.6 | |
| Sheffield | | | | |
| restenosis | 16 | 0 | N/A | |
| non | 25 | 7 | | |
| p-value | 0.0384 | | | |
| OR | N/A | | | |
| 95% CI | | | | |
| MH | | | | |
| p-value | 0.0131 | | | |

MH Mantel Naenszel summary statistic
N/A OR and p-value not applicable since one of the values in the contingency table is 0.

5.2. Protective Role Against Retenosis From an Interleukin-1 Receptor Antagonist Gene Polymorphism in Patients Treated With Coronary Stenting (The Munich Study)

Patients

The study included 1850 consecutive Caucasian patients with symptomatic coronary artery disease who underwent coronary stent implantation at Deutsches Herzzentrum Munchen and 1. Medizinische Klinik rechts der Isar der Technischen Universität München. All patients were scheduled for angiographic follow-up at 6 months. All patients participating in this study gave written informed consent for the intervention, follow-up angiography, and genotype determination.

The study protocol conformed to the Declaration of Helsinki and was approved by the institutional ethics committee.

TABLE 3

Baseline clinical characteristics.

|  | IL-1RN 1/2 or 2/2 (n = 896) | IL-1RN 1/1 (n = 954) | P |
|---|---|---|---|
| Age-yr | 63.4 ± 10.0 | 62.6 ± 10.0 | 0.11 |
| Women-% | 22.4 | 19.9 | 0.19 |
| Arterial hypertension-% | 67.2 | 68.9 | 0.44 |
| Diabetes-% | 22.7 | 19.4 | 0.08 |
| Current or former smoker-% | 38.7 | 41.2 | 0.28 |
| Elevated total cholesterol-% | 42.5 | 43.1 | 0.81 |
| Acute myocardial infarction-% | 20.3 | 20.2 | 0.97 |
| Unstable angina-% | 27.9 | 27.8 | 0.95 |
| Prior bypass surgery-% | 10.6 | 11.5 | 0.53 |
| Reduced left ventricular function-% | 31.3 | 27.7 | 0.09 |
| Number of diseased coronary vessels | | | 0.39 |
| -1 vessel-% | 29.2 | 27.3 | |
| -2 vessels-% | 32.9 | 31.9 | |
| -3 vessels-% | 37.8 | 40.9 | |
| Periprocedural abciximab therapy-% | 19.8 | 19.6 | 0.93 |

Data are proportions or mean SD

The protocol of stent placement and poststenting therapy is familiar to practitioners in the arts. Most of the stents were implanted hand-mounted on conventional angioplasty balloons. Postprocedural therapy consisted of aspirin (100 mg twice daily, indefinitely) and ticlopidine (250 mg twice daily for 4 weeks). Patients with suboptimal results due to residual thrombus or dissection with flow impairment after stent implantation received additional therapy with abciximab given as bolus injection during stent insertion procedure and as a 12-hours continuous infusion thereafter. The decision to give abciximab was taken at the operator's discretion.

Determination of the IL-1RN Genotype

Genomic DNA was extracted from 200 ml of peripheral blood leukocytes with the QIAamp Blood Kit (Qiagen, Hilden, Germany) and the High Pure PCR Template Preparation Kit (Boehringer Mannheim, Mannheim, Germany). IL-1RN genotyping was performed with the ABI Prism Sequence Detection System (PE Applied Biosystems, Weiterstadt, Germany). The use of allele-specific fluorogenic probes in the 5' nuclease reaction combines DNA amplification and genotype determination into a single assay 33. IL-1RN (+2018), a single base pair polymorphism in exon 2, was the polymorphism typed for this study 26. The nucleotide sequences of primers and probes were as follows: forward primer 5' GGG ATG TTA ACC AGA AGA CCT TCT ATC T 3' (SEQ ID NO.22), reverse primer 5° CAA CCA CTC ACC TTC TAA ATT GAC ATT 3' (SEQ ID NO. 23), allele 1 probe 5' AAC AAC CAA CTA GTT GCT GGA TAC TTG CAA 3' (SEQ ID NO. 24), allele 2 probe 5' ACA ACC AAC TAG TTG CCG GAT ACT TGC 3' (SEQ ID NO. 25). The probes for allele 1 were labeled with the fluorescent dye 6-carboxy-fluorescein (FAM) and for allele 2 with the fluorescent dye tetrachloro-6-carboxy-fluorescein (TET) at the 5' end. Both probes were labeled with the quencher 6-carboxy-tetramethyl-rhodamine (TAMRA) at their 3' ends. The thermocycling protocol consisted of 40 cycles of denaturation at 95 C for 15 seconds and annealing/extension at 64 C for 1 minute. Genotype validation was performed by repeating the determination in 20% of the patients using a duplicate DNA sample with a novel subject code unrelated to the original subject code. There was a 100% matching between the 2 results.

Angiographic Assessment

Coronary lesions were classified according to the modified American College of Cardiology/American Heart Association grading system. Left ventricular function was assessed qualitatively on the basis of biplane angiograms using a 7 segment division; the diagnosis of reduced left ventricular function was established in the presence of at least two hypokinetic segments in the contrast angiogram. Quantitative computer-assisted angiographic analysis was performed off-line on angiograms obtained just before stenting, immediately after stenting, and at follow up using the automated edge-detection system CMS (Medis Medical Imaging Systems, Nuenen, The Netherlands). Operators were unaware of the patient's IL-1RN genotype. Identical projections of the target lesion were used for all assessed angiograms. Minimal lumen diameter, interpolated reference diameter, diameter stenosis, lesion length and diameter of the maximally inflated balloon were the angiographic parameters obtained with this analysis system. Acute lumen gain was calculated as the difference between minimal lumen diameter at the end of intervention and minimal lumen diameter before the intervention. Late lumen loss was calculated as the difference between minimal lumen diameter at the end of intervention and minimal lumen diameter at the time of follow-up angiography. Loss index was calculated as the ratio between late lumen loss and acute lumen gain.

Definitions and Study Endpoints

Primary endpoint of the study was restenosis. Two measures of restenosis were assessed: the incidence of angiographic restenosis defined as a diameter stenosis of 50% at 6month follow-up angiography, and the need for target vessel revascularization (PTCA or aortocoronary bypass surgery [CABG]) due to symptoms or signs of ischemia in the presence of angiographic restenosis at the stented site over 1 year after the intervention. Other major adverse events evaluated were: death from any cause and myocardial infarction. All deaths were considered due to cardiac causes unless an autopsy established a noncardiac cause. The diagnosis of acute myocardial infarction was based on the criteria applied in the EPISTENT trial (new pathological Q waves or a value of creatine kinase [CK] or its MB isoenzyme at least 3 times the upper limit) 35. CK was determined systematically over the 48 hours following stenting procedure. Clinical events were monitored throughout the 1-year follow-up period. The assessment was made on the basis of the information provided by hospital readmission records, referring physician or phone interview with the patient. For all those patients who revealed cardiac symptoms during the interview, at least one clinical and electrocardiographic check-up was performed at the outpatient clinic or by the referring physician.

Statistical Analysis

Discrete variables are expressed as counts or percentages and compared with Chi-square or Fisher's exact test, as appropriate. Continuous variables are expressed as mean SD and compared by means of the unpaired, two-sided t-test or analysis of variance for more than 2 groups. Risk analysis was performed calculating the odds ratio and the 95% confidence interval. The main analysis consisted in comparing combined heterozygous and homozygous carriers of the IL-11RN*2 allele with homozygous carriers of the IL-11RN*1 allele. Moreover, the association between IL-1RN genotype and restenosis was assessed in a multivariate logistic regression model including also those clinical and lesion-related characteristics for which the comparison between carriers and noncarriers of the IL-1RN*2 allele showed a P-value 0.30. In this multivariate model, we tested for the possible interaction between IL-1RN genotype and age. Since the relative contribution of genetic factors to multifactorial processes such as restenosis may decrease with the age, we carried out an additional analysis for a prespecified subgroup of patients <60 years. Successively, we used test for trend for assessing gene dose effect, i.e. a stepwise increasing phenotypic response with the presence of 0, 1 or 2 putative alleles. Statistical significance was accepted for P-values 0.05.

Results

Patient Characteristics

The observed IL-1RN genotypes in the study population were 1/1 in 954 (51.6%), 1/2 in 742 (40.1%) and 2/2 in 154 (8.3%). Thus, allele 2 frequency was 0.28. The observed distribution complied with Hardy-Weinberg equilibrium. Main baseline characteristics of the patients are listed in Table 6 and compared between carriers and noncarriers of the IL-1RN*2 allele. There was a trend to a higher frequency of diabetes and reduced left ventricular function among carriers of the IL-1RN*2 allele. The other characteristics were evenly distributed between the 2 groups. The angiographic and procedural characteristics at the time of intervention are listed in Table 7 and show no significant differences between carriers and noncarriers of the IL-1RN*2 allele.

TABLE 5

Lesion and procedural characteristics at the time of intervention.

| | IL-1RN 1/2 or 2/2 (n = 896) | IL-1RN 1/1 (n = 954) | P |
|---|---|---|---|
| Target coronary vessels | | | 0.89 |
| Left main-% | 1.3 | 1.6 | |

TABLE 5-continued

Lesion and procedural characteristics at the time of intervention.

|  | IL-1RN 1/2 or 2/2 (n = 896) | IL-1RN 1/1 (n = 954) | P |
|---|---|---|---|
| LAD-% | 40.1 | 39.3 |  |
| LCx-% | 19.9 | 20.0 |  |
| RCA-% | 32.6 | 31.9 |  |
| Venous bypass graft-% | 6.1 | 7.2 |  |
| Complex lesions-% | 75.2 | 74.1 | 0.58 |
| Restenotic lesions-% | 25.3 | 23.3 | 0.30 |
| Before stenting |  |  |  |
| Reference diameter, mm | 3.02 ± 0.53 | 3.05 ± 0.54 | 0.29 |
| Diameter stenosis-% | 79.1 ± 14.9 | 78.7 ± 15.7 | 0.57 |
| Lesion length-mm | 12.1 ± 6.9 | 12.1 ± 6.6 | 0.98 |
| Procedural data |  |  |  |
| Measured balloon diameter-mm | 3.2 ± 0.5 | 3.2 ± 5 | 0.45 |
| Maximal balloon pressure-atm | 13.9 ± 3.3 | 13.8 ± 3.2 | 0.20 |
| Stented segment length-mm | 20.0 ± 14.3 | 20.3 ± 13.6 | 0.70 |
| Immediately after stenting |  |  |  |
| Diameter stenosis-% | 5.2 ± 9.1 | 5.4 ± 7.6 | 0.47 |

Data are proportions or mean ± SD

LAD indicates left anterior descending coronary artery; LCx, left circumflex coronary artery; RCA, right coronary artery; complex lesions were defined as ACC/AHA lesion types B2 and C, according to the American College of Cardiology/American Heart Association grading system.

IL-1RN Polymnrphism, Mortality and Myocardial Infarction After Stenting

Table 6 shows the adverse clinical events observed within the first 30 days after coronary stenting in carriers and noncarriers of the IL-1RN*2 allele. There was no association between the presence of the IL-1RN*2 allele and death, myocardial infarction or target vessel revascularization, showing no significant influence of the polymorphism in the IL-1ra gene in the risk for early thrombotic events after coronary stenting.

TABLE 6

Incidence of adverse events recorded during the early 30 days

|  | IL-1RN 1/2 or 2/2 (n = 896) | IL-1RN 1/1 (n = 954) | P |
|---|---|---|---|
| Death-% | 0.9 | 0.9 | 0.91 |
| Nonfatal myocardial infarction-% | 3.3 | 2.6 | 0.52 |
| -Q-wave-% | 1.1 | 0.7 | 0.39 |
| -non-Q-wave-% | 2.2 | 1.9 | 0.60 |
| Target vessel revascularization-% | 3.0 | 2.3 | 0.34 |

One-year follow-up indicated also that there is no correlation between the presence of the IL-1RN*2 allele and mortality or incidence of myocardial infarction after the intervention. During the 1-year period, mortality rate was 2.8% in the combined group of IL-1RN 1/2 and IL-1RN 2/2 patients and 2.2% in IL-1 1/1 patients (P=0.42), yielding an odds ratio of 1.28 (95% confidence interval, 0.71–2.29). The incidence of nonfatal myocardial infarction was 3.5% in IL-1RN*2 allele carriers and 3.9% in homozygous carriers of the IL-1RN*1 allele (P=0.54), and the respective odds ratio was 0.86 (0.53–1.4).

IL-1RN Polymorphism and Restenosis After Stenting

Control angiography was performed in 84% of the patients after a median of 188 days (interquartile range, 171–205 days). The proportion of patients with control angiography was similar in the 2 groups defined by the presence or absence of the IL-1RN*2 allele. Table 7 lists the results of the quantitative assessment of 6-month angiograms.

TABLE 7

Results at follow-up angiography.

|  | IL-1RN 1/2 or 2/2 (n = 758) | IL-1RN 1/1 (n = 798) | P |
|---|---|---|---|
| Late lumen loss-mm | 1.16 ± 0.82 | 1.24 ± 0.86 | 0.07 |
| Loss index | 0.53 ± 0.38 | 0.59 ± 0.45 | 0.009 |
| Diameter stenosis-% | 41.8 ± 26.2 | 45.2 ± 28.7 | 0.015 |
| Restenosis rate-% | 30.2 | 35.6 | 0.024 |

Data are proportions or mean ± SD

Of note, loss index which reflects the hyperplastic response after stenting was significantly lower in patients who carried the IL-1RN*2 allele. The incidence of angiographic restenosis was also significantly lower in carriers of the IL-1RN*2 allele, with 30.2% vs. 35.6% in patients of the IL-1RN 1/1 genotype. Thus, the presence of the IL-1RN*2 allele was associated with a 22% decrease in restenosis rate (odds ratio, 0.78 [0.63–0.97]; FIG. 9, left panel). Clinical restenosis expressed as the need for target vessel revascularization was also significantly lower, with 17.7% in IL-1RN*2 allele carriers vs. 22.7% in homozygous patients for the IL-1RN*1 allele (P=0.026), yielding an odds ratio of 0.73 (0.58–0.92) as shown in FIG. 9, left panel.

Age, gender, the presence or absence of diabetes, smoking habit, reduced left ventricular function and restenotic lesions, vessel size (all variables differing in univariate analysis by a P-value 0.30) were entered into the multivariate model for angiographic restenosis along with the presence or absence of the IL-1RN*2 allele. Older age (P=0.005), the presence of diabetes (P<0.001), restenotic lesion (P<0.001) and small vessel size (P<0.001) were independently correlated with an increased risk of restenosis. On the opposite, the presence of the IL-1RN*2 allele was independently (P<0.001) correlated with a decreased risk for restenosis with an adjusted odds ratio of 0.81 (0.71–0.92). In addition, there was a significant interaction between the presence of the IL-1RN*2 allele and age (P=0.009) as reflected by a progressively stronger protective effect of this allele in younger patients.

The results of the analysis in the prespecified subgroup of patients <60 years (n=696) are presented in Table 8, FIG. 9, right panel and FIG. 10. During the 1-year follow-up period, 17.1% of the IL-1RN*2 allele carriers and 24.9% of the homozygous IL-1RN*1 allele carriers needed target vessel revascularization (P=0.013). Thus, the presence of the IL-1RN*2 allele was associated with a 37% reduction (odds ratio: 0.63 [0.43–0.91]; FIG. 1, right panel) of the need of ischemia-driven reinterventions. Quantitative angiographic data obtained for the control study at 6 months (performed in 590 or 85% of patients <60 years) are displayed in Table 8.

TABLE 8

Results at follow-up angiography in patients <60 years.

|  | IL-1RN 1/2 or 2/2 (n = 273) | IL-1RN 1/1 (n = 317) | P |
|---|---|---|---|
| Late lumen loss-mm | 1.08 ± 0.77 | 1.27 ± 0.93 | 0.008 |
| Loss index | 0.49 ± 0.35 | 0.59 ± 0.48 | 0.003 |

TABLE 8-continued

Results at follow-up angiography in patients <60 years.

|  | IL-1RN 1/2 or 2/2 (n = 273) | IL-1RN 1/1 (n = 317) | P |
|---|---|---|---|
| Diameter stenosis-% | 39.3 ± 24.1 | 46.7 ± 30.5 | 0.001 |
| Restenosis rate-% | 25.6 | 38.5 | <0.001 |

Data are proportions or mean ± SD

The incidence of angiographic restenosis was 25.6% in the combined group of IL-1RN 1/2 and IL-1RN 2/2 patients and 38.5% among IL-1RN 1/1 patients (P<0.001), which corresponds to a 45% reduction (odds ratio: 0.55 [0.39–0.78]; FIG. 1, right panel). FIG. 2 illustrates the gene dose effect verified in the subgroup of younger patients. The incidence of restenosis decreased progressively with heterozygosity and homozygosity for the IL-1RN*2 allele. The rate of angiographic restenosis was 38.5% in IL-1RN 1/1 patients, 26.3% in IL-1RN 1/2 patients and 22.4% in IL-1RN 2/2 patients (P=0.001, test for trend). The target vessel revascularization rate was 24.9% in IL-1RN 1/1 patients, 17.9% in IL-1RN 1/2 patients and 13.2% in IL-1RN 2/2 patients (P=0.01, test for trend; FIG. 2).

5.3. Example 3. The IL-1 Haplotype Patterns Asociated With Occlusive Cardiovascular Disorders and Perindontitis The association between periodontitis, cardiovascular disease and four basic biallelic markers (IL-1A (+4845), IL-1B (+3954), IL-1B (−511), and IL-1RN (+2018)) in the interleukin-1 (IL-1) gene cluster on chromosome 2 was investigated.

Two haplotype patterns may be defined by four polymorphic loci in the IL-1 gene cluster as shown in Table 9 (IL-1A(+4845), IL-1B(+3954), IL-1B (−511), IL-1RN(+2018)). One pattern includes allele 2 at both the IL-1A (+4845) and at the IL-1B (+3954) loci. The other pattern includes allele 2 at both the IL-1B(−511), and at the IL-1RN (+2018) loci.

TABLE 9

| Haplotypes | IL-1A (+4845) | IL-1B (+3954) | IL-1B (−511) | IL-1RN (+2018) |
|---|---|---|---|---|
| Pattern 1 | Allele 2 | Allele 2 | Allele 1 | Allele 1 |
| Pattern 2 | Allele 1 | Allele 1 | Allele 2 | Allele 2 |

The haplotype pattern indicates that when allele 2 is found at one locus, it is highly likely that it will be found at other loci. Previous data (Cox et al. (1998) Am. J. Hum. Genet. 62:1180–1188) indicate that when allele 2 is found at the IL-1A (+4845) locus allele 2 will also be present at the IL-1B (+3954) locus approximately 80% of the time. Haplotype patterns are relevant only for a single copy of a chromosome. Since there are two copies of chromosome 2 and standard genotyping procedures are unable to identify on which chromosome copy a specific allele is found, special statistical programs are used to infer haplotype patterns from the genotype pattern that is determined.

The distribution of these genetic patterns was evaluated in a new population that was part of a study of atherosclerosis (Pankow et al. (1999) The ARIC study. European Atherosclerosis Society Annual Meeting, Abstract, #646). In this population (N=1,368), IL-1A(+4845) genotype 2.2 was found in 10.2% of the subjects. However, in the subjects with genotype IL-1B (+3954)=2.2 (N=95), the IL-1A (+4845) genotype 2.2 was found in 71.6% of the subjects. This indicates that allele 2 at IL-1A (+4845) is inherited together with allele 2 at IL-1B (3954) at a much higher rate than one would expect given the distribution of each of these markers in the population. Similar data exists for allele 2 at the 2 loci that are characteristic of Pattern 2. In addition, when genotype Pattern 1 is found it is highly unlikely that allele 2 will be present at either of the loci that are characteristic of the other pattern.

The two genotype patterns are also associated with specific differences in the functional biology of interleukin-1. For example, peripheral monocytes from individuals with one or two copies of allele 2 at IL-1B (+3954) produced 2 to 4 times as much IL-1β when stimulated with LPS as monocytes from individuals who have the genotype pattern IL-1B (+3954)=1.1 (DiGiovini, F S et al. (1995) Cytokine, 7:606). Similar data have recently been reported for peripheral blood polymorphonuclear leukocytes isolated from individuals with severe periodontitis (Gore, E A et al. (1998) J. Clin. Periodontol., 25:781). In addition gingival crevice fluid (GCF) from subjects with the composite genotypes indicative of Pattern 1 have 2 to 3 times higher levels of IL-1β than GCF from individuals who are negative for those genotypes (Engelbretson, S P et al. (1999) J. Periodontol., in press). There are also data indicating that for Pattern 2, allele 2 at IL-1RN +2018 is associated with decreased levels of IL-1 receptor antagonist protein. Thus, Pattern 1 genotypes appear to be associated with increased IL-1 agonists, and Pattern 2 appears to be associated with decreased levels of IL-1 receptor antagonist.

The composite IL-1 genotypes that are consistent with Pattern 1 are associated with increased susceptibility to severe adult periodontitis (Komman, K S et al. (1997), supra; Gore, E A et al. (1998), supra; McGuire, M K et al. (1 999) J. Periodontol., in press; McDevitt, M J et al. (1999) J. Periodontol., in press). One aspect of the IL-1 genotype influence on periodontitis appears to be an enhancement of the subgingival levels of specific bacterial complexes that include accepted periodontal pathogens (Socransky, S S et al. (1999) IADR Annual Meeting, Abstract#3600). Pattern 1 genotypes were not, however, associated with increased risk for occlusive cardiovascular disease. In data from the Atherosclerosis Risk in Communities (ARIC) study that was presented by Pankow and co-workers (see Pankow et al., supra), individuals with ultrasound measurements of carotid wall intima-medial thickness (IMT) that were indicative of occlusive cardiovascular disorders were compared to a stratified random control population for IL-1 gene polymorphisms. Neither IL-1A (+4845) or IL-1B (+3954) showed any association with risk for high IMT.

Genotypes that are characteristic of pattern 2 have recently been associated with increased susceptibility to occlusive coronary artery disease, but not increased risk for periodontitis. In a report on coronary artery disease, patients with an iographic evidence of coronary stenoses were significantly more likely to be carriers of allele 2 at either the IL-1RN (+2018) locus or the IL-1B (−511) locus (see Francis et al., supra). Both loci are characteristic of the haplotype Pattern 2. In the ARIC study, as discussed above, carriage of IL-1RN (+2018) allele 2 in African-Americans with high IMT measurements was significantly higher than ethnically matched controls. In Caucasians with high IMT measurements the carriage of one copy of allele 2 at IL-1RN (+2018) was significantly greater than in controls, however individuals homozygous at this locus were not different from controls. It should be noted that the prevalence of individuals homozygous for allele 2 at IL-1RN (+2018) in Caucasians in the study was substantially lower than that observed in other populations.

When individuals with periodontitis and gingival health were evaluated for genotype patterns consistent with Pattern 1 and Pattern 2, individuals with severe adult periodontitis were found to have a predominance of genotypes consistent with Pattern 1, whereas individuals with a healthy periodontal condition had genotype patterns that were dominated by neither Pattern 1 nor Pattern 2. It appears therefore that IL-1 genotypes consistent with the haplotype Pattern 1 are associated with severe periodontitis and plaque fragility disorders and not occlusive cardiovascular diseases whereas IL-1 genotypes consistent with the haplotype Pattern 2 are associated with occlusive cardiovascular diseases but not periodontitis or plaque fragility. One mechanism may be that IL-1 genotype Pattern 1 directly influences plaque fragility; another mechanism may be that Pattern 1 influences periodontitis directly, which may lead to indirect influences on cardiovascular disease through the periodontal micororganisms found as part of the oral chronic inflammatory process. Another mechanism may be that L-1 genotype Pattern 2 directly influences cardiovascular occlusive disorders but has no influence on periodontitis. It is thus likely that IL-1 genetic polymorphisms can influence both cardiovascular disease and severe periodontitis, by a common underlying mechanism that directly alters the immunoinflammatory responses in both diseases in an identical fashion and by an indirect mechanism that enhances the oral bacterial load and then influences cardiovascular disease. The IL-1 genotypes that are consistent with haplotype Pattern 1 may influence the association between periodontidis and cardiovascular disease in one segment of the population by amplifying both the immuno-inflammatory response and the subgingival bacterial load.

5.4 Example 4 Genotyping Methods
Preparation of DNA

Blood is taken by venipuncture and stored uncoagulated at −20° C. prior to DNA extraction. Ten milliliters of blood are added to 40 ml of hypotonic red blood cell (RBC) lysis solution (10 mM Tris, 0.32 Sucrose, 4 mM $MgCl_2$, 1% Triton X-100) and mixed by inversion for 4 minutes at room temperature (RT). Samples are then centrifuged at 1300 g for 15 minutes, the supernatant aspirated and discarded, and another 30 ml of RBC lysis solution added to the cell pellet. Following centrifugation, the pellet is resuspended in 2 ml white blood cell (WBC) lysis solution (0.4 M Tris, 60 mM EDTA, 0.15 M NaCl, 10% SDS) and transferred into a fresh 15 ml polypropylene tube. Sodium perchlorate is added at a final concentration of 1M and the tubes are first inverted on a rotary mixer for 15 minutes at RT, then incubated at 65° C. for 25 minutes, being inverted periodically. After addition of 2 ml of chloroform (stored at −20° C.), samples are mixed for 10 minutes at room temperature and then centrifuged at 800 G for 3 minutes. At this stage, a very clear distinction of phases can be obtained using 300 1 Nucleon Silica suspension (Scotlab, UK) and centrifugation at 1400 G for 5 minutes. The resulting aqueous upper layer is transferred to a fresh 15 ml polypropylene tube and cold ethanol (stored at −20° C.) is added to precipitate the DNA. This is spooled out on a glass hook and transferred to a 1.5 ml eppendorf tube containing 500 1 TE or sterile water. Following overnight resuspension in TE, genomic DNA yield is calculated by spectrophotometry at 260 nm. Aliquots of samples are diluted at 100 ug/ml, transferred to microtiter containers and stored at 4° C. Stocks are stored at −20° C. for future reference.

5.4.1 Polymerase Chain Reaction

Oligonucleotide primers designed to amplify the relevant region of the gene spanning the polymorphic site (as detailed below) are synthesized, resuspended in Tris-EDTA buffer (TE), and stored at −20° C. as stock solutions of 200 $\mu M$. Aliquots of working solutions (1:1 mixture of forward and reverse, 20 $\mu M$ of each in water) are prepared in advance.

Typically, PCR reaction mixtures are prepared as detailed below.

| | Stock Concentration | | Volume | Final Concentration |
|---|---|---|---|---|
| Sterile $H_2O$ | | | 29.5 $\mu l$ | |
| 10 × PCR buffer | 200 | mM Tris-HCl (pH 8.4) | 5.00 $\mu l$ | 20 mM Tris-$HCl_2$ |
| $MgCl_2$ | 50 | mM | 1.75 $\mu l$ | 1.75 mM |
| dNTP | mix 10 | mM of each | 4.00 $\mu l$ | 0.2 mM of each |
| primer forward | 20 | uM | 2.5 $\mu l$ | 1 uM |
| prime reverse | 20 | uM | 2.5 $\mu l$ | 1 uM |
| Taq polymerase | 5 | U/$\mu l$ | 0.25 $\mu l$ | 1.25 units/50 $\mu l$ |
| Detergent (eg W-1, Gibco) | 1% | | 2.5 $\mu l$ | 0.05% |
| Template | 200 | ng/$\mu l$ | 2.00 $\mu l$ | 2 ng/l |
| Final Volume | | | 50.00 $\mu l$ | |

DNA template is dotted at the bottom of 0.2 ml tubes or microwells. The same volume of water or negative control DNA is also randomly tested. A master-mix (including all reagents except templates) is prepared and added to the wells or tubes, and samples are transferred to the thermocycler for PCR.

PCR can be performed in 0.5 ml tubes, 0.2 ml tubes or microwells, according to the thermocycler available. The reaction mixture is overlaid with mineral oil if a heated lid (to prevent evaporation) is not available.

5.4.2 Restriction Enzyme Digestion

A master mix of restriction enzyme buffer and enzyme is prepared and aliquotted in suitable volumes in fresh microwells. Digestion is carried out with an oil overlay or capped microtubes at the appropriate temperature for the enzyme on a dry block.

Restriction buffer dilutions are calculated on the whole reaction volume (i.e. ignoring salt concentrations of PCR buffer). Restriction enzymes are used 3–5 times in excess of the recommended concentration to compensate for the unfavorable buffer conditions and to ensure complete digestion.

5.4.3 Electrophoresis

Polyacrylamide-gel electrophoresis (PAGE) of the PCR sample is carried out in Tris-HCl-EDTA buffer and at constant voltage. Depending on the size discrimination need, different PAGE conditions are used (9 to 12% acrylamide, 1.5 mm×200) and different DNA size marker (X174-Hae III or X 174-Hinf 1). A 2% agarose horizontal gel can be used for genotyping the IL-1RN (VNTR) marker.

5.4.4 Allele Detection Methods

The following Table 10 provides methods for detecting particular alleles that are associated with the existence of or susceptibility to developing restenosis.

TABLE 10

|  | IL-1A (+4845) |
| --- | --- |
| 5' Primer | ATG.GTT.TTA.GAA.ATC.ATC.AAG.CCT.AGG.GCA (+4814/+4843) (SEQ ID No. 1) |
| 3' Primer | AAT.GAA.AGG.AGG.GGA.GGA.TGA.CAG.AAA.TGT (+5015/+5044) (SEQ ID No. 2) |
| PCR Conditions | MgCl$_2$ is used at 1 mM final, and PCR primers at 0.8 mM. DMSO is added at 5%, DNA template at 150 ng/50 ml, and TaqMan 1.25 u/50 µl. |
| Cycling conditions | 1 × [95° C. 1 min.]; 35 × [94° C. 1 min., 56° C. 1 min., 72° C. 2 min.]; 1 × [72° C. 5 min.]; 4° C. |
| Analysis | Cleavage with 2.5 units of Fnu4H1 in addition to 2 ml of the specific 10 restriction buffer at 37° C. overnight, followed by 9% PAGE analysis yields a constant band of 76 bp (absence indicates incomplete digestion) and two further bands of 29 and 124 bp (allele 1), or a single band of 153 bp (allele 2). Allele frequencies in North British Caucasian population are 0.71 and 0.29. |
| Reference | Gubler, et al.(1989) Interleukin, inflammation and disease (Bomford and Henderson, eds.) p.31–45, Elsevier publishers; and Van den velden and Reitsma (1993) Hum Mol Genetics 2:1753–50). GenBank Accession No. X03833. |
|  | IL-1B (−511) |
| 5' Primer | TGG.CAT.TGA.TCT.GGT.TCA.TC (−702/−682) (SEQ ID No: 3) |
| 3' Primer | GTT.TAG.GAA.TCT.TCC.CAC.TT (−417/−397) (SEQ ID No: 4) |
| PCR Conditions | 50 mM KCl, 10 mM Tris-HCl, pH 9.0, 1.5 mM MgCl$_2$, 200 mM dNTPs, 25 ng primers, 50 ng template, 0.004% W-1 (Gibco-BRL), 0.2 U Taq polymerase, 50 µl total volume |
| Cycling conditions | 1 × [95° C. 2 min.]; 35 × [95° C. 1 min., 53° C. 1 min., 72° C. 1 min.]; 1 × [72° C., 5 min.]; 4° C. |
| Analysis | Each PCR reaction is divided into two 25 µl aliquots: one is added of 3 units of Ava I restriction endonuclease, the other 3.7 units of Bsu 36 I, in addition to 3 µl of the specific 10x restriction buffer. Incubation is at 37° C. overnight. Electrophoresis is by PAGE 9%. Cleavage with Ava I and Bsu 36I. Allele 1 (C) produces 190 and 114 bp fragments when digested with Ava I and a 304 bp fragment when digested with Bsu 361. Allele 2 (T) produces a 304 bp fragment when digested with Ava I and 190 and 114 bp fragments when digested with Bsu 36I. The restriction pattern obtained should be the inverse in the two aliquots (identifying homozygotes) or identical (heterozygotes). Frequencies in North British Caucasian population are 0.61 and 0.39 for allele 1 and 2 respectively. |
| Reference | diGiovine, Hum. Molec. Genet., 1(6):450 (1992); Clark, et al., Nucl. Acids. Res., 14:7897–7914 (1986) [published erratum appears in Nucleic Acids Res., 15(2):868 (1987)]; GenBank Accession No. X04500. |
|  | IL-1B (+3954) |
| 5' Primer | CTC.AGG.TGT.CCT.CGA.AGA.AAT.CAA.A (+3844/+3868) (SEQ ID NO:5) |
| 3' Primer | GCT.TTT.TTG.CTG.TGA.GTC.CCG (+4017/+4037) (SEQ ID No:6) |
| PCR Conditions | 50 mM KCl, 10 mM Tris-HCl, pH 9.0, 1.5 mM MgCl$_2$, 200 mM dNTPs, 25 ng primers, 50 ng template, 0.004% W-1 (Gibco-BRL), 0.2 U Taq polymerase, 50 µl total volume |
| Cycling conditions | 1 × [95° C. 2 min.]; 35 × [95° C. 1 min., 67.5° C. 1 min., 72° C. 1 min); 1 × [72° C., 5 min.]; 4° C. |
| Analysis | Each PCR reaction is added of 10 u of Taq 1 restriction endonuclease in addition to 3 µl of the specific 10x restriction buffer. Incubation is at 65° C. overnight. Electrophoresis is by PAGE 9%. Following digestion with Taq I, Allele 1 produces 97, 85 and 12 bp fragments; Allele 2 produces 182 and 12 bp fragments. The absence of the 12 bp band indicates incomplete digestion. Frequencies in a North British Caucasian population are 0.82 (allele 1) and 0.18 (allele 2). For 90% power at 0.05 level of significance in a similar genetic pool, 408 cases should be studied to detect 1.5 fold increase in the frequency, or 333 for 0.1 absolute increase in frequency. |
| Reference | di Giovine, et al. Cytokine 7(6): 606 (1995) |
|  | IL-1RN (VNTR) |
| 5' Primer | CTC.AGC.AAC.ACT.CCT.AT (+2879/+2895) (SEQ ID NO. 7) |
| 3' Primer | TCC.TGG.TCT.GCA.GGT.AA (+3274/+3290) (SEQ ID NO. 8) |
| PCR Conditions | 50 mM KCl, 10 mM Tris-HCl pH 9.0, 1.7 mM MgCl$_2$, 200 mM dNTPs, 25 ng primers, 50 ng template, 0.004% W-1 (Gibco-BRL) 0.2 u Taq polymerase |
| Cycling conditions | 1 × [96° C. for 1 min.]; 30 × [94° C. for 1 min., 60° C. for 1 min., 70° C. for 1 min.]; 1 [70° C. for 2 min.]. |
| Analysis | The variable number of tandem repeats (VNTR) in intron 2 of IL1-RN corresponds to a variable number (2 to 6) of an 86 bp repeat and so the PCR product sizes are a direct indication of the number of repeats. Electrophoresis is by 2% agarose, 90 V, 30 min. |

TABLE 10-continued

|  |  |  |  |
|---|---|---|---|
|  | Allele 1 | 4 repeats | 412 bp PCR product |
|  | Allele 2 | 2 repeats | 240 bp PCR product |
|  | Allele 3 | 3 repeats | 326 bp PCR product |
|  | Allele 4 | 5 repeats | 498 bp PCR product |
|  | Allele 5 | 6 repeats | 584 bp PCR product |
|  | Frequencies in a North British Caucasian population for the four most frequent alleles are 0.734, 0.241, 0.021 and 0.004. | | |
| Reference | Steinkasserer et al. (1991) Nucleic Acids Research 19:5090–95; Tarlow, et al., Hum. Genet. 91: 403–4 (1993) | | |
|  | IL-1RN (+2018) | | |
| 5' Primer | CTA.TCT.GAG.GAA.CAA.CCA.ACT.AGT.AGC-3' (+1992/+2017) (SEQ ID No.9) | | |
| 3' Primer | TAG.GAC.ATT.GCA.CCT.AGG.GTT.TGT-3' (+2135/+2158) (SEQ ID No. 10) | | |
| PCR Conditions | Each PCR reaction is divided in two 25 µl aliquots; to one is added 5 Units of Alu I, the other 5 Units of Msp I, in addition to 3 µl of the specific 10X restriction buffer. Incubation is a 37° C. overnight. Electrophoresis is by PAGE 9%. | | |
| Cycling conditions | 1 × [96° C. for 1 min]; 35 × [94° C. for 1, min., 57° C. for 1 min 70° C. for 2 min.]; 1 × [70° for 5 min.]; 4° C. | | |
| Allele Detection | The above described PCR primers incorporate mismatches to the genomic sequence so as to engineer two different restriction sites on the alleles. The two alleles are 100% in linkage disequilibrium with the two most frequent alleles of IL-1RN (VNTR). Alu I will produce 126 + 28 bp fragments for Allele 1, while it does not digest Allele 2 (154 bp). Msp I will produce 125 + 29 bp with Allele 2, while Allele 1 is uncut (154 bp). Hence the two reactions (separated side by side in PAGE) will give inverted patterns of digestion for homozygote individuals, and identical patterns in heterozygotes. Allelic frequencies in a North British Caucasion population are 0.74 and 0.26. For 90% power at 0.05 level of significance in a similar genetic pool, 251 cases should be studied to detect 1.5 fold increase in frequency, or 420 for 0.1 absolute increase in frequency. | | |
| Reference | Clay, et al.(1996) Hum. Genet. 97: 723–26. | | |

Results: Typing of additional numbers of individual is required to bring the results to significance, but preliminary results indicate that allele 1 of the 4845, −511, +3954 and VNTR markers in the IL-1RN gene will be over-reoresented in restenosis. It is predicted that individuals with at least one copy of allele 1 from one of the above markers are more likely to have restenosis than those who are negative for allele 1. Individuals who are homozygous for any of these alleles, or have allele 1 from more than one marker are estimated to have even higher risk for restenosis.

5.5 Example 5

In this example, the preparation of template DNA is described. PCR-based genotyping does not require particularly high-MW DNA (<20 Kb DNA is often an excellent template). As 100 ng genomic DNA is more than sufficient for single-copy gene amplification, direct amplification from dried blood spots or cell lysates can be used for genotyping, and two of the protocols that we have used are here described below.

However, if DNA banks need to be established for population studies where DNA needs to be stored for future reference or genotyping at different loci, or where genomic Southern blotting might be needed, good quality high-MW genomic DNA needs to be extracted. Basic buffers and the composition of chemical solutions can be found in major protocol textbooks (Sambrook et al. (1989) Molecular cloning: a laboratory manual, Cold Spring Harbor Press; Ausubel and Frederick (1994) Current protocols in molecular biology, John Wiley and Sons).

Sample DNA can also be obtained from dried blood spots. Such a means of sample collection (Guthrie spots) has been used for many years in neonatal diagnosis of phenylketonuria. In the last few years dried blood spots have proved useful in PCR-based diagnostics (Raskin et al. (1991) Am J Hum Genet 49: 320–29). Uncoagulated blood is spotted evenly using a sterile Pasteur pipette onto a clean sheet of filter paper. This is left to dry overnight in a clean area (physically isolated from post-PCR events) and stored subsequently at room temperature.

For PCR, a mastermix is prepared as described later in this chapter, where Taq polymerase is omitted. This is aliquotted in reaction tubes, and approximately 1 mm$^2$ of the blood spot is cut out and placed into the reaction mix. This is overlaid with 40 µl mineral oil. The lid of each tube is pierced with a sterile needle, and samples are then heated at 980° C. for 15 minutes. Following cooling for a few minutes, Taq polymerase is added and standard PCR cycling follows.

Sample DNA can also be obtained from cell lysates. White blood cells, buccal cells or homogenised tissue is suspended in PK buffer (0.1M NaCl, 10 mM Tris-HCl, 25 mM EDTA, 0.5% SDS pH 8.0, 0.1 mg/ml fresh Proteinase K) and incubated on a tumbler at 37° C. for 1 hour. Samples are heated at 95° C. for 10 mins, spun at 13,000 rpm in a microfuge and supernatants stored at −20° C. prior to PCR. For higher quality DNA, a phenol/chloroformn extraction followed by ethanol precipitation can be added.

Sample genomic DNA can also be obtained from whole blood. Blood is taken by venepuncture and stored uncoagulated at −20° C. prior to DNA extraction. When possible, we prefer to collect two 10 ml samples, extract DNA form the first and keep the second for future reference. Ten milliliters of blood are added to 40 ml of hypotonic red blood cell (RBC) lysis solution (10 mM Tris-HCl, 0.32 Sucrose, 4 mM MgCl$_2$, 1% Triton X-100) and mixed by inversion for 4 minutes at room temperature. Samples are then centrifuged at 1300 g for 15 minutes, the supernatant aspirated and discarded, and another 30 ml of RBC lysis solution added to the cell pellet. Following centrifugation, the pellet is resuspended in 2 ml white blood cell (WBC) lysis solution (0.4M Tris-HCl, 60 mM EDTA, 0. 15M NaCl, 10% SDS) and transferred into a fresh 15 ml polypropylene tube. Sodium perchlorate is added at a final concentration of 1M and the tubes are first inverted on a rotary mixer for 15 minutes at room temperature (RT), then incubated at 65° C. for 25 minutes, being inverted periodically. After addition of 2 ml of chloroform (stored at −20° C.), samples are mixed for 10 minutes at room temperature and then centrifuged at 800 g for 3 minutes. At this stage a very clear distinction of phases can be obtained using 300 µl Nucleon Silica suspension (Scotlab, UK) and centrifugation at 1400 G for 5 minutes. The resulting aqueous upper layer is transferred to a fresh 15 ml polypropylene tube and cold ethanol (stored at −20° C.) is added to precipitate the DNA. This is spooled out on a glass hook and transferred to a 1.5 ml eppendorf tube or containing 500 µl TE or sterile water. Following overnight resuspension in TE, genomic DNA yield is calculated by spectrophotometry at 260 nm. Aliquots of samples are diluted at 100 µg/ml, transferred to microtiter containers and stored at 4° C. Stocks are stored at −20° C. for future reference.

5.6 Example 6

In this example, the conditions for conducting appropriate polymerase chain reactions on the collected samples are described. Oligonucleotide primers designed to amplify the relevant region of the gene spanning the polymorphic site (as detailed below) are synthesised, resuspended in Tris-HCl-EDTA buffer (TE) and stored at −20° C. as stock solutions of 200 µM. Aliquots of working solutions (1:1 mixture of forward and reverse, 20 µM of each in water) are prepared in advance of the experiment. Typically PCR reaction mixtures are prepared as detailed below. Divergence from the scheme below can be made for each specific protocol.

|  | Stock Concentration | Volume | Final Concentration |
| --- | --- | --- | --- |
| Sterile H$_2$O |  | 29.5 µl |  |
| 10 × PCR buffer | 200 mM Tris-HCl (pH 8.4), 500 mM KCl | 5.00 µl | 20 mM Tris-HCl, 50 mM KCl |
| MgCl$_2$ | 50 mM | 1.75 µl | 1.75 mM |
| dNTP | mix 10 mM of each | 4.00 µl | 0.2 mM of each |
| primer forward | 20 µM | 2.5 µl | 1 µM |
| primer reverse | 20 µM | 2.5 µl | 1 µM |
| Taq polymerase | 5 U/µl | 0.25 µl | 1.25 units/50 µl |
| Detergent (eg W-1 Gibco) | 1% | 2.5 µl | 0.05% |
| Template | 200 ng/µl | 2.00 µl | 2 ng/µl |
| Final volume |  | 50.00 µl |  |

DNA template is dotted at the bottom of 0.2 ml tubes or microwells. The same volume of water or negative control DNA is also randomly tested. A master-mix (including all reagents except templates) is prepared and added to the wells or tubes, and samples are transferred to the thermocycler for PCR.

PCR can be performed in 0.5 ml tubes, 0.2 ml tubes or microwells, according to the thermocycler available and to the needs of the project. The reaction mixture is overlaid with mineral oil if a heated lid (to prevent evaporation) is not available. We use 96-well format microplates, because they allow use of multichannel pipettes both for transfer of template DNA (stored in 1 ml/microwell plates) and for dispensing of the reaction mastermix.

5.7 Example 7

In this example, the conditions for conducting appropriate polymerase chain reactions on the collected samples are described. A master mix of restriction enzyme buffer and enzyme is prepared and aliquotted in suitable volumes in fresh microwells. We use a multichannel pipette to transfer and mix 25–30 µl of PCR product in the microwells. Digestion is carried out with an oil overlay or capped microtubes at the appropriate temperature for the enzyme on a dry block. Restriction buffer dilutions are calculated on the whole reaction volume (i.e. ignoring salt concentrations of PCR buffer). Restriction enzymes are used 3–5 times in excess of the recommended concentration, to compensate for the unfavorable buffer conditions and to ensure complete digestion.

5.8 Example 8

In this example, the conditions for conducting gel electorphoresis analysis of the products of pcr amplification and restriction endonuclease digestion are considered. Polyacrylamide-gel electrophoresis (PAGE) of 20–40 µl PCR sample is carried out in Tris-HCl-EDTA buffer and at constant voltage. Depending on the size discrimination needed, different PAGE conditions are used (9 to 12% acrylamide, 1.5 mm×200) and different DNA size markers (φX174-Hae III or (φX174-HinfI). A 2% agarose horizontal gel can be used for 1RN (VNTR).

5.9 Example 9

In this example, quality controls for these genotyping protocols are considered. Incomplete digestion is the most common cause of mis-typing in PCR-RFLP genotyping methods. Most of the protocols described herein are based on a double-cut strategy, for which either a second restriction cutting site is used for digestion control on the diagnostic cleavage, or one enzyme cuts one allelic DNA form, and a different enzyme cuts the other allele. In this case each reaction is the control for the other. PCR conditions are tested (and, if necessary, re-optimised) for each DNA preparation not performed in our laboratory. Template DNA quality is assessed by spectrophotometry and by gel electrophoresis.

The possibility of cross-contamination is very high in PCR-based techniques. Although the genotyping is physically separated from any lab where relevant cloned fragments are being handled, it is still possible to have PCR-product carryover from previous experiments (from labcoat, hair, skin, etc.). A "TCR-carryover prevention kit" is available from Perkin-Elmer. This is based on UNG treatment of samples prior to PCR, which will cleave all dUTP-containing DNA. As all PCRs are performed using dUTP instead of dTTP, all previous PCR products, but not native templates, will be cleaved in this digestion step. This enzyme is inactivated by the first temperature ramping (94° C.) and therefore normal PCR can take place without UNG activity. If laboratories do not use this system (which is expensive), there are stringent rules that can be used to reduce the risk of artefacts due to contamination.

5.10 Example 10

In this example, the prevention of contamination in these genotyping protocols is considered. Incomplete digestion is the most common cause of mis-typing in PCR-RFLP genotyping methods.

Laboratories are divided into GREEN (Pre-PCR) and RED (Post-PCR) areas. All laboratories have dedicated white coats, and workers are encouraged to change lab gloves as frequently as possible. GREEN laboratories have the most stringent requirements. Only goods coming from other green areas can enter, anything (equipment included) that leaves them cannot re-enter. These usually include a store-room, a "sample reception" area, a "clean DNA room" (where DNA extraction and PCR preparation are performed) and offices. RED laboratories have open access, but material and equipment can only move to other red areas or disposed of in bags for autoclaving or incineration. Red areas are where PCR and electrophoresis take place. Results and images are stored in computer files and transferred to the offices by local network.

All PCR's carry 10% negative controls which are randomly placed within the experiment. These are routinely represented by water controls. In the case of amplicards, negative controls are represented also by fragments (2–3-mm$^2$) of paper from the edge of the card. For human blood DNA preparations, murine T cell lysates are extracted at the same time as each new batch of frozen blood, and resulting DNA used as negative control.

5.11 Example 11

In this example, the design of human polymorphic marker association studies are examined and the resulting data is analyzed. Traditional parametric analyses (requiring the specification of a distribution and/or the mode of inheritance) have been used successfully to locate genes for monogenic diseases following simple Mendelian modes of inheritances. More commonly used in the genetic analysis of complex diseases are non-parametric methods since these work independently of inheritance specifications, and are generally more powerful than parametric methods when parameters are mis-specified. The choice of method of analysis depends on whether the investigator wishes to perform a whole genome screen or use a candidate gene approach, since certain methods are best suited to just one of these two approaches or to specific pedigree structures. The following sections contain an outline of most commonly used non-parametric methods of analysis and their suitability to the candidate gene approach.

An allele at a certain locus is said to be associated with a disease if the frequency for that allele is significantly increased in the disease population over that of the normal healthy control population. True associations are due to linkage disequilibrium, where the disease causing allele at the 'disease' locus remains on the same haplotype as those alleles which were present at closely flanking loci when the ancestral mutation occurred. Thus, the frequency of any allele on the 'disease haplotype' (including, of course, the disease allele itself) will be increased in the disease population. Recombination over extremely small distances is very low, but as the time from the ancestral mutation increases, the distance over which linkage disequilibrium acts decreases reducing the length of the 'disease haplotype'. It is therefore easier to detect association in young, isolated populations with a single founder mutation effect where linkage extends over larger distances, than in large mixed populations.

Association studies are at present only suited to the candidate gene approach due to the small distances over which associations are detectable. In the future it is proposed that genome-wide association studies will be performed using several biallelic markers in every gene. Care must be taken when selecting the disease population in an association study, since spurious positive results may occur as an artefact of population admixture. It is usually advisable to investigate within a single ethnic group, since allele frequencies may vary between different groups. Similarly, if a control population is needed, it must be matched to the disease group for ethnicity, and ideally sex and age.

Case control studies can be performed for both qualitative and quantitative phenotypes. Obvious advantages of this approach include the ease of collection of large populations, the possibility of recruitment of patients with "early disease" phenotypes, and the possibility of analyzing late-onset diseases, where parental DNA may not be available.

For qualitative phenotypic studies, the candidate gene locus, allele frequencies or alternatively genotype frequencies, within the disease and control populations are calculated. The analysis is simple, comprising of a 2×n contingency table (n denoting the number of categories, 2 for allele frequencies or 3 for genotypes at a biallelic locus), which a chi-square test may be used to determine whether the proportions differ significantly between the disease and control populations.

For quantitative phenotypic studies looking for a disease susceptibility allele, the individuals in both populations are first phenotyped quantitatively (usually the disease is classified as attaining a certain threshold value, therefore the unaffected controls are individuals failing below this). All individuals are then subdivided into the three (or more) genotypes. If an allele responsible for the inflated phenotype value of the diseased individuals exists, it would be expected that these individuals carry at least, one copy of it. Thus the median of these genotype groups would be higher than those of the non-carrier groups. The non-parametric test involves testing for significant difference between the medians of the different genotype (or carriage) groups. This may be done via a Mann-Whitney test (for 2 groups), or a Kruskall-Wallis (for >2 groups), although several other tests also exist. In exactly the same way, this type of analysis may also be performed solely within the disease group.

For use of qualitative traits in studies employing more than one IL-1 polymorphic locus, the simple one locus case-control analysis can be extended to one involving several loci (given a sufficient sample size). In a similar way, a larger contingency table can be calculated, with groups corresponding now to composite genotypes. As before, a chi-squared statistic can be calculated. With these large contingency tables, it is likely that the validity of the chi-square test is violated (<80% of expected values >5, and expected values <1). With smaller contingency tables, the usual remedy to violations of validity is to use Fishers Exact test, but in this larger case, it is not viable. Instead a null distribution for the evaluated chi-square statistic is simulated, and significance assessed from this. This test has been named the Monte Carlo Composite Genotype (MCCG) test.

5.12 Example 12

In this example, haplotype relative risk (HRR) analysis is discussed. This analysis is only suitable for qualitative traits (quantitative traits may be used if, dichotomised), and as with all association tests, the candidate gene approach. Haplotype analysis investigates the association between specific genetic markers for diseases and the way a set of markers may influence the outcome of the disease. Analyzing the relationship between specific genetic markers and disease is an extremely complex process. The analysis needs to take into account (i) the relation between genetic markers in neighboring genes, (ii) the way the polymorphic markers affect expression of the gene in question, (iii) the distribution of the genetic markers for a specific polymorphism over both chromosomes, and (iv) the way the expressed gene product(s) affect the disease process. The relationship between these factors can be identified by statistical equations that look at multipoint linkage analysis, transmission/disequilibrium test (TDT), multipoint quantitative trait loci (QTL) analysis, identity-by-state (IBS), identity-by-descent (IBD), and grouping of multiallelic markers for biological functions related to disease. This approach has been described by Camp ((1997) American Journal of Human Genetics 61: 1424–30); Cox et al ((1998) American Journal of Human Genetics 62: 1180–88); and Almasy and Blangero ((1998) American Journal of Human Genetics 62: 1198–1211).

To perform a HRR analysis (Falk et al. (1987) Ann Hum Genet 51: 27–233) nuclear families with affected offspring are needed. This type of analysis uses an artificial internal control, and therefore the problem of collecting an independent matched control population is removed. The parents and affected offspring are genotyped. It is then established which parental alleles were passed on to the affected offspring and which were not. From this the transmitted genotype and the non-transmitted genotype (internal control) are determined and recorded in the transmitted and non-transmitted groups, respectively. The two groups are then tested for significant differences in the proportions of their genotypes.

5.13 Example 13

In this example, the transmission/disequilibrium test (TDT) is discussed. This analysis is suitable for qualitative traits investigated using a candidate gene approach. Nuclear families are needed, including at least one parent, all affected offspring, and if possible an unaffected sibling.

As The TDT (Spielman et al. (1993) Am J Hum Genet 52: 506–16) is a test for both association and for linkage, more specifically, it tests for linkage in the presence of association.

Thus, if association does not exist at the locus of interest, linkage will not be detected even if it exists. It is for this reason that the test has been included in this section. It may be used as an initial test, but is more commonly used when tentative evidence for association has already been identified. In this case, a positive result will not only confirm the initial association, but also provide evidence for linkage.

All parents and affected offspring are genotyped. Only parents heterozygous for the allele of interest may be used in the analysis. If the allele of interest is, or is linked to, the disease allele, the transmission rate for that allele from heterozygous parents to their affected offspring should be elevated. To test if the transmission rate of the allele of interest is significantly elevated, the number of times it is transmitted, b, and the number of times other alleles are transmitted, c, are counted. The squared difference of b and c divided by their sum provides a statistic that follows a chi-square distribution with one degree of freedom, and can thus be assessed for significant deviation from the expected under no association or linkage. It is often advised to repeat this procedure using the unaffected offspring from the same parents to rule out the possibility of a spurious result due to biased meioses.

The TDT may also be used once linkage on a coarse scale has been shown to provide the fine scale mapping that is necessary to pin-point more accurately the disease locus. Of course, these tests are only valid when associations within the area also exist.

5.14 Example 14

In this example, the non-parametric linkage analysis is discussed. Non-parametric linkage analysis methods (such as Affected Sib-Pair analysis, the Haseman-Elston method and Variance Component Method) are based on the allele sharing status of affected relative pairs, usually sibs. These methods are suitable for whole genome screens (commonly done at 10 cM intervals) and also a candidate gene approach (although for fine localisation alternative methods such as the TDT (section 4.2.1.3) should be used).

5.15 Example 15

In this example the analysis of significance and power of the data is examined. Throughout this section, evidence strong enough to suggest association or linkage has been termed significant. The significance level of a test is left to the discretion of the investigator, but conventionally a 5% significance level is used. This means that it is accepted that there is enough evidence to suggest an association (or linkage) if the result would have occurred only 1 in 20 (0.05) times by chance in data where no association (linkage) existed, that is, there is only a 0.05 chance that the result is a false-positive. For each test a p-value may be calculated which indicates the probability of the result occurring by chance. In a single test, if this value is less than 0.05 then significant evidence may be claimed. This concept becomes more complicated when multiple, independent tests are performed. For example, if two tests were performed, and each was tested at the 5% level of significance, overall there is a 2 in 20 (0.1) chance of at least one result being a false-positive. Thus, for two independent tests, to maintain an overall significance level of 0.05 (0.05 chance of at least one test being a false positive) either the individual significance level for each test must be lowered to 0.05/2=0.025, or the p-values doubled before assessing the result. This method of correction is called the Bonferroni correction. More generally, if n independent tests were carried out, each individual test should be tested at the 0.05/n level, or alternatively, every p-value multiplied by n before assessing the results. With non-independent tests, however, the Bonferroni correction may be too conservative.

Many investigators may find that they lose their potential significances through the dilution of p-values due to the correction criteria for multiple tests. Unfortunately these corrections are necessary for statistical correctness and cannot be discarded. However, if the results from the first set of observations are real, a second replication sample need only test those interesting results found from the first. This reduces the number of tests necessary on the second set of observations and thus reduces the dilution, increasing the chance of maintaining the statistical significance that may have been lost the first time. For complex diseases where there are so many questions to be answered it is perhaps unreasonable to expect that a single sample would be sufficient, and instead anticipate the necessity for a two-stage analysis and prepare accordingly. This is especially true for whole genome screens where the corrections necessary are massive. Lander et al. ((1995) *Nature Genet* 11: 241–7) list sensible guidelines for claiming significance in linkage analyses, specifically in the case of genome screens.

Along with significance, a second, and equally important issue is that of power, the ability to pick up significant evidence where it actually exists. Given the phenotype, data structure and number of observations, it is important to choose the method of analysis which is most likely to determine associations or linkages if they exist. In fact, it is advisable that in the planning stages of these studies the number of observations that are necessary to reach a pre-determined power level are calculated. Unfortunately, this task is not as simple as it sounds, since power depends on several factors, of which some may be unknown, for example, allele frequencies, marker informativeness, familial clustering of the disease, recombination between marker and disease locus. Even if these factors are known, the power cannot be explicitly calculated for some methods, and instead empirical powers must be worked out via simulations.

There is no clear answer to which analyses should be done in different situations because of the many variables that are involved. However, it is strongly advisable to make the most informed choice possible, using previous work that has been done, to increase the chances of detection and location of genes responsible, or involved in complex diseases.

What is claimed is:

1. A method for determining whether a single vessel coronary artery disease (SVD) subject has or is predisposed to developing restenosis, comprising detecting IL-1RN (VNTR) allele 1 in a nucleic acid sample from the subject, wherein detection of IL-1RN(VNTR) allele 1 indicates that the subject has or is predisposed to the development of restenosis.

2. A method of claim 1, wherein said detecting step is selected from the group consisting of:
   a) allele specific oligonucleotide hybridization;
   b) size analysis;
   c) sequencing;
   d) hybridization;
   e) 5' nuclease digestion;
   f) single-stranded conformation polymorphism;
   g) allele specific hybridization;
   h) primer specific extension; and
   i) oligonucleotide ligation assay.

3. A method of claim 1, wherein prior to or in conjunction with detection, the nucleic acid sample is subject to an amplification step.

4. A method of claim 3, wherein said amplification step employs a primer pair selected from the group consisting of any of SEQ ID NOs: 1 and 2; 3 and 4; 5 and 6; 7 and 8; 9 and 10; 11 and 12; and 13 and 14.

5. A method of claim 2, wherein said size analysis is preceded by a restriction enzyme digestion.

6. A method of claim 5, wherein said restriction enzyme digestion uses a restriction enzyme selected from the group consisting of Alu I, Msp I, Nco I, Fnu 4HI, Ava I, Bsu 36 I, and Taq I.

7. The method of claim 1, further comprising determining whether allele 1 of IL-1RN(VNTR) is carried in the homozygous state.

8. A method for determining whether a single vessel coronary artery disease (SVD) subject has or is predisposed to developing restenosis, comprising detecting IL-1RN (VNTR) allele 2 in a nucleic acid sample from the subject, wherein detection of IL-1RN(VNTR) allele 2 indicates that the subject is not predisposed to the development of restenosis.

9. The method of claim 8, wherein said detecting step is selected from the group consisting of:
   a) allele specific oligonucleotide hybridization;
   b) size analysis;
   c) sequencing;
   d) hybridization;
   e) 5' nuclease digestion;
   f) single-stranded conformation polymorphism;
   g) allele specific hybridization;
   h) primer specific extension; and
   i) oligonucleotide ligation assay.

10. The method of claim 8, wherein prior to or in conjunction with detection, the nucleic acid sample is subject to an amplification step.

11. The method of claim 10, wherein said amplification step employs a primer pair selected from the group consisting of any of SEQ ID NOs: 1 and 2; 3 and 4; 5 and 6; 7 and 8; 9 and 10; 11 and 12; and 13 and 14.

12. The method of claim 9, wherein said size analysis is preceded by a restriction enzyme digestion.

13. The method of claim 12, wherein said restriction enzyme digestion uses a restriction enzyme selected from the group consisting of Alu I, Msp I, Nco I, Fnu 4HI, Ava I, Bsu 36 I, and Taq I.

14. The method of claim 8, further comprising determining whether allele 2 of IL-1RN(VNTR) is carried in the homozygous state.

* * * * *